US012582818B2

(12) United States Patent
Zellmer et al.

(10) Patent No.: US 12,582,818 B2
(45) Date of Patent: Mar. 24, 2026

(54) SYSTEM AND METHOD FOR SCALING ORTHOPEDIC IMPLANT STIMULATION

(71) Applicant: Intelligent Implants Limited, Cork (IE)

(72) Inventors: Erik Robert Zellmer, Gothenburg (SE); John Zellmer, Gothenburg (SE)

(73) Assignee: Intelligent Implants Limited, Cork (IE)

( * ) Notice: Subject to any disclaimer, the term of this patent is extended or adjusted under 35 U.S.C. 154(b) by 575 days.

(21) Appl. No.: 17/705,244

(22) Filed: Mar. 25, 2022

(65) Prior Publication Data

US 2022/0305258 A1 Sep. 29, 2022

Related U.S. Application Data

(60) Provisional application No. 63/166,143, filed on Mar. 25, 2021.

(51) Int. Cl.
*A61N 1/362* (2006.01)
*A61F 2/28* (2006.01)
*A61F 2/30* (2006.01)
*A61F 2/44* (2006.01)
*A61N 1/05* (2006.01)
*A61N 1/32* (2006.01)

(52) U.S. Cl.
CPC ............... *A61N 1/326* (2013.01); *A61N 1/05* (2013.01)

(58) Field of Classification Search
CPC ........... A61N 1/05; A61N 1/205; A61N 1/326
See application file for complete search history.

(56) References Cited

U.S. PATENT DOCUMENTS

| | | | |
|---|---|---|---|
| 3,842,841 | A | 10/1974 | Brighton et al. |
| 4,175,565 | A | 11/1979 | Chiarenza et al. |
| 4,313,438 | A | 2/1982 | Greatbatch |

(Continued)

FOREIGN PATENT DOCUMENTS

| | | |
|---|---|---|
| EP | 3789079 A1 | 3/2021 |
| JP | H10505248 A | 5/1998 |

(Continued)

OTHER PUBLICATIONS

U.S. Appl. No. 16/592,523, filed Oct. 3, 2019, Rory Kenneth John Murphy.

(Continued)

*Primary Examiner* — Brian T Gedeon
(74) *Attorney, Agent, or Firm* — Alpine Patents LLC; Brian Van Osdol

(57) ABSTRACT

A system and method for spinal fusion that can include: a spinal cage body that includes at least one defined graft window cavity; a plurality of electrodes exposed on the surface of the spinal cage body; control circuitry configured to drive the plurality of electrodes in a stimulation mode; wherein there is at least a targeted osteoinduction region and a targeted non-osteoinduction region that are immediately adjacent to the spinal cage body; and wherein the control circuitry includes configuration to excite the plurality of electrodes during the stimulation mode for generation of a current density in the targeted osteoinduction region and targeted non-osteoinduction region according to targeted levels of bone growth.

14 Claims, 62 Drawing Sheets

(56) References Cited

U.S. PATENT DOCUMENTS

| | | | |
|---|---|---|---|
| 4,690,144 A | 9/1987 | Rise et al. |
| 4,690,166 A | 9/1987 | Howeth |
| 5,056,518 A | 10/1991 | Pethica et al. |
| 5,330,477 A | 7/1994 | Crook |
| 5,358,514 A | 10/1994 | Schulman et al. |
| 5,441,527 A | 8/1995 | Erickson et al. |
| 5,458,627 A | 10/1995 | Baranowski, Jr. et al. |
| 5,565,005 A | 10/1996 | Erickson et al. |
| 5,974,342 A | 10/1999 | Petrofsky |
| 5,989,289 A | 11/1999 | Coates et al. |
| 6,120,502 A | 9/2000 | Michelson |
| 6,292,699 B1 * | 9/2001 | Simon .................... A61N 1/205 |
| | | 607/51 |
| 6,400,990 B1 | 6/2002 | Silvian |
| 6,582,467 B1 | 6/2003 | Teitelbaum et al. |
| 6,605,089 B1 | 8/2003 | Michelson |
| 7,104,986 B2 | 9/2006 | Hovda et al. |
| 7,309,338 B2 | 12/2007 | Cragg |
| 7,324,852 B2 | 1/2008 | Barolat et al. |
| 7,359,755 B2 | 4/2008 | Jones et al. |
| 7,455,672 B2 | 11/2008 | Michelson |
| 7,578,819 B2 | 8/2009 | Bleich et al. |
| 7,935,116 B2 | 5/2011 | Michelson |
| 8,014,873 B2 | 9/2011 | Jones et al. |
| 8,078,282 B2 | 12/2011 | Nycz |
| 8,078,283 B2 | 12/2011 | Cowan et al. |
| 8,206,387 B2 | 6/2012 | Michelson |
| 8,463,401 B2 | 6/2013 | Jones et al. |
| 8,666,471 B2 | 3/2014 | Rogers et al. |
| 8,718,777 B2 | 5/2014 | Lowry et al. |
| 8,740,879 B2 | 6/2014 | Martinson et al. |
| 8,771,360 B2 | 7/2014 | Jimenez et al. |
| 8,838,249 B2 | 9/2014 | Nycz |
| 8,903,502 B2 | 12/2014 | Perryman et al. |
| 10,123,882 B2 | 11/2018 | Stevenson et al. |
| 10,292,831 B2 | 5/2019 | Zellmer et al. |
| 10,617,880 B2 | 4/2020 | Zellmer et al. |
| 11,058,549 B2 | 7/2021 | Zellmer et al. |
| 11,097,096 B2 | 8/2021 | Linden et al. |
| 11,395,744 B2 | 7/2022 | Zellmer et al. |
| 11,471,297 B2 | 10/2022 | Zellmer et al. |
| 11,484,722 B2 | 11/2022 | Zellmer et al. |
| 11,844,706 B2 | 12/2023 | Zellmer et al. |
| 2003/0078634 A1 | 4/2003 | Schulman et al. |
| 2004/0249373 A1 | 12/2004 | Gronemeyer et al. |
| 2005/0033393 A1 | 2/2005 | Daglow |
| 2005/0216702 A1 | 9/2005 | Paolucci et al. |
| 2007/0250045 A1 | 10/2007 | Trieu |
| 2008/0039901 A1 | 2/2008 | Kronberg et al. |
| 2008/0172109 A1 | 7/2008 | Rahman et al. |
| 2008/0294211 A1 | 11/2008 | Moffitt |
| 2008/0300660 A1 | 12/2008 | John |
| 2009/0062886 A1 | 3/2009 | O'Handley et al. |
| 2010/0168829 A1 | 7/2010 | Schwartz et al. |

| | | | |
|---|---|---|---|
| 2010/0204551 A1 | 8/2010 | Roche |
| 2010/0292756 A1 | 11/2010 | Schneider |
| 2011/0009728 A1 | 1/2011 | Schouenborg |
| 2011/0087315 A1 | 4/2011 | Richardson-Burns et al. |
| 2011/0092948 A1 | 4/2011 | Shachar et al. |
| 2011/0301716 A1 | 12/2011 | Sirivisoot et al. |
| 2013/0150970 A1 | 6/2013 | Thaiyananthan |
| 2013/0165991 A1 | 6/2013 | Kim et al. |
| 2013/0296940 A1 | 11/2013 | Northcutt et al. |
| 2014/0114382 A1 | 4/2014 | Kim |
| 2014/0133123 A1 | 5/2014 | Prasannakumar et al. |
| 2014/0275847 A1 | 9/2014 | Perryman et al. |
| 2014/0275859 A1 | 9/2014 | Tankiewicz et al. |
| 2014/0277260 A1 | 9/2014 | Khalil et al. |
| 2014/0371823 A1 | 12/2014 | Mashiach et al. |
| 2015/0018728 A1 | 1/2015 | Gross et al. |
| 2015/0134061 A1 | 5/2015 | Friis et al. |
| 2015/0187320 A1 | 7/2015 | Ren |
| 2016/0270927 A1 | 9/2016 | Zellmer et al. |
| 2017/0007420 A1 | 1/2017 | Stevenson et al. |
| 2017/0157407 A1 | 6/2017 | Zellmer et al. |
| 2017/0246448 A1 | 8/2017 | Lenoble et al. |
| 2018/0078774 A1 | 3/2018 | Strommer et al. |
| 2018/0208992 A1 | 7/2018 | Langevin et al. |
| 2018/0310964 A1 | 11/2018 | Stevenson et al. |
| 2019/0224022 A1 | 7/2019 | Zellmer et al. |
| 2019/0247198 A1 | 8/2019 | Zellmer et al. |
| 2020/0107940 A1 | 4/2020 | Murphy et al. |
| 2020/0108252 A1 | 4/2020 | Zellmer et al. |
| 2020/0206516 A1 | 7/2020 | Zellmer et al. |
| 2020/0297513 A1 | 9/2020 | Zellmer et al. |
| 2020/0352723 A1 | 11/2020 | Jimenez et al. |
| 2021/0128919 A1 | 5/2021 | Zellmer et al. |
| 2023/0000643 A1 | 1/2023 | Zellmer et al. |
| 2024/0268971 A1 | 8/2024 | Zellmer et al. |

FOREIGN PATENT DOCUMENTS

| | | | |
|---|---|---|---|
| JP | 2018521735 A | 8/2018 |
| JP | 2022525384 A | 5/2022 |
| WO | 2013188380 A1 | 12/2013 |
| WO | 2014089299 A3 | 10/2014 |
| WO | 2018208992 A1 | 11/2018 |
| WO | PCTIB2020060276 | 11/2020 |

OTHER PUBLICATIONS

U.S. Appl. No. 16/592,566, filed Oct. 3, 2019, Erik Robert Zellmer.
U.S. Appl. No. 16/825,937, filed Mar. 20, 2020, Erik Robert Zellmer.
Laughner Ji, et al. (2013) A Fully Implantable Pacemaker for the Mouse: From Battery to Wireless Power. PLOS ONE 8(10): e76291. https://doi.org/10.1371/journal.pone.0076291, Oct. 23, 2013.
WIPO European Searching Authority, "PCT2016000482 WO Search and Opinion", Jul. 7, 2016.

* cited by examiner

Side View
130 / 132
110 / 112
120
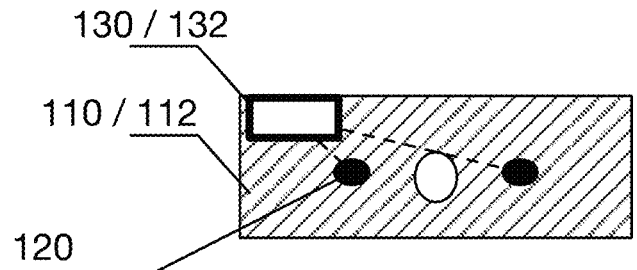
Top View
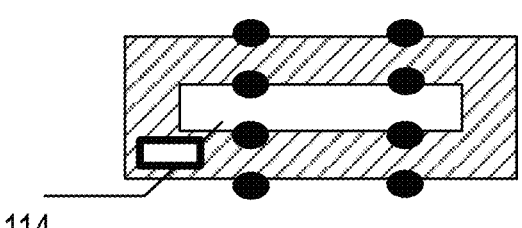
114
FIGURE 1

Side View
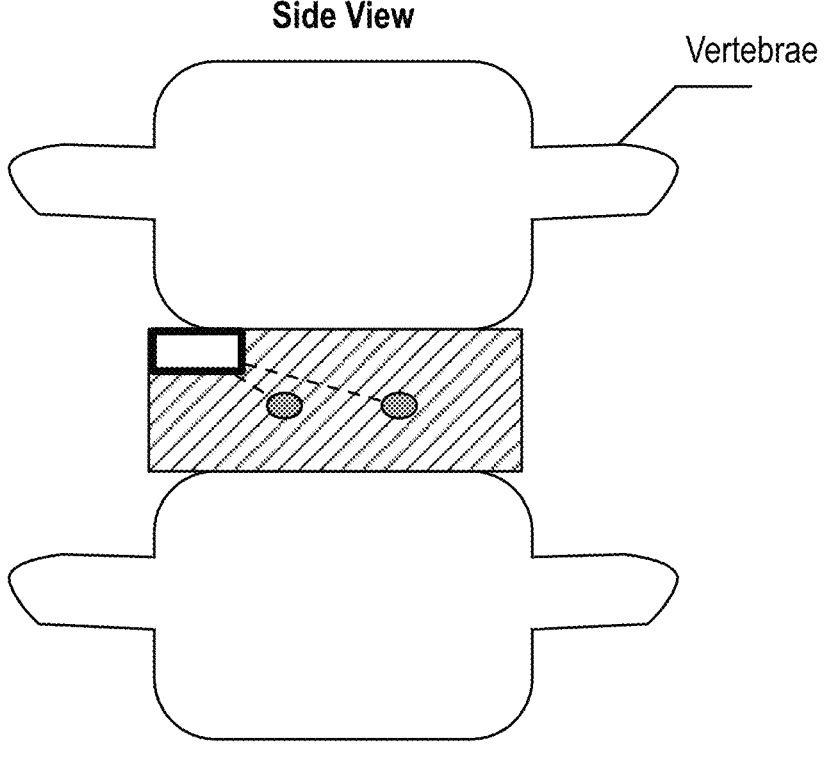
Vertebrae
Top View
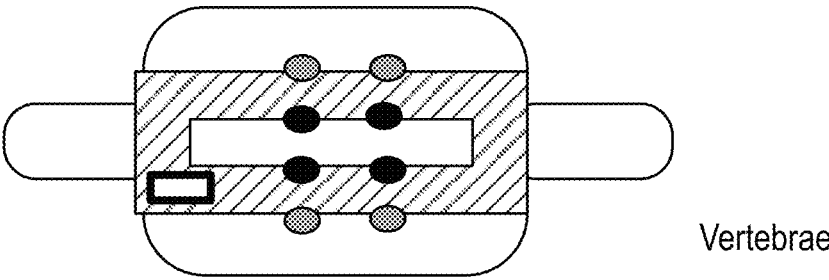
Vertebrae
FIGURE 3

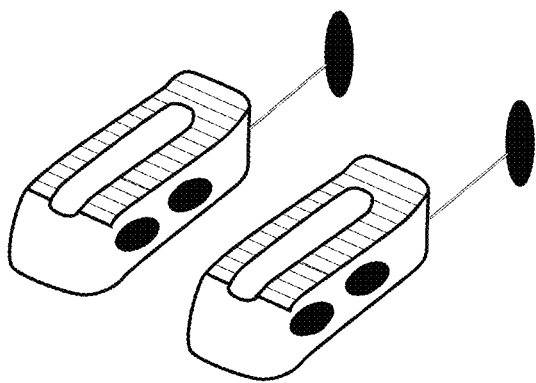
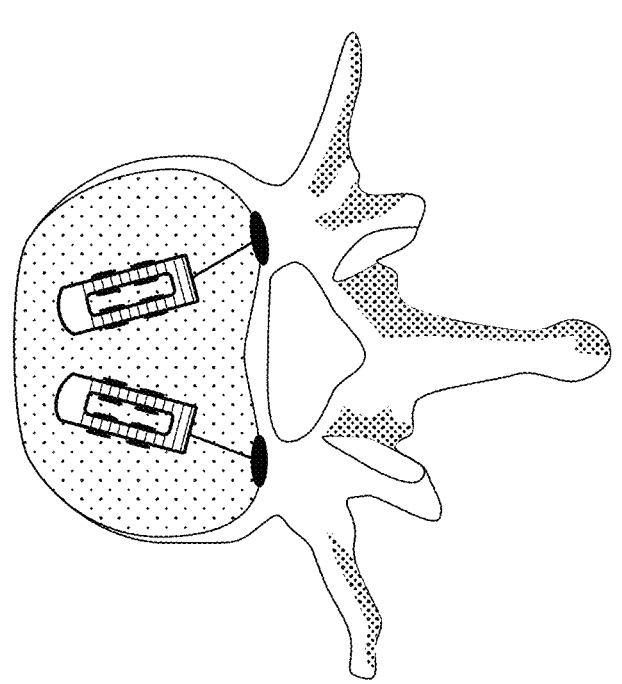
FIGURE 5

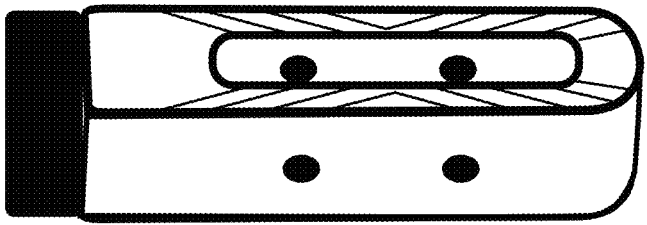
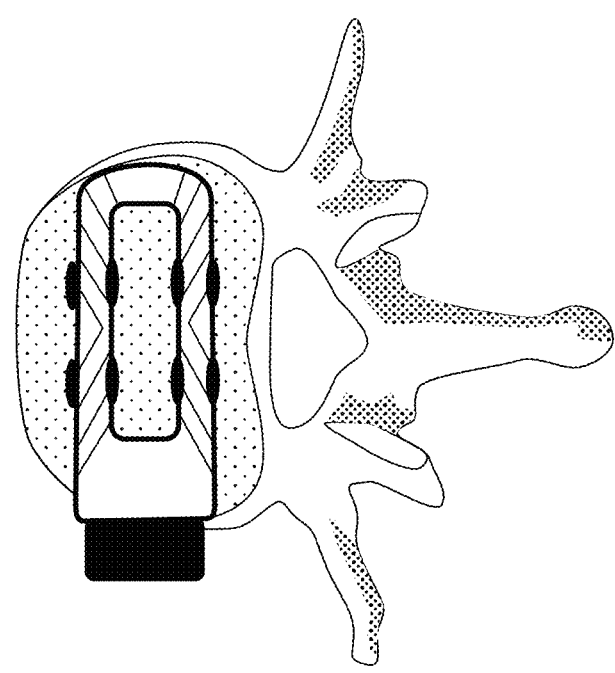
FIGURE 6

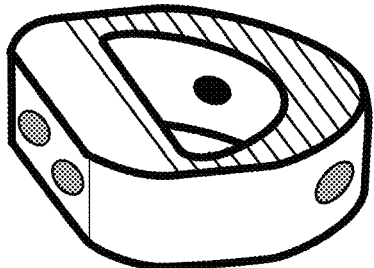
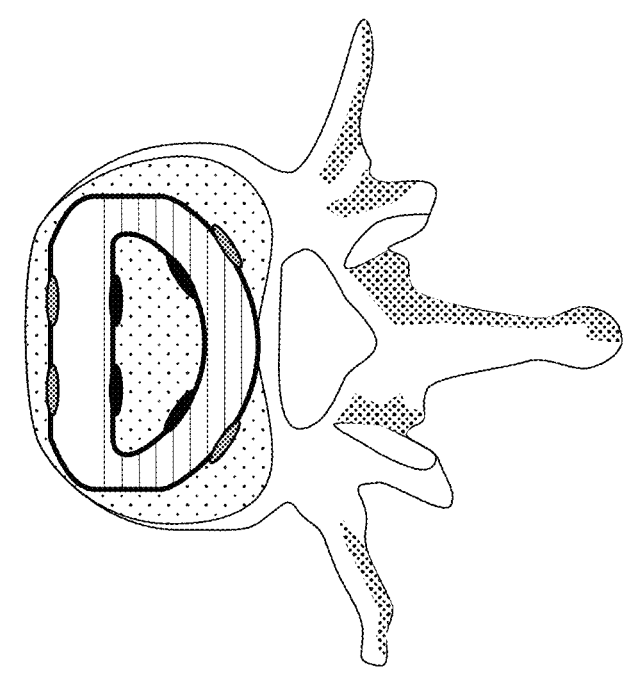
FIGURE 8

VDD

ADC

Connector

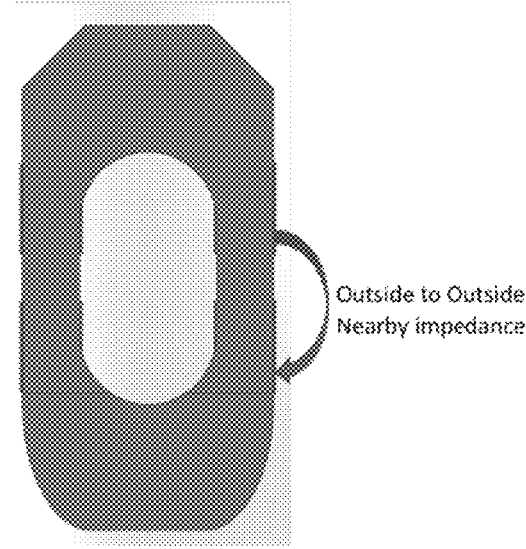
Outside to Outside
Nearby impedance
Each row represents measured impedance data from a
single implant implanted in a sheep
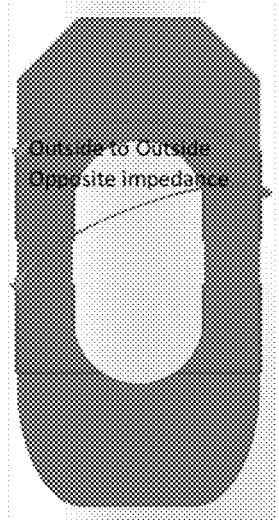
Outside to Outside
Opposite impedance
Each row represents measured impedance data from a
single implant implanted in a sheep
FIGURE 19

Each row represents measured impedance data from a single implant implanted in a sheep
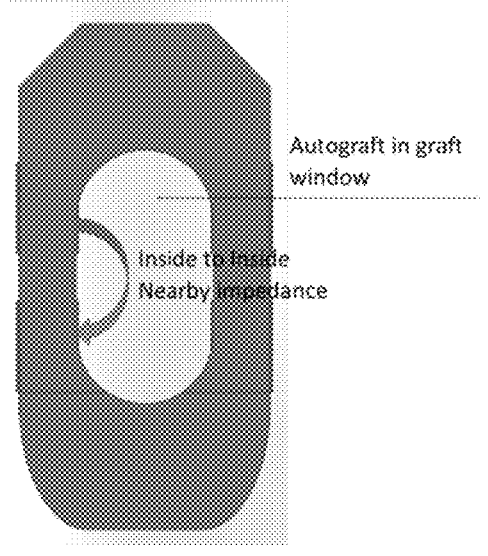
Each row represents measured impedance data from a single implant implanted in a sheep
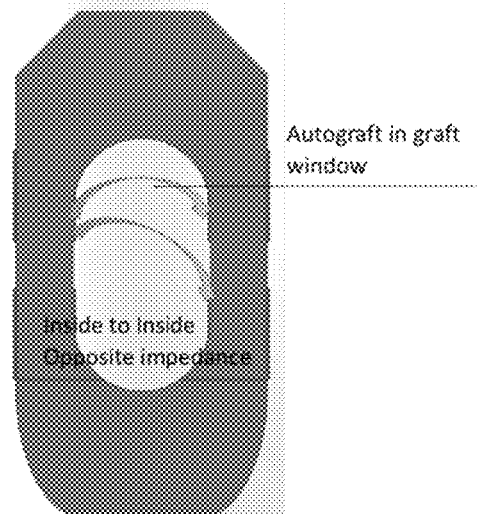
FIGURE 20

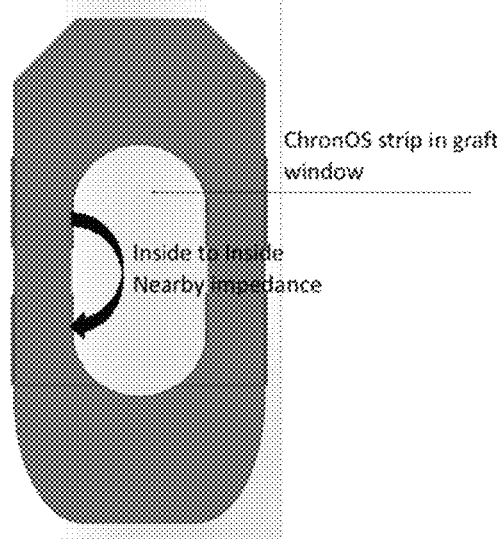

ChronOS strip in graft window

Inside to Inside Nearby impedance

Each row represents measured impedance data from a single implant implanted in a sheep

| InsideToInside impedance (kOhm) Nearby, CHRONOS | |
|---|---|
| | 1.487 |
| | 1.505 |
| | 1.550 |
| | 1.830 |
| | 2.098 |
| | 2.507 |
| Average: | 1.829 |
| StdDev: | 0.4088 |
| Assuming normal distribution | |
| 5th percentile | 1.15822691 |
| 95th percentile | 2.500503898 |

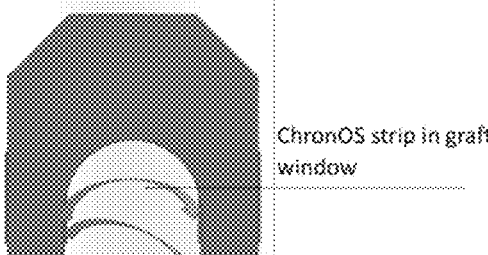

ChronOS strip in graft window

Inside to Inside Opposite impedance

Each row represents measured impedance data from a single implant implanted in a sheep

| InsideToInside impedance (kOhm) Opposite, CHRONOS | |
|---|---|
| | 1.579 |
| | 1.586 |
| | 1.613 |
| | 1.660 |
| | 2.042 |
| | 2.575 |
| Average: | 1.843 |
| StdDev: | 0.4215 |
| Assuming normal distribution | |
| 5th percentile | 1.150060854 |
| 95th percentile | 2.536663291 |

FIGURE 21

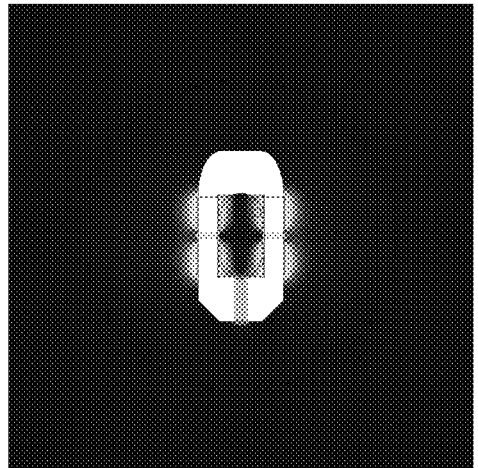
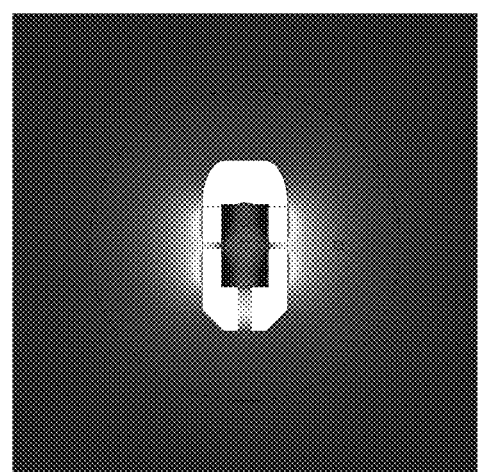
FIGURE 22

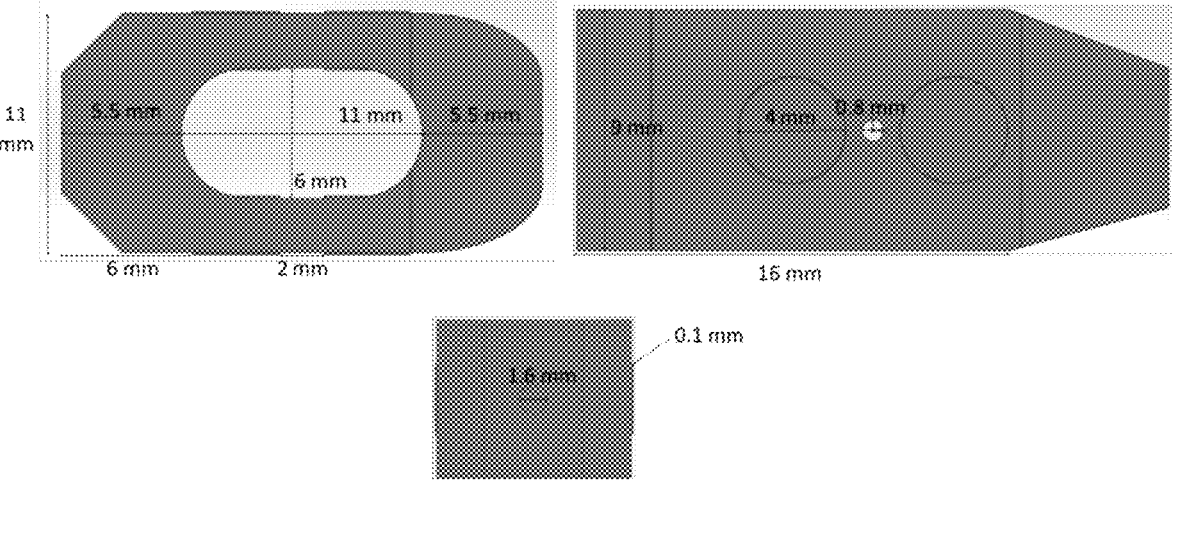
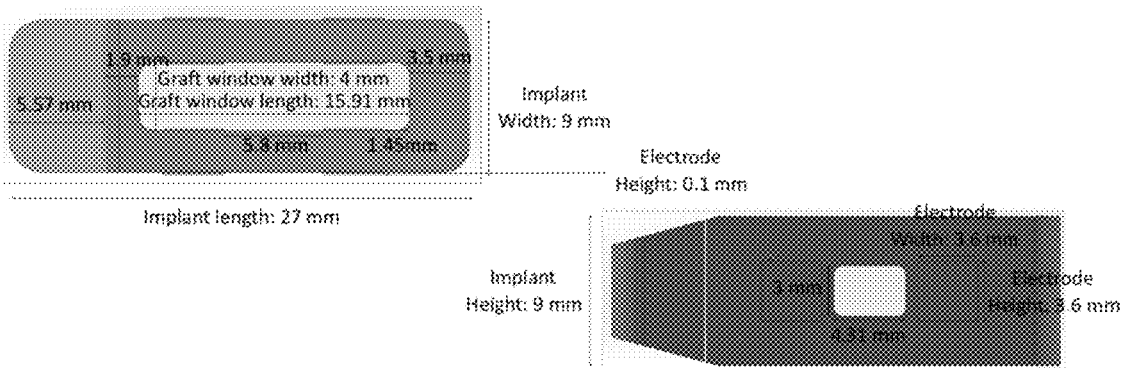
FIGURE 23

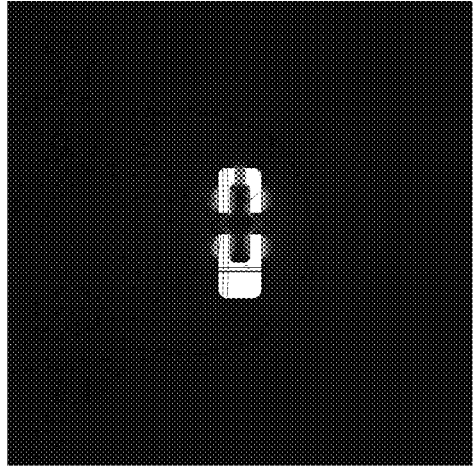
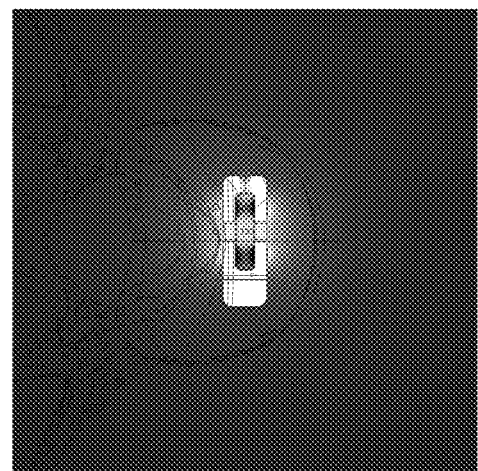
FIGURE 24

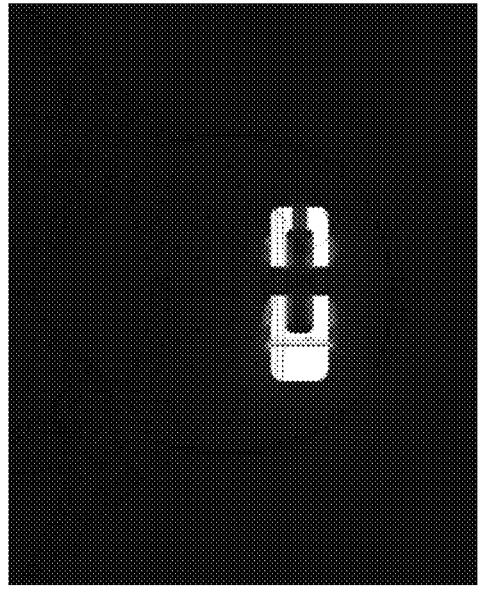
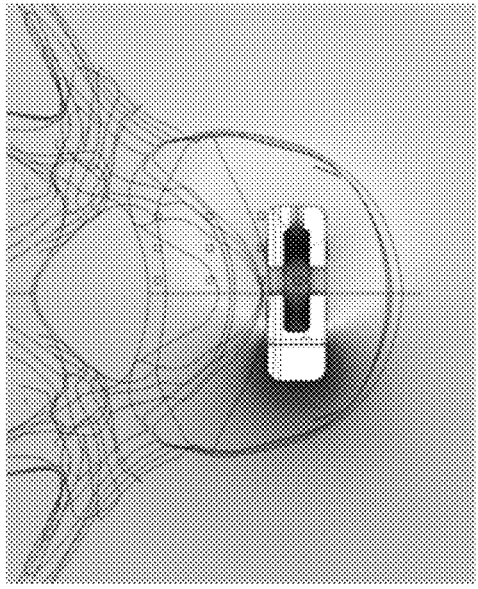
FIGURE 26

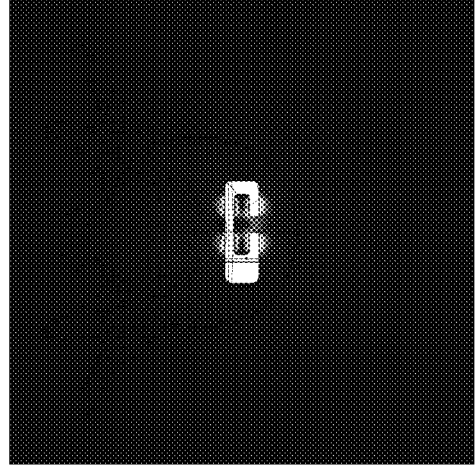
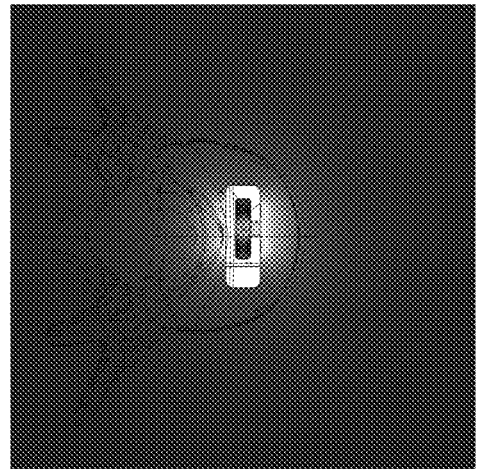
FIGURE 27

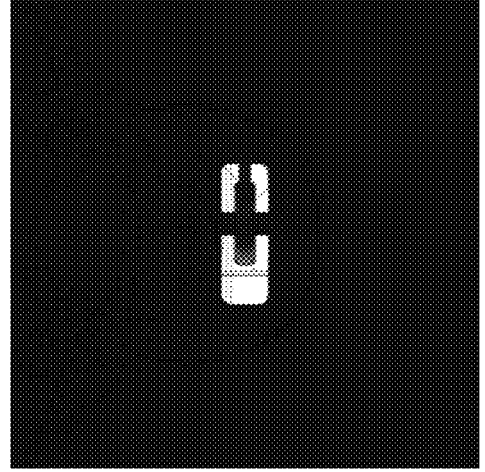
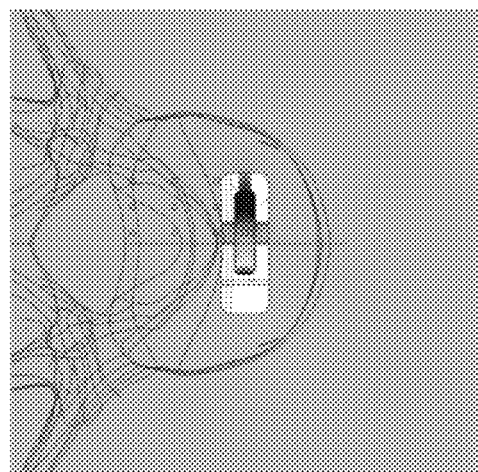
FIGURE 28

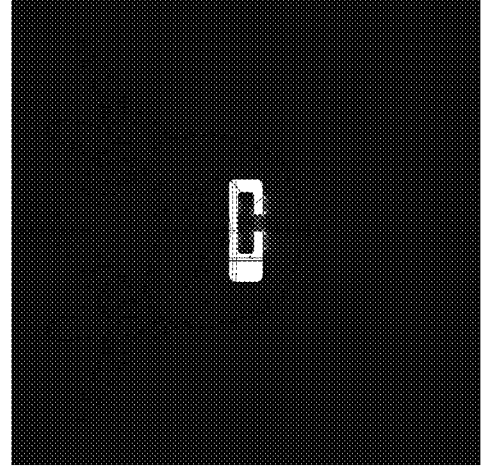
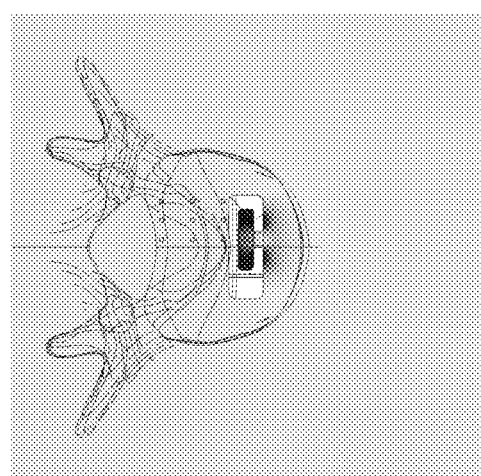
FIGURE 29

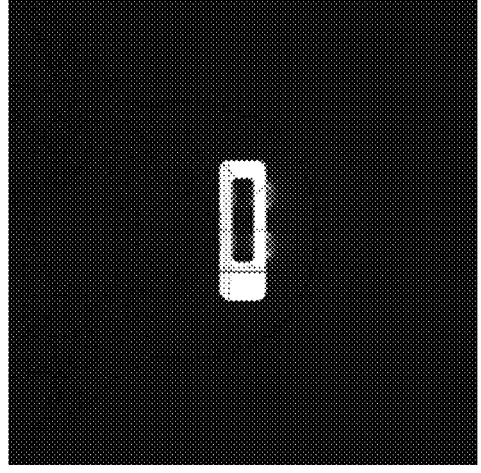
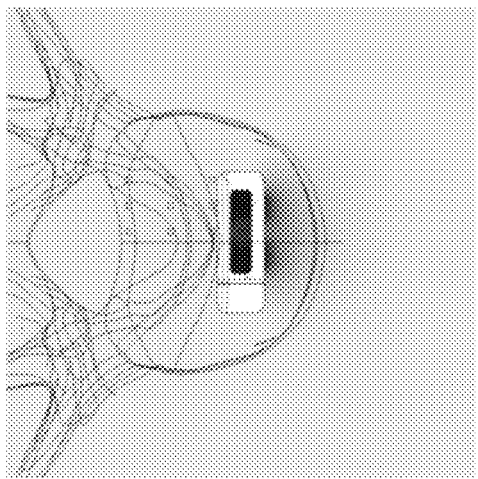
FIGURE 30

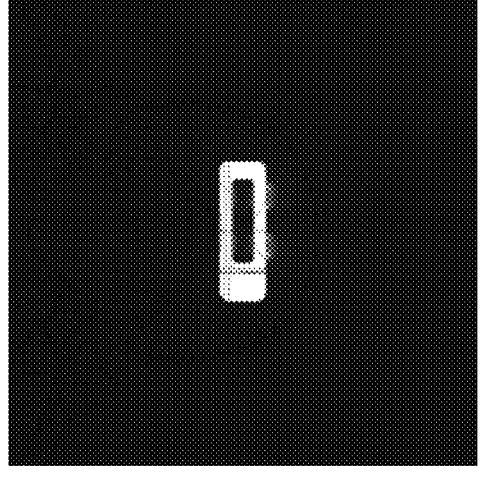
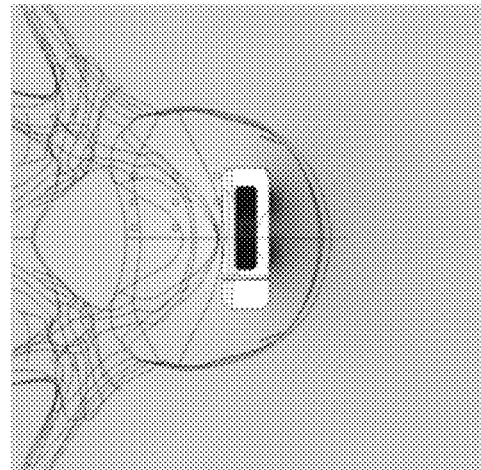
FIGURE 31

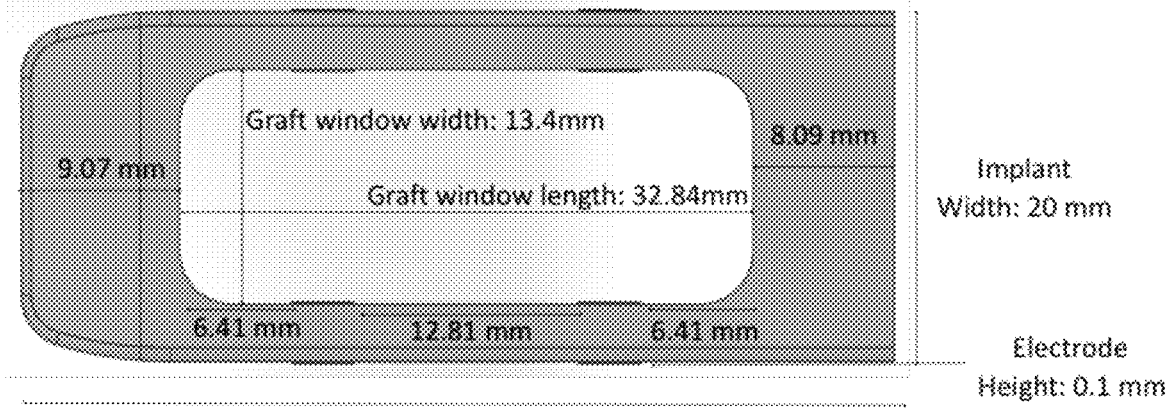
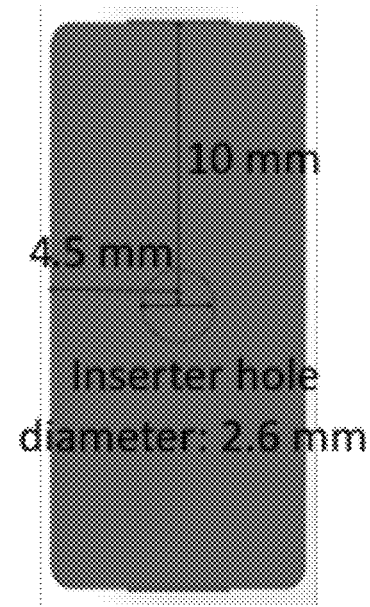
FIGURE 32

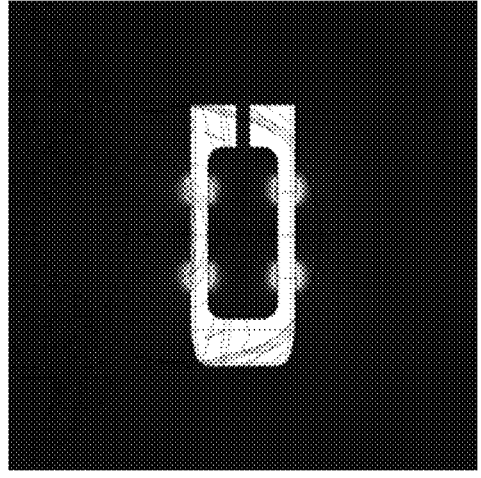
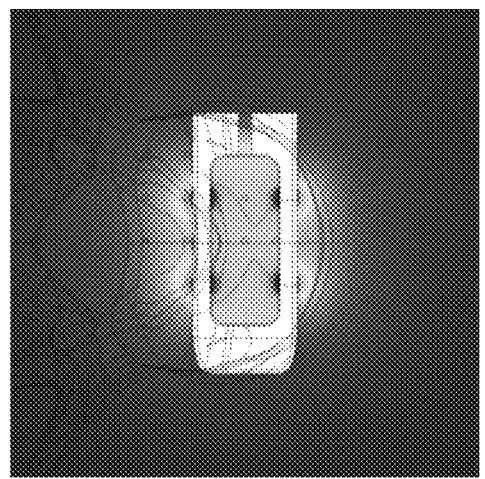
FIGURE 35

| Tissue type (conductivity S/m) | Impedance_I_to_II (kOhm) | Impedance_I_to_III (kOhm) | Impedance_I_to_IV (kOhm) | Impedance_I_to_V (kOhm) |
|---|---|---|---|---|
| Low Impedance Autograft (0.6) | 0.478927203 | 0.559284116 | 0.825083508 | 0.844594595 |
| Average Autograft (0.261) | 0.868055556 | 0.9765625 | 1.024990384 | 1.054852321 |
| High Impedance Autograft (0.17) | 1.184834123 | 1.302083333 | 1.184834123 | 1.219512195 |
| Low impedance bone plug (0.136) | 1.38121547 | 1.497005988 | 1.282051282 | 1.322751323 |
| Bone from plug estimation (0.067) | 2.192983456 | 2.293577982 | 1.672852349 | 1.724137931 |
| Average impedance bone plug (0.042) | 2.843873535 | 2.929376254 | 1.984126984 | 2.049180328 |
| High Impedance bone plug (0.01) | 4.934996623 | 4.909922561 | 2.887171889 | 3.065727982 |

Impedance, I to II

Impedance, I to III

Impedance, I to IV

Impedance, I to V

Electrode
Width: 9mm

Electrode
Height: 6.3 mm 12.63mm                 7.11mm

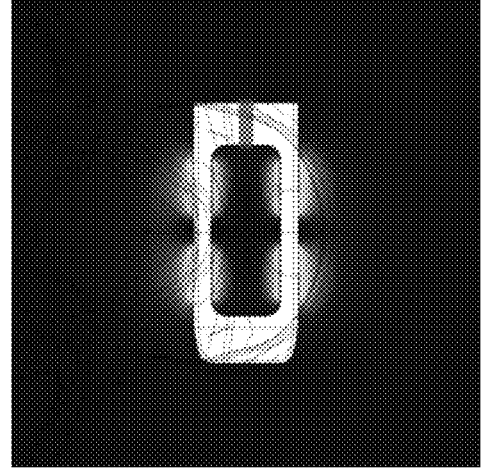
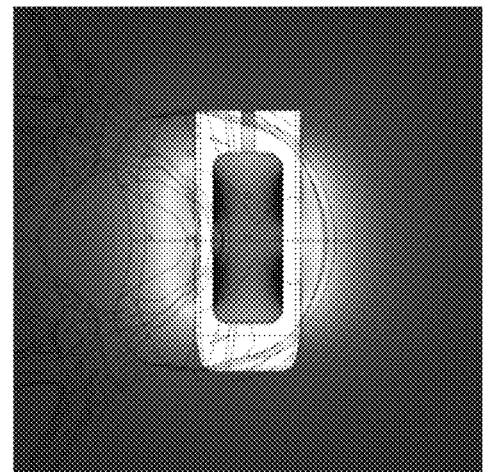
FIGURE 38

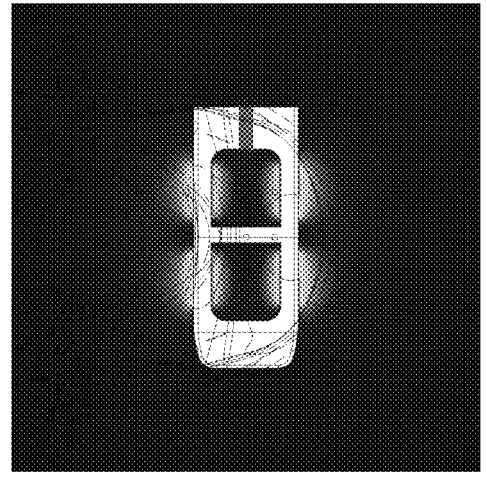
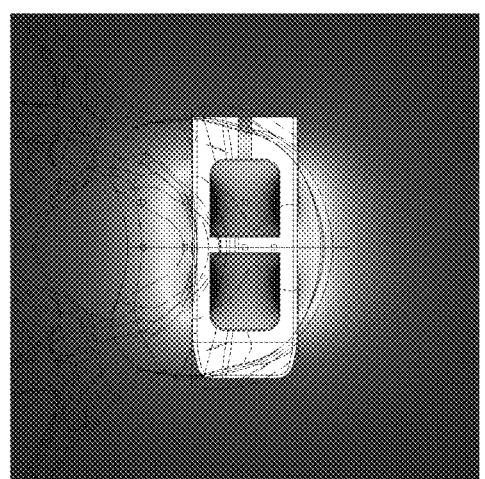
FIGURE 39

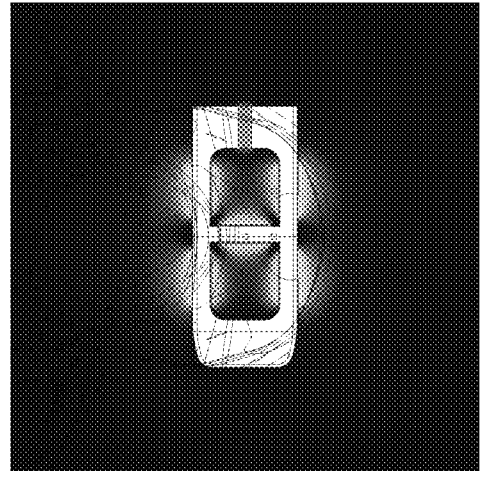
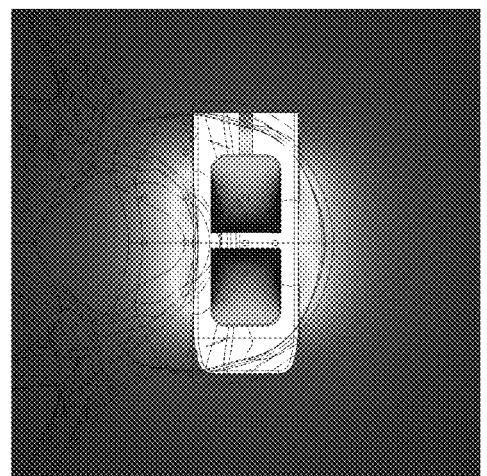
FIGURE 40

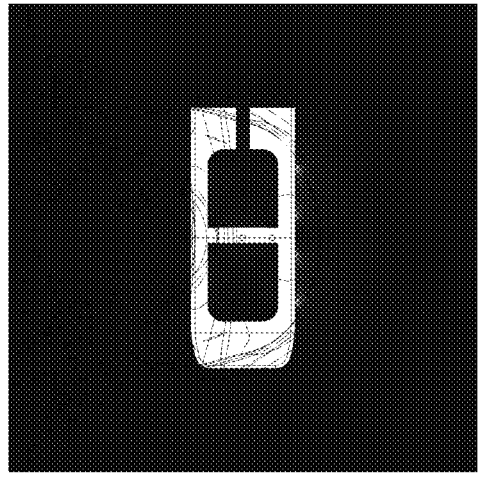
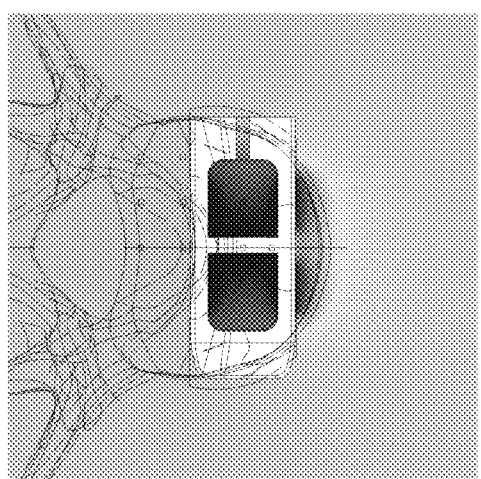
FIGURE 41

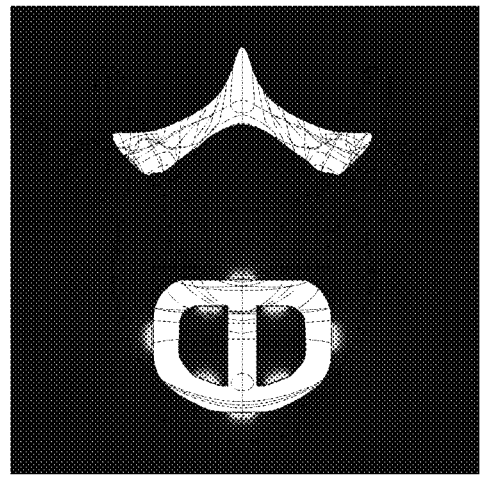
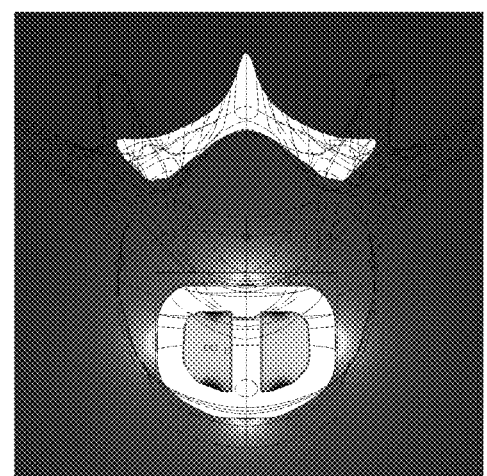
FIGURE 42

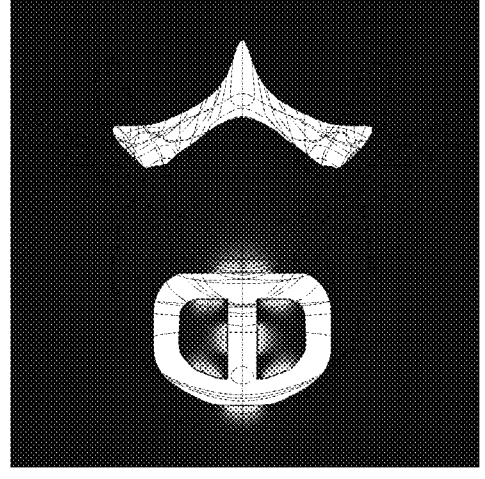
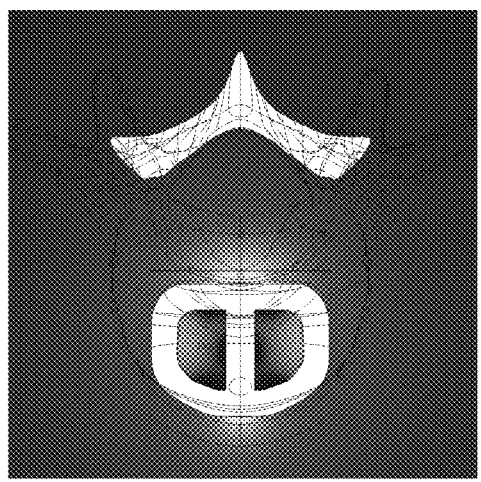
FIGURE 43

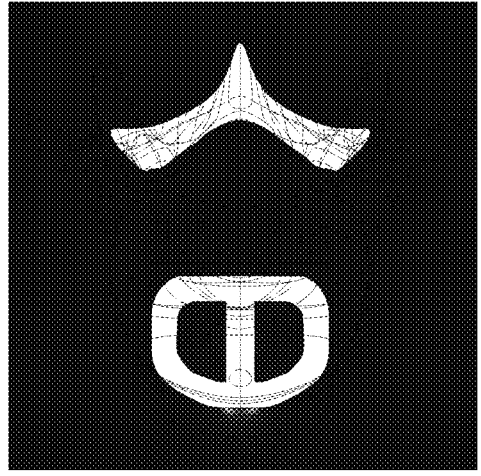
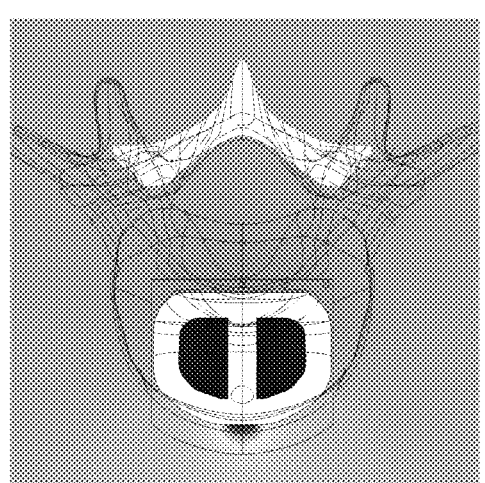
FIGURE 44

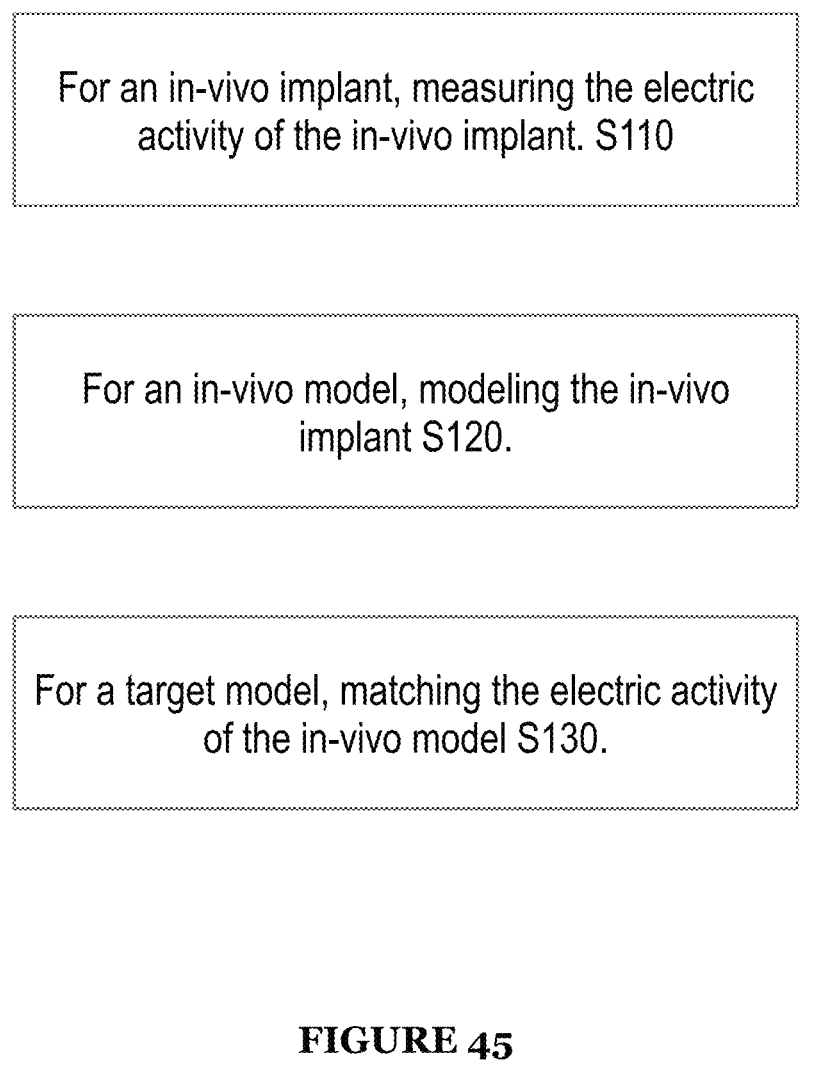

For an in-vivo implant, measuring the electric activity of the in-vivo implant. S110

For an in-vivo model, modeling the in-vivo implant S120.

For a target model, matching the electric activity of the in-vivo model S130.

FIGURE 45

Dose-Response curve SmartFuse (subtractive difference in BV/TV between stimulated and control levels)
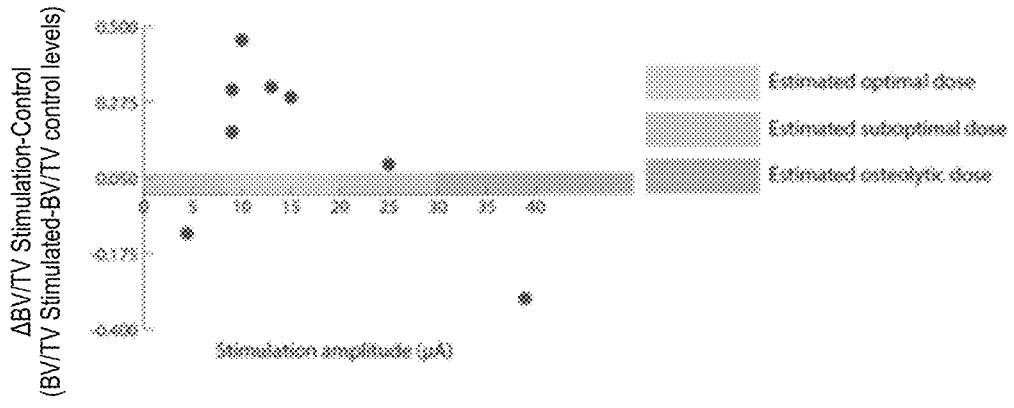
Dose-Response curve SmartFuse (multiplicative difference in BV/TV between stimulated and control levels)
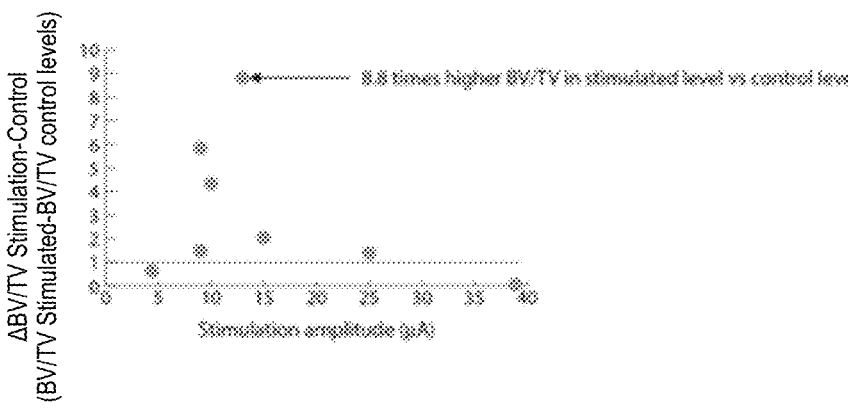
46

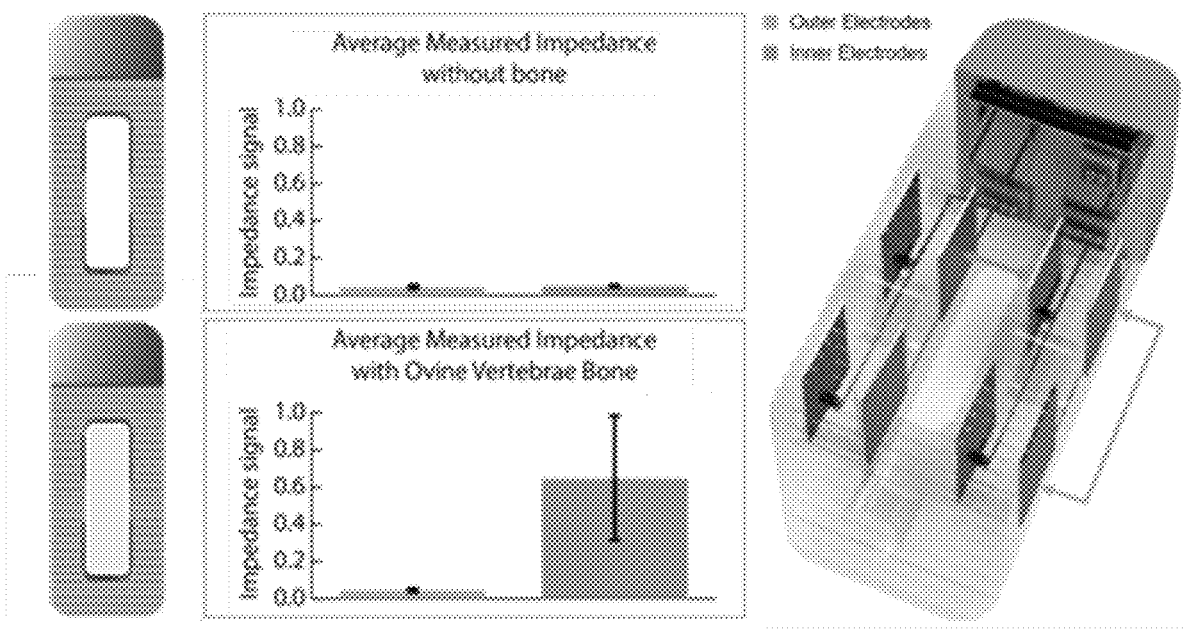
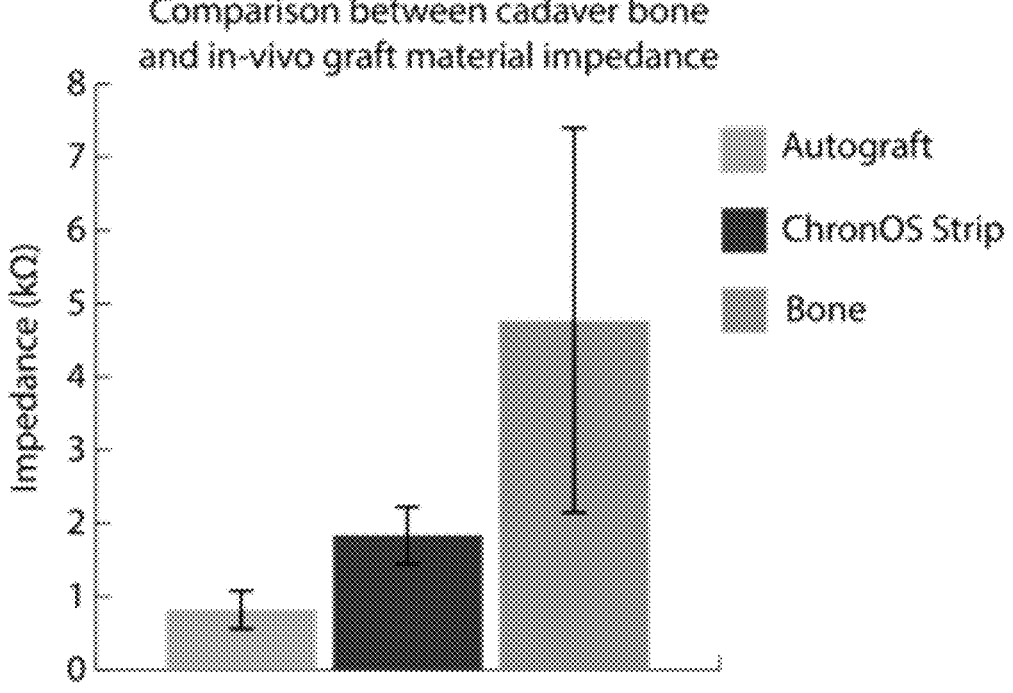
FIGURE 47

Table 1

| # | A (A*m) | A (nA*mm) | B (A*m) | B (nA*mm) | C (A*m) | C (nA*mm) | D (A*m) | D (nA*mm) | E (A*m) | E (nA*mm) | F (A*m) | F (nA*mm) |
|---|---------|-----------|---------|-----------|---------|-----------|---------|-----------|---------|-----------|---------|-----------|
| 1 | 7.22E-11 | 72 | 3.19E-11 | 32 | 1.63E-12 | 2 | 2.10E-12 | 2 | 1.31E-12 | 1 | 6.36E-11 | 64 |
| 2 | 5.64E-11 | 56 | 2.59E-11 | 26 | 3.90E-12 | 4 | 4.12E-12 | 4 | 3.99E-12 | 4 | 4.68E-11 | 47 |
| 3 | 2.36E-11 | 24 | 1.53E-11 | 15 | 5.85E-12 | 6 | 6.05E-12 | 6 | 6.89E-12 | 7 | 1.93E-11 | 19 |
| 4 | 1.60E-11 | 16 | 1.07E-11 | 11 | 5.80E-12 | 6 | 6.04E-12 | 6 | 8.18E-12 | 8 | 1.58E-11 | 16 |
| 5 | 8.34E-12 | 8 | 7.59E-12 | 8 | 5.59E-12 | 6 | 5.77E-12 | 6 | 7.30E-12 | 7 | 1.49E-11 | 15 |
| 6 | 6.13E-12 | 6 | 6.09E-12 | 6 | 5.24E-12 | 5 | 5.35E-12 | 5 | 5.06E-12 | 5 | 1.12E-11 | 11 |
| 7 | 4.85E-12 | 5 | 4.98E-12 | 5 | 4.78E-12 | 5 | 4.90E-12 | 5 | 4.30E-12 | 4 | 7.46E-12 | 7 |

Table 2

| # | A (A*m) | A (nA*mm) | B (A*m) | B (nA*mm) | C (A*m) | C (nA*mm) | D (A*m) | D (nA*mm) | E (A*m) | E (nA*mm) | F (A*m) | F (nA*mm) |
|---|---------|-----------|---------|-----------|---------|-----------|---------|-----------|---------|-----------|---------|-----------|
| 1 | 1.44E-10 | 144 | 6.39E-11 | 64 | 3.25E-12 | 3 | 4.20E-12 | 4 | 2.62E-12 | 3 | 1.27E-10 | 127 |
| 2 | 1.13E-10 | 113 | 5.18E-11 | 52 | 7.80E-12 | 8 | 8.24E-12 | 8 | 7.98E-12 | 8 | 9.36E-11 | 94 |
| 3 | 4.72E-11 | 47 | 3.05E-11 | 31 | 1.17E-11 | 12 | 1.21E-11 | 12 | 1.38E-11 | 14 | 3.86E-11 | 39 |
| 4 | 3.21E-11 | 32 | 2.13E-11 | 21 | 1.16E-11 | 12 | 1.21E-11 | 12 | 1.64E-11 | 16 | 3.17E-11 | 32 |
| 5 | 1.67E-11 | 17 | 1.52E-11 | 15 | 1.12E-11 | 11 | 1.15E-11 | 12 | 1.46E-11 | 16 | 2.99E-11 | 30 |
| 6 | 1.23E-11 | 12 | 1.22E-11 | 12 | 1.05E-11 | 11 | 1.07E-11 | 11 | 1.01E-11 | 10 | 2.24E-11 | 22 |
| 7 | 9.71E-12 | 10 | 9.97E-12 | 10 | 9.56E-12 | 10 | 9.80E-12 | 10 | 8.61E-12 | 9 | 1.49E-11 | 15 |

Table 3

| # | A (A*m) | A (nA*mm) | B (A*m) | B (nA*mm) | C (A*m) | C (nA*mm) | D (A*m) | D (nA*mm) | E (A*m) | E (nA*mm) | F (A*m) | F (nA*mm) |
|---|---------|-----------|---------|-----------|---------|-----------|---------|-----------|---------|-----------|---------|-----------|
| 1 | 2.89E-10 | 289 | 1.28E-10 | 128 | 6.51E-12 | 7 | 8.41E-12 | 8 | 5.24E-12 | 5 | 2.54E-10 | 254 |
| 2 | 2.25E-10 | 225 | 1.04E-10 | 104 | 1.56E-11 | 16 | 1.65E-11 | 16 | 1.60E-11 | 16 | 1.87E-10 | 187 |
| 3 | 9.44E-11 | 94 | 6.11E-11 | 61 | 2.34E-11 | 23 | 2.42E-11 | 23 | 2.76E-11 | 28 | 7.72E-11 | 77 |
| 4 | 6.42E-11 | 64 | 4.27E-11 | 43 | 2.32E-11 | 23 | 2.42E-11 | 23 | 3.27E-11 | 33 | 6.33E-11 | 63 |
| 5 | 5.34E-11 | 53 | 3.04E-11 | 30 | 2.23E-11 | 22 | 2.31E-11 | 23 | 2.92E-11 | 29 | 5.98E-11 | 60 |
| 6 | 2.45E-11 | 25 | 2.44E-11 | 24 | 2.10E-11 | 21 | 2.14E-11 | 21 | 2.02E-11 | 20 | 4.47E-11 | 45 |
| 7 | 1.94E-11 | 19 | 1.99E-11 | 20 | 1.91E-11 | 20 | 1.96E-11 | 19 | 1.72E-11 | 17 | 2.98E-11 | 30 |

Posterior Side

Spinal Cord

Right Side

Body

Left Side

Anterior Side

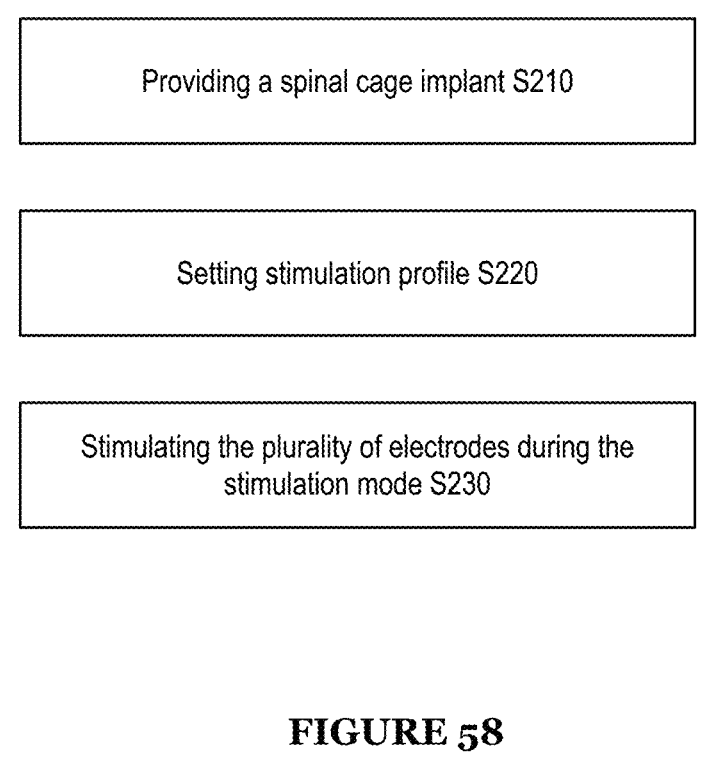

Providing a spinal cage implant S210

Setting stimulation profile S220

Stimulating the plurality of electrodes during the
stimulation mode S230

FIGURE 58

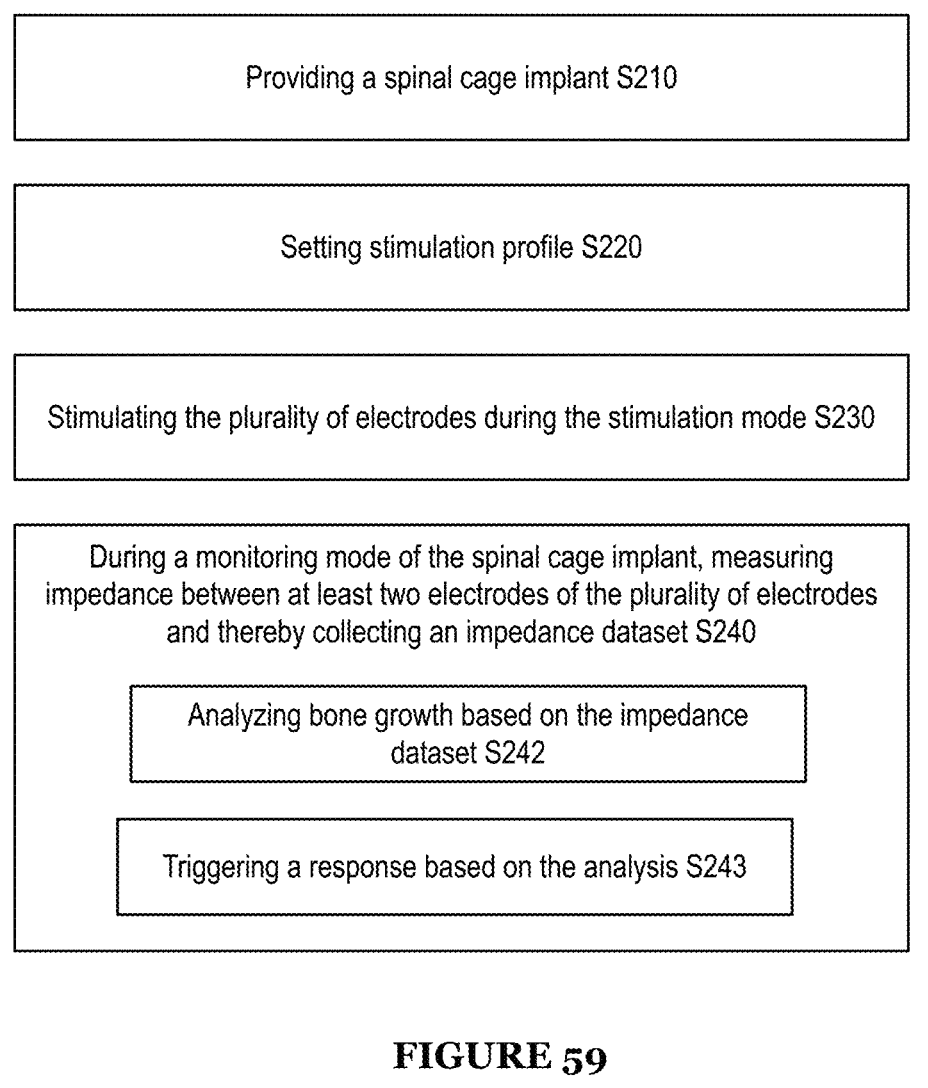

Providing a spinal cage implant S210

Setting stimulation profile S220

Stimulating the plurality of electrodes during the stimulation mode S230

During a monitoring mode of the spinal cage implant, measuring impedance between at least two electrodes of the plurality of electrodes and thereby collecting an impedance dataset S240

Analyzing bone growth based on the impedance dataset S242

Triggering a response based on the analysis S243

FIGURE 59

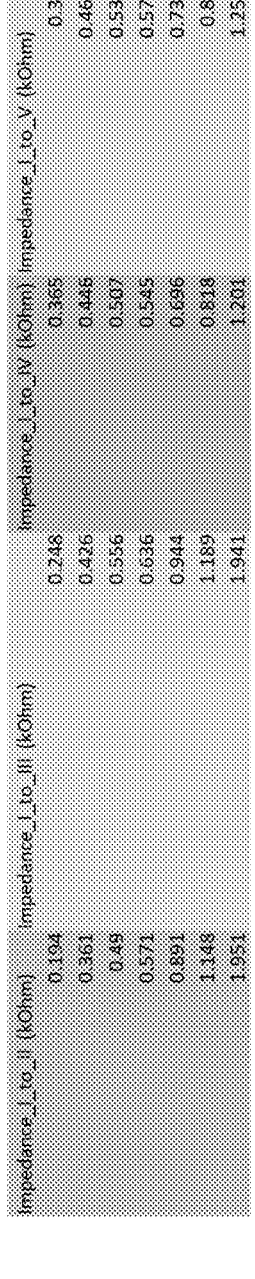
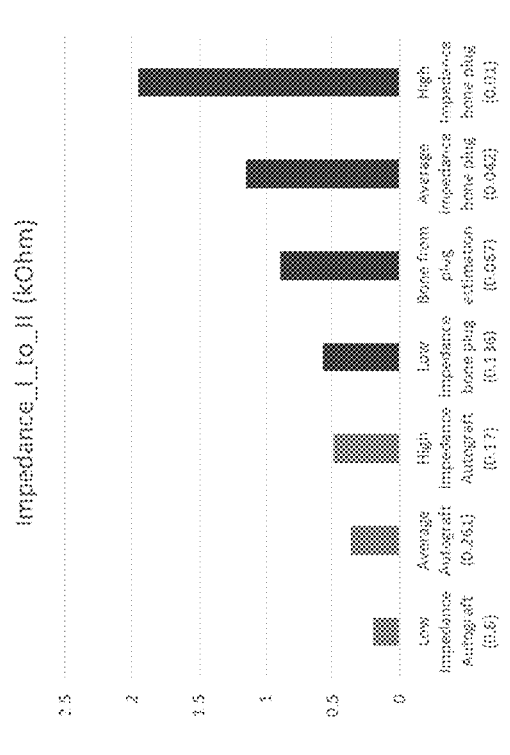
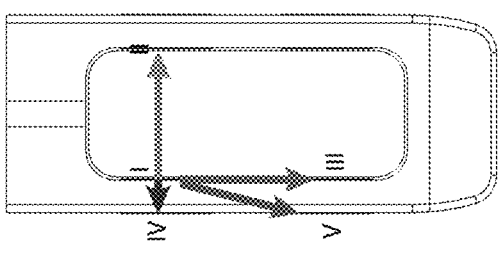
FIGURE 61

9 uA

| A A/m^2 | (uA/cm^2) | B A/m^2 | (uA/cm^2) | C A/m^2 | (uA/cm^2) | D A/m^2 | (uA/cm^2) | | |
|---|---|---|---|---|---|---|---|---|---|
| 1 | 5.08E-02 | 5.1 | 1.01E-02 | 1.0 | 1.38E-02 | 1.5 | 5.82E-03 | 0.6 | 2.0 |
| 2 | 5.48E-02 | 5.5 | 2.81E-02 | 2.8 | 2.70E-02 | 2.7 | 2.08E-02 | 2.1 | 3.3 |
| 3 | 4.11E-02 | 4.1 | 3.01E-02 | 3.0 | 3.15E-02 | 3.2 | 2.32E-02 | 2.3 Next to Endplate | 3.1 |
| 4 | 2.89E-02 | 2.8 | 2.38E-02 | 2.3 | 2.42E-02 | 2.4 | 1.99E-02 | 2.0 | 2.4 |

15 uA

| A A/m^2 | (uA/cm^2) | B A/m^2 | (uA/cm^2) | C A/m^2 | (uA/cm^2) | D A/m^2 | (uA/cm^2) | | |
|---|---|---|---|---|---|---|---|---|---|
| 1 | 8.47E-02 | 8.5 | 1.68E-02 | 1.7 | 2.46E-02 | 2.5 | 9.70E-03 | 1.0 | 3.4 |
| 2 | 9.14E-02 | 9.1 | 4.68E-02 | 4.7 | 4.50E-02 | 4.5 | 3.47E-02 | 3.5 | 5.4 |
| 3 | 6.88E-02 | 6.9 | 5.01E-02 | 5.0 | 5.25E-02 | 5.3 | 3.86E-02 | 3.9 Next to Endplate | 5.2 |
| 4 | 4.67E-02 | 4.7 | 3.79E-02 | 3.8 | 4.04E-02 | 4.0 | 3.32E-02 | 3.3 | 4.0 |

5 uA

| A A/m^2 | (uA/cm^2) | B A/m^2 | (uA/cm^2) | C A/m^2 | (uA/cm^2) | D A/m^2 | (uA/cm^2) | | |
|---|---|---|---|---|---|---|---|---|---|
| 1 | 3.83E-02 | 2.8 | 5.61E-03 | 0.6 | 8.20E-03 | 0.8 | 3.23E-03 | 0.3 | 1.1 |
| 2 | 3.05E-02 | 3.0 | 1.56E-02 | 1.6 | 1.50E-02 | 1.5 | 1.16E-02 | 1.2 | 1.8 |
| 3 | 2.29E-02 | 2.3 | 1.67E-02 | 1.7 | 1.75E-02 | 1.8 | 1.29E-02 | 1.3 Next to Endplate | 1.7 |
| 4 | 1.56E-02 | 1.6 | 1.26E-02 | 1.3 | 1.35E-02 | 1.3 | 1.11E-02 | 1.1 | 1.3 |

Likely too low to be efficient

This appears to not be enough (lower than threshold)

25 uA

| A A/m^2 | (uA/cm^2) | B A/m^2 | (uA/cm^2) | C A/m^2 | (uA/cm^2) | D A/m^2 | (uA/cm^2) | | |
|---|---|---|---|---|---|---|---|---|---|
| 1 | 1.41E-01 | 14.1 | 2.80E-01 | 2.8 | 4.10E-03 | 2.8 | 1.62E-02 | 4.1 | 5.7 |
| 2 | 1.52E-01 | 15.2 | 7.81E-02 | 7.8 | 7.50E-02 | 7.5 | 5.78E-02 | 7.5 | 9.1 |
| 3 | 1.14E-01 | 11.4 | 8.35E-02 | 8.3 | 8.75E-02 | 8.8 | 6.48E-02 | 8.8 Next to Endplate | 8.7 |
| 4 | 7.78E-02 | 7.8 | 6.32E-02 | 6.3 | 6.73E-02 | 6.7 | 5.53E-02 | 6.7 | 6.6 |

Likely too high to be efficient

This appears to be safe

40 uA

| A A/m^2 | (uA/cm^2) | B A/m^2 | (uA/cm^2) | C A/m^2 | (uA/cm^2) | D A/m^2 | (uA/cm^2) | | |
|---|---|---|---|---|---|---|---|---|---|
| 1 | 2.26E-01 | 22.6 | 4.36E-02 | 4.5 | 6.56E-02 | 6.8 | 2.59E-02 | 6.8 | 9.1 |
| 2 | 2.44E-01 | 24.4 | 1.25E-01 | 12.5 | 1.20E-01 | 12.0 | 9.24E-02 | 12.0 | 14.5 |
| 3 | 1.83E-01 | 18.3 | 1.34E-01 | 13.4 | 1.40E-01 | 14.0 | 1.03E-01 | 14.0 Next to Endplate | 14.0 |
| 4 | 1.24E-01 | 12.4 | 1.01E-01 | 10.1 | 1.08E-01 | 10.8 | 8.85E-02 | 10.8 | 10.5 |

FIGURE 62

SYSTEM AND METHOD FOR SCALING ORTHOPEDIC IMPLANT STIMULATION

CROSS-REFERENCE TO RELATED APPLICATIONS

This application claims the benefit of U.S. Provisional Application No. 63/166,143, filed on 25 Mar. 2021, which is incorporated in its entirety by this reference.

TECHNICAL FIELD

This invention relates generally to the field of spinal implant orthopedic therapy, and more specifically to a new and useful system and method for scaling orthopedic implant stimulation.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Many contemporary spinal fusion hardware and biologics include designs to address the problems associated with non-unions, with little regard to heterotopic ossification. For example, commonly used biologics, particularly recombinant human bone morphogenetic protein (rhBMP-2), have been used to reduce non-fusion rates by increasing bone formation in the fusion space and the volume surrounding it. While clinically proven to decrease non-unions, numerous studies have shown that the biologic causes a host of side effects including but not limited to cancer, tissue swelling, growth of benign tissue, teratogenicity, pathological heterotopic ossification, nerve injury and spinal cord injury. While not all side effects caused by rhBMP-2 are related to heterotopic ossification, many are. As such, the biologic represents an illustrating example of how, nonspecific, unguided osteoinduction can be harmful to a patient and the delicate balance between increasing fusion rates and avoiding heterotopic ossification.

A second method utilized in reducing non-union rates is electrical stimulation. When mechanical stress is exerted on bone, an electric field is created. In the body, this electrical field constitutes a signal causing a physiological response resulting in osteoinduction or osteolysis. Consequently, it is possible to cause osteoinduction or osteolysis by introducing an electrical field in the volume within and surrounding a segment of bone. In volumes where the current density is above a certain threshold, osteoinduction is achieved if the polarity of the field in the region is electronegative while bone in regions where the field is electropositive undergoes osteolysis. However, in many implementations there is a lack of precise control over the regions of electrical stimulation.

As the field of spinal fusion is such a unique and evasive field for patients, actual testing of effective treatments is somewhat prohibitive; wherein testing mistakes in humans is completely unacceptable. On the other hand, bone tissue is very similar in a significant population of mammals wherein in-vivo animal experiments may provide useful information for actual human treatment.

Thus, there is a need to create a new and useful system and method for improved stimulation implant. This invention provides such a new and useful system and method.

BRIEF DESCRIPTION OF THE FIGURES

FIG. 1 is a schematic of a system of a preferred embodiment;

FIG. 3 is a schematic of an implanted system;

FIG. 5 is an illustration of a PLIF cage;

FIG. 6 is an illustration of a lateral cage;

FIG. 8 is an illustration of an ALIF cage;

FIG. 19 is an impedance measurement example;

FIG. 20 is an impedance measurement example;

FIG. 21 is an impedance measurement example;

FIG. 22 is a set of heat graphs showing electrical stimulation around an in-vivo implant;

FIG. 23 are schematics for TLIF cages;

FIG. 24 is a set heat graphs showing electrical stimulation around a TLIF cage model;

FIG. 26 is a set of heat graphs showing electrical stimulation around a TLIF cage model;

FIG. 27 is a set of heat graphs showing electrical stimulation around a TLIF cage model;

FIG. 28 is a set of heat graphs showing electrical stimulation around a TLIF cage model;

FIG. 29 is a set of heat graphs showing electrical stimulation around a TLIF cage model;

FIG. 30 is a set of heat graphs showing electrical stimulation around a TLIF cage model;

FIG. 31 is a set of heat graphs showing electrical stimulation around a TLIF cage model;

FIG. 32 is a schematic diagram of a model lateral cage;

FIG. 35 is a set of heat graphs showing electrical stimulation around a lateral cage model;

FIG. 38 is a set of heat graphs showing electrical stimulation around a lateral cage model;

FIG. 39 is a set of heat graphs showing electrical stimulation around a lateral cage model;

FIG. 40 is a set of heat graphs showing electrical stimulation around a lateral cage model;

FIG. 41 is a set of heat graphs showing electrical stimulation around a lateral cage model;

FIG. 42 is a set of heat graphs showing electrical stimulation around an ALIF cage model;

FIG. 43 is a set of heat graphs showing electrical stimulation around an ALIF cage model;

FIG. 44 is a set of heat graphs showing electrical stimulation around an ALIF cage model;

FIG. 45 is a method of a preferred embodiment;

FIG. 46 is a graph of a dose response curve from an in-vivo TLIF cage;

FIG. 47 is a graph of cadaver tissue measurement within a TLIF cage;

Figure 55:
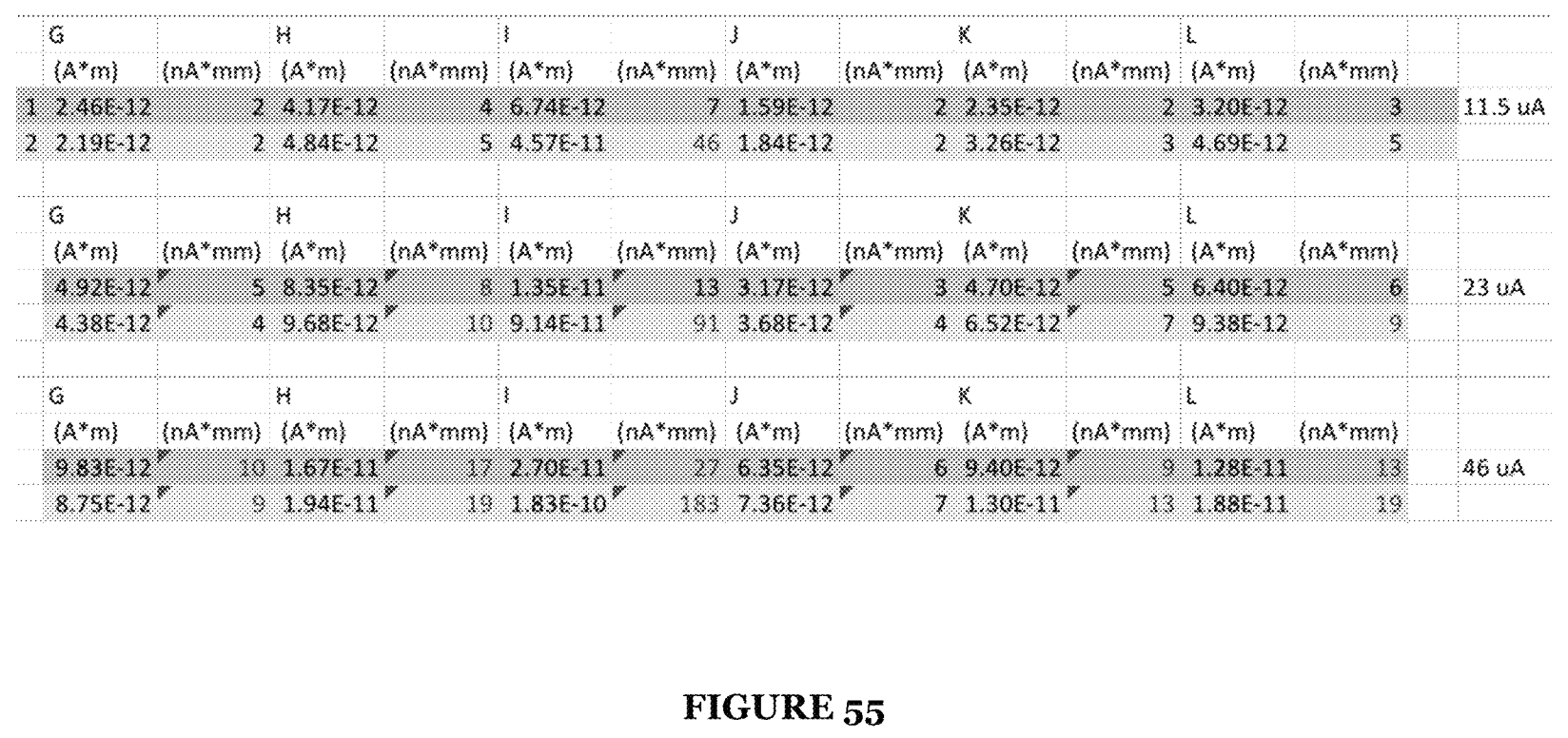

FIGS. 54 and 55 are stimulation data for an ALIF cage implant model.

FIG. 58 is a flow diagram of a method for operating an implant.

FIG. 59 is a flow diagram of a method for operating an implant with a monitoring mode.

FIG. 61 are impedance measurements for sample bone grafts over an exemplary cage.

FIG. 62 is a chart of implant data for stimulation metric thresholds.

DESCRIPTION OF THE EMBODIMENTS

Figure 2:
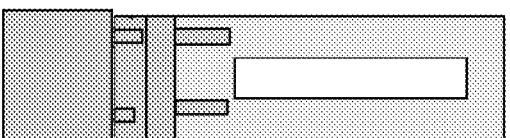
FIG. 2 is a second schematic of a system of a preferred embodiment.

The following description of the embodiments of the invention is not intended to limit the invention to these embodiments but rather to enable a person skilled in the art to make and use this invention.

1. Overview

A system and method for enhanced orthopedic implant stimulation functions to enable calibrated stimulation and/or monitoring by a target orthopedic implant; wherein this calibrated stimulation may be based on tested results from an actual implant or from a model implant. The system and method can apply device design and operational insights that are driven from insights obtained through measuring the electric activity and/or the osteoinductive osteolytic effect of the electrical activity for an implant, modeling the implant for desired stimulation results, and scaling the model for a target implant design.

The system and method incorporate elements and/or processes whereby electrical stimulation and/or monitoring for enhancing treatment can be specifically customized for heightened performance. In some variations the device design can incorporate detailed features whereby spatial qualities of a generated electric field are tuned by specific element features such as electrode placement, electrode surface geometry, anode/cathode arrangement, implant body design such as use of side-holes, and other considerations. As an additional or alternative variation, the systems and methods can incorporate operational related configuration that promotes stimulation within particular ranges discovered to have enhanced performance and/or to respond to state of recovery through impedance-based sensing for discovered conditions.

The implant of the system and method is preferably an orthopedic implant and more specifically a spinal cage implant that includes an implant body, a plurality of electrodes that can provide electric stimulation and/or impedance measurement, and a circuitry system that connects, powers, and controls the plurality of electrodes and other electronic components.

The system and method may generally be implemented with any electrically stimulating orthopedic device. The system and method may be particularly useful in the application of spinal fusion cages used to fuse together the vertebrae of a patient. The spinal fusion cage is implanted between two vertebrae, wherein bone growth is desired in an interior "graft window" of the cage, to fuse the adjacent vertebrae, while bone growth is generally undesirable towards the back of the patient due to possibility of damaging the spinal cord of the patient. For some cage geometries such as transforaminal lumbar interbody fusion (TLIF) cages, a certain degree of bone growth towards the posterior/dorsal/back part of the vertebral body from the implant surface may be desired depending on the placement of the cage but, generally, not so much as to extend to the vertebral foramen. In other exemplary cage geometries, such as the anterior lumbar interbody fusion (ALIF) cages or the lateral lumbar interbody fusion (LLIF) cages, bone growth towards the posterior/dorsal/back part of the vertebral body from the implant surface may generally be undesirable. Other suitable targeted zones for bone growth, non-growth, and/or bone breakdown may alternatively be used in other variations such as for other types of orthopedic implants.

The system and method may include the determination and/or application (within an implant device) of a dose response curve from the tested implant, that provides optimal levels of stimulation for bone growth and bone breakdown. This may then be incorporated with the model implant to provide region specific optimal bone growth stimulation for the target implant spinal fusion cage (e.g., bone growth in the spinal fusion cage graft window, and no bone growth or bone break down towards the spinal cord).

The system and method as one potential objective can specify the design, configuration, and operation of an implant according to a specific electrical stimulation response model to better enhance the results. In particular, the system and method can enable electrical stimulation to enhance bone growth in orthopedic medical devices used in procedures like spinal fusion surgery.

Figure 57:
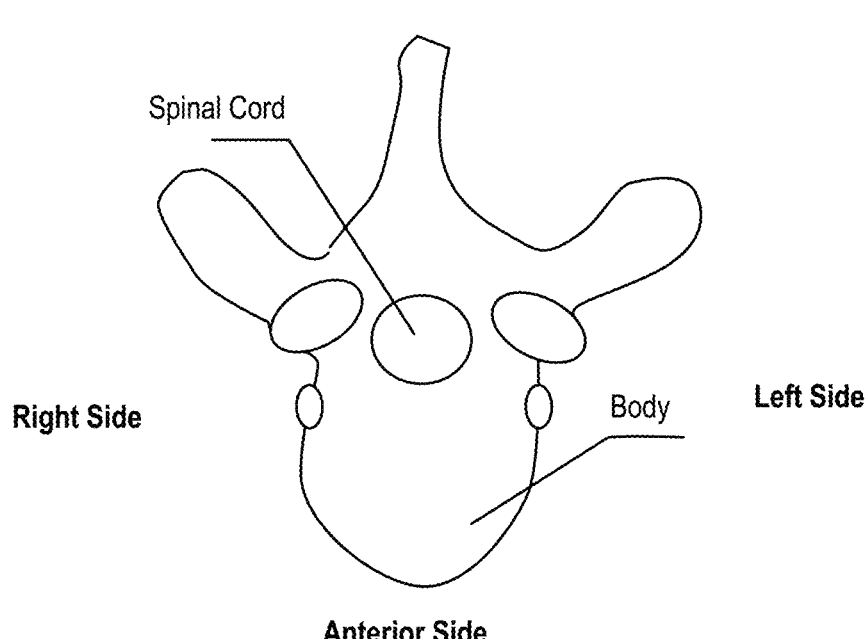
FIG. 57 is a reference diagram of vertebrae relative directions.

In a spinal cage variation of the system and method, bone growth (i.e., osteoinduction) may be desired to fuse the vertebrae adjacent to the spinal cage. Osteoinduction may be desired to occur within defined graft windows in the spinal cage. In some variations and/or certain conditions (e.g., for select patients or approach to surgical implantation), osteoinduction may be desired or not in different subregions adjacent to the outer periphery of the spinal cage. Referring to diagram of a vertebra shown in FIG. 57, a spinal cage can be surgically implanted to be contacted or otherwise placed in some portion of the body region of vertebra. Bone growth and thereby fusion between two vertebrae may be generally desired within the surface area of the body of the vertebra. Bone growth and fusion may be desired in at least portions of the posterior side of the vertebrae and in particular avoiding bone growth in close proximity to where the spinal cord is located. Depending on the geometry of a spinal cage implant body (e.g., size and geometry) and intended use surgically (e.g., intended positioning and number of implants used in combination), the system and method can target different regions of osteoinduction and/or non-osteoinduction. The system and method can calibrate the design and/or operation of a spinal cage to promote bone growth in desired regions and mitigate and/or eliminate bone growth or even breakdown bone. Herein, references may be made to cage-relative directions where these terms are based on intended or expected surgical positioning. For example, the posterior side of the spinal cage body will be the half nearest the spinal cord, the anterior side will be the half furthest from the spinal cord, and the sides of the spinal cage will be the sides as labeled in FIG. 57.

Therefore, a spinal cage directed variation of the system and method can promote calibrated delivery of stimulation for growing of bone in desired regions and not in other regions. The system and method can be implemented through a variety of implant type variations, and the system and method can facilitate these customized designs. Additionally, the system and method may enable calibrated sensing of tissue. Impedance measurements of the tested implant, in addition to impedance measurements of tissue from deceased organisms; may be used to generate a calibrated tissue profile, around and within the target implant, using the target implant impedance profile.

In some variations described herein, the system and method may be used in promoting stimulation and/or monitoring according to specific electrical properties in the volume surrounding the implant.

As an example of a variation for promoting enhanced stimulation, the system and method may produce electrical stimulation that creates desired conditions for how bone is desired to form (or breakdown). The stimulation may be controlled so as to cause stimulation conditions within tissue adjacent to the implant body that are within targeted metrics to grow bone, neutrally effect bone growth, and/or breakdown bone. These different conditions may also be calibrated to vary in the volume around the cage so that bone growth may be promoted in certain regions and not in other regions. As described herein, the system and method may stimulate using current levels calibrated to generate current densities discovered to have better performance for bone growth.

As discussed herein, the system and method may use techniques that leverage customized placement of electrodes, configuration of anode/cathode placement, electrode size, dynamical adjustment to electrode state (e.g., turning on and off electrodes to adjust current density distribution in volume about the spinal cage), integration of side through-holes to "channel" or "leak" stimulating current from one region to another, and/or other techniques may be used.

As an example of a variation for monitoring bone growth, the system and method may use impedance measurement (or other user electrical sensing techniques) to monitor the state of bone growth. The system and method can use modeling of the cage to map measurable electrical signals to predictions of levels of bone growth (or breakdown). The electrodes may be configured so that impedance can be measured through different subsets of electrodes. This can then be used to compare how it relates to expected electrical properties of different types of tissue which was discovered through experimentation, tests, and modeling.

As discussed herein the system and method may use techniques leveraging capabilities of enhanced impedance measurement such as triggering different responses by the device such as changing stimulation (e.g., ending stimulation, shifting or steering stimulation for different profiles, sending outbound communications, and/or other suitable techniques. Outbound communications may be sent to an external device that can enable a caretake (e.g., a doctor) to review data or status of the implant.

The system and method may provide a number of potential benefits. The system and method are not limited to always providing such benefits and are presented only as exemplary representations for how the system and method may be put to use. The list of benefits is not intended to be exhaustive and other benefits may additionally or alternatively exist.

As one potential benefit, the system and method may enable utilization of optimal/enhanced stimulation for bone growth. Enhanced stimulation for bone growth may enable spinal fusion implants to successfully fuse patient vertebrae at much faster rate than otherwise.

As another potential benefit, the system and method may enable spatially controlled or managed bone growth. In one variation, the design of the device may provide certain spatial properties to any stimulation such that the stimulation promotes bone growth in targeted regions and not in other regions. In another variation, the operation of the device can provide an additional or alternative way to control spatial properties of stimulation and thereby the spatial properties of bone growth.

As an additional benefit of optimal stimulation, the system and method may enable utilization of a discovered dose response curve to provide accurate stimulation in a variety of device designs.

As another potential benefit, the system and method provide a stimulation and additionally or alternatively an impedance model by which different stimulation devices can be designed.

Model-based implants may enable determination of improved and novel stimulation conditions not previously known or observed. The system and method may thus enable finding uniquely beneficial treatments that were previously unknown.

Additionally, model-based implants may enable relatively quick implementation of novel treatments. As model-based treatments may require less patient testing time, model based treatments may be implemented along a faster timeline than would be otherwise possible.

Through the implementation of model-based implants, the system and method allow the benefit of enabling machine learning. Machine learning may be employed to more completely explore the "stimulation space" of varying types of implants and geometries. Additionally, machine learning may be employed to improve tissue assessment through impedance measurements.

The system and method may enable scaling for different implants. Through the stimulation modeling, both in-vivo treatments and model treatments may be scaled for a broad range of implants.

Additionally, taking into account implant geometries, the system and method may enable scaling and thus incorporating impedance measurements from both in-vivo implants and model implants to target implants to assess tissue composition in and around the implant.

With the ability to make impedance measurements, the system and method may enable medical practitioners to analyze the presence of bone and the bone density around and/or within the implant.

2. System

As shown in FIG. 1, a system for a stimulation providing orthopedic implant includes an implant body 110; a plurality of electrodes 120; and circuitry system 130, wherein the implant system comprises at least a control circuitry system 132 that controls the activity of each electrode from the plurality of electrodes and circuitry connecting to the plurality of electrodes.

In particular, the system can include design features wherein the system is specially designed for enhanced stimulation for calibrated bone growth, enhanced monitoring of bone growth, and/or dynamic response to bone growth.

The system may be applied to a variety of types of orthopedic implants, and in particular orthopedic implants used in fusing bone. The orthopedic implant being a spinal cage implant can be one exemplary variation. Herein, examples and description primarily describe the system as it could be adapted for an implant used for spinal fusion. However, such variations may be adapted or applied to other similar types of orthopedic implants.

In one variation, as shown in FIG. 1, a system for spinal fusion can include a spinal cage body 112 that includes at least one defined graft window cavity 114; a plurality of electrodes 120 exposed on the surface of the spinal cage body; control circuitry 132 configured (e.g., including circuitry and/or computer-readable instructions configuration) to drive the plurality of electrodes in a stimulation mode. In association with the design and/or operation of the system, there may be at least a first defined region and a second defined region that are immediately adjacent to the spinal cage body, where the first defined region has a first targeted level of bone growth, and the second defined region has a second targeted level of bone growth. The defined graft window cavity may be defined to be within (or otherwise overlap with) at least a portion of the first defined region. In particular, bone may grow from endplate to endplate, and the endplate region just above and below the defined openings of the graft window cavity may be defined to be part of the first defined region. The first targeted level of bone growth and the second targeted level of bone growth may be different when implanted (e.g., in a spine between two adjacent vertebrae). The control circuitry 132 may additionally include configuration to excite the plurality of electrodes during the stimulation mode for generation of a current density in the first defined region and second defined region according to targeted levels of bone growth.

In particular, the regions may correspond to a first region that is for osteoinduction and a second region that is for non-osteoinduction. Non-osteoinduction could be characterized by no growth (e.g., stimulation below a threshold to significantly alter bone growth) or reduced growth. Non-osteoinduction may also refer to osteolysis (the breakdown of bone). Accordingly, in another variation, a system for spinal fusion can include a spinal cage body 112 that includes at least one defined graft window cavity 114; a plurality of electrodes 120 exposed on the surface of the spinal cage body; control circuitry 132 configured (e.g., including circuitry and/or computer-readable instructions configuration) to drive the plurality of electrodes in a stimulation mode. In association with the design and/or operation of the system, there may be at least a targeted osteoinduction region and a targeted non-osteoinduction region (e.g., an osteoinduction mitigation region, osteoinduction prevention region, or osteolysis region) that are immediately adjacent to the spinal cage body, where the defined graft window cavity is within at least a portion of the targeted osteoinduction region. The targeted osteoinduction region may have a first targeted level of bone growth, where bone growth and/or fusion is desired, and the targeted non-osteoinduction region may have a second targeted level of bone growth, where no bone growth or reduced bone growth (e.g., relative to the first targeted level) is desired. The control circuitry 132 may additionally include configuration to excite the plurality of electrodes during the stimulation mode for generation of a current density in the targeted osteoinduction region and targeted non-osteoinduction region according to targeted levels of bone growth.

In these variations, two regions are used but the system and/or method may be calibrated for stimulation with any suitable number of targeted regions with differing bone growth objectives.

The regions may be discretely defined but may alternatively be defined in alternative or more dynamic ways. For example, bone growth targets may be planned based on a gradient or incremental mapping of range of levels of bone growth/breakdown (e.g., osteoinduction and osteolysis). In another example, different location points can be marked to be targeted for different levels of bone growth.

In some variations the system targets growing bones to different degrees based on spatial positioning relative to the implant body 110.

Where bone growth is targeted can be predetermined based on expected surgical placement of the implant and geometry of the implant body 110. Accordingly, as described herein and illustrated in several exemplary variations, different types of spinal cage types may use different electrode design and operational configuration. The different types of spinal cage types may include, for example: anterior lumbar interbody fusion (ALIF) cages, transforaminal lumbar interbody fusion (TLIF) cages, posterior lumbar interbody fusion (PLIF) cages, anterior cervical fusion (ACF) cages, lateral cages and/or other suitable types of spinal cages.

Where bone growth is targeted may additionally or alternatively be dynamically adjusted based on current conditions. For example, the impedance measurement variations may be used to determine how much bone has grown or not grown and adjust stimulation to adjust the stimulation profile accordingly.

In some variations, the system can include a control parameter (or set of parameters) whereby spatial stimulation pattern is executed based on the control parameter. For example, a user interface could be presented within which a caretaker (e.g., a doctor could change stimulation settings for different regions), and then corresponding control parameters communicated to the implant device are used in setting the stimulation state of the set of electrodes 120.

In some variations, stimulation drives or activates all or a subset of the electrodes at specially determined stimulation levels that may have enhanced performance. In particular, there may be select magnitudes of stimulation where bone growth may be greater, where bone growth may be minimally altered, or where bone is broken down. In some variations, the first defined region is defined to be an osteoinduction region and the second defined region is a non-osteoinduction region. The configuration to excite the plurality of electrodes is further includes configuration to generate a current density in the first defined region within the range 1.8-9.1 $\mu A/cm^2$ which functions to promote bone growth and a current density in the second defined region outside of the range 1.8-9.1 $\mu A/cm^2$, which functions to not promote bone growth, when in the stimulation mode. The current density may be configured to be below 1.8-9.1 $\mu A/cm^2$, and in some variations preferably below 1.5 $\mu A/cm^2$, when no or minimal stimulation-induced bone growth activity is desired. The current density may alternatively be configured to be greater than the range 15-20 $\mu A/cm^2$, which may function to promote osteolysis or bone breakdown.

Depending on implementation and sensitive, such a current density range 1.8-9.1 $\mu A/cm^2$ may be more tightly controlled for the range and/or average values being 2.4-7.0 $\mu A/cm^2$. In one example, the range and/or average current density is configured to be 3.1-5.2 $\mu A/cm^2$.

The configuration to excite the plurality of electrodes is further includes configuration to generate a current density in the first defined region within the range 1.8-9.1 $\mu A/cm^2$ in a region that is within a distance threshold (e.g., 1-4 mm) from a bone contact surface. A bone contact surface characterizes where bone is intended to be located or in approximate contact with the implant, such as on the endplates of bone adjacent to top surfaces of the spinal cage body. For example, in the spinal cage variations, configuring the 1.8-9.1 $\mu A/cm^2$ current range within a region that is initially in proximity to bone may target suitably high current densities without over stimulating or under stimulating in other regions.

Figure 60:
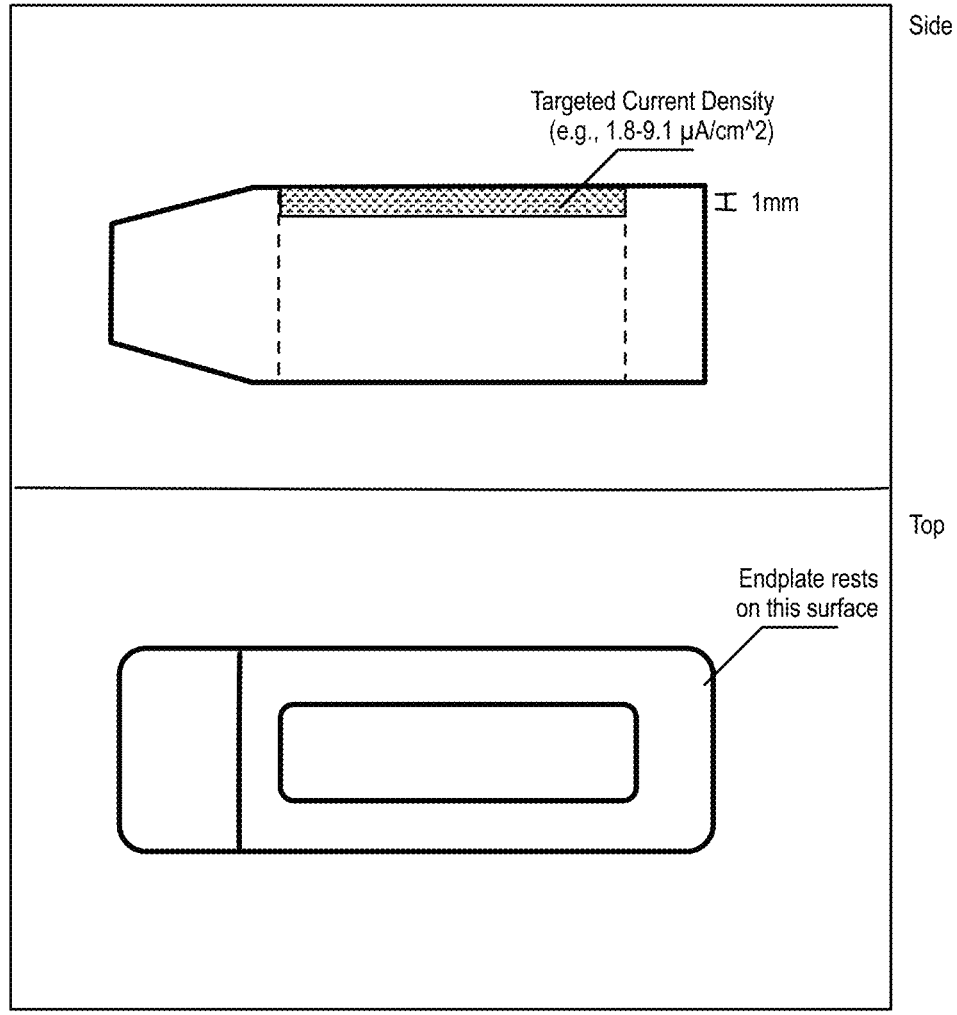
FIG. 60 is a set of top and side schematic view illustrating targeted current density ranges for an exemplary implant.

Accordingly, in some variations, such as shown in FIG. 60, the first region is a targeted osteoinduction region that includes at least part of the defined graft window cavity. Bone breakdown may occur over any electronegative region which has a current density >15-20 $\mu A/cm^2$. In one variation, the configuration to excite the plurality of electrodes may further include configuration to generate a current density in a first defined region (e.g., a targeted osteoinductive region) that is lower than 15-20 $\mu A/cm^2$. Since bone may grow from endplate to endplate, the current density in the region just next to the endplate may be of particular importance. In one variation, the configuration to excite the plurality of electrodes may further include configuration to generate an average current density in the region of the graft window within one (1) mm of the endplate surface that is between 2.4-7.0 $\mu A/cm^2$. In a preferred variation, the configuration to excite the plurality of electrodes may include a configuration to generate an average current density in the region of the graft window within one (1) mm of the endplate surface that is between 3.1-5.2 $\mu A/cm^2$. In one variation, the configuration to excite the plurality of electrodes may also generate a range of current densities in the graft window within one (1) mm of the endplate surface that is between 1.8-9.1 $\mu A/cm^2$. In a preferred variation, the configuration to excite the plurality of electrodes may generate a range of current densities in the graft window within one (1) mm of the endplate surface that is between 2.3-6.9 $\mu A/cm^2$. Such ranges and metrics described herein may, for example be based on experimental and modeling discoveries such as those shown in FIG. 62. FIG. 62, with references A1-A4, B1-B4, C1-C4, and D1-D4 indicators shown in FIG. 49, indicates various conditions (e.g., different current levels) illustrate exemplary current densities targets and results. Such discovered results may be used in scaling to other implant configurations (e.g., body dimensions/shape, electrode placements, etc.). In one variation, the configuration to excite the plurality of electrodes may further includes configuration to generate a current density in a second defined region (e.g., a targeted non-osteoinduction region) outside of the 1.8-9.1 $\mu A/cm^2$ when in the stimulation mode. In variations, where the targeted non-osteoinduction region is intended for no bone growth then configuration to generate current density in that region can be below a threshold in the range 1.8-9.1 $\mu A/cm^2$. In particular, the electrodes are configured to generate a current density below 1.5 $\mu A/cm^2$ within a targeted non-osteoinduction region such that electrically induced bone growth is reduced compared to the first defined region.

Additionally, in variations that have no defined regions with targeted osteolysis regions (e.g., regions for bone breakdown), the configuration to excite the plurality of electrodes includes configuration to generate current density in tissue with current densities less than 15-20 $\mu A/cm^2$ in all region sin proximity to the implant. In a variation or instance where there is a targeted osteolysis region, then the configuration may include configuration to generate current density greater than 15-20 $\mu A/cm^2$ in that spatial region in proximity around the implant.

A device configured with such targeted stimulation can function to have current density distribution in other regions around the implant that promotes suitable conditions for enhanced bone growth and with increased spatial control for managing areas of osteoinduction and non-osteoinduction. As described herein, such conditions may be implemented through modification of electrode size, stimulation levels (e.g., current/voltage), spinal cage body 112 geometry/design (e.g., graph window size, use of side holes, electrode placement), and other features described herein.

The configuration for stimulating according to different spatial objectives can employ one or more different features, such as special electrode placement, electrode shape/sizing, electrode stimulation state (e.g., active/inactive), anode/cathode placement, cage design (e.g., geometry, cage-type variations, use of side holes, graft window size, and the like.

In some variations, placement of electrodes may be set into a pattern to generate the current density in the first defined region and the second defined region according to corresponding targets/objects.

In one variation, placement of an anode electrode (or activation of an electrode as an anode) can be positioned near or in proximity to a targeted non-osteoinduction region. Being "in proximity" may characterize the situation where the electrode is closer to a location than any other electrode. Accordingly, the plurality of electrodes may include at least one anode electrode configured in connection with the control circuitry for excitation as an anode, wherein the at least one anode electrode is positioned on the implant body 110 (e.g., spinal cage body) based on position of the targeted non-osteoinduction region relative to the implant body 110. This may include placing an anode electrode along a surface of the spinal cage body within, adjacent to, or in proximity to the non-osteoinduction region.

In one variation, one or more anode electrodes are placed at or in near proximity to the posterior side of the implant body 110, which may function to eliminate or mitigate bone growth near the spinal cord. In some variations, where geometry of the implant body 110 is sized to not warrant osteoinduction outside of the implant, the anode electrode(s) may be placed at one or more locations along the external walls of the implant body 110, which can function to prevent or mitigate bone growth outside the perimeter of the spinal cage.

In one variation, placement of one or more cathode electrodes (or activation of an electrode as a cathode) can be positioned near or in proximity to a targeted osteoinduction region. Accordingly, the plurality of electrodes may include a set of cathode electrodes configured in connection with the control circuitry for excitation as a cathode, wherein the set of cathode electrodes are positioned on the implant body 110 (e.g., spinal cage body) based on position of the targeted osteoinduction region relative to the implant body 110. This may include placing cathode electrodes at select sites on surface of the spinal cage body within, adjacent to, or in proximity to osteoinduction regions.

In one variation one or more cathode electrodes can be placed at or in proximity to surfaces that when surgically installed would be adjacent to regions for targeted bone fusion within the bodies of adjacent vertebrae and displaced or sufficiently far away from the spinal cord.

In some variations, at least a subset of cathode electrodes may be positioned for promoting bone growth within the graft window. Accordingly, one variation, a subset of cathode electrodes is exposed along internal walls of the spinal cage body adjacent to the defined graft window cavity. There may be one, two, three, four, or more electrodes positioned within a graft window. They are preferably spaced so as to be displaced about the perimeter of the graft window cavity.

In some variations, at least a subset of cathode electrodes may be positioned strategically on external walls of the spinal cage body so as to promote bone growth along select regions on an external perimeter of the spinal cage body. This variation may be used when the targeted osteoinduction region is adjacent to a subregion of an external wall of the spinal cage body. Accordingly, the subset of cathode electrodes may include at least one cathode electrode that is exposed in the subregion of the external wall. In some varieties of spinal cage body types, such externally located cathode electrodes are placed on the anterior side relative to one or more anode electrodes (or relative to the posterior side/spinal cord location). This may include placement of a cathode electrode on the anterior side that is substantially opposite the posterior side. This may additionally or alternatively include placement of a cathode electrode on one or more of the sides of the spinal cage body (e.g., lateral right/left sides).

In some variations, cathode electrodes may include a subset of cathode electrodes positioned along internal walls defining the graft window cavity and a second subset of cathode electrodes positioned along external walls of the spinal cage body.

In some variations, sizing of electrode pads (i.e., sites) may be designed to calibrate stimulation with the desired levels. In particular, the electrode pads may be sized based on targeted current density levels in proximity to the electrode. Accordingly, a subset of electrodes may include electrode surfaces (e.g., pads/sites) exposed on the spinal cage body adjacent to a targeted osteoinduction region, where the size of the electrode surfaces is calibrated to generate current density within an osteoinduction threshold range.

Electrode sizing may be based on relationship to distance between electrodes and amplitude of current/voltage and location of the electrode on geometry of the spinal cage body.

The electrode sizing may be based on the cross-sectional surface area and/or volume of the graft window. More specifically, the electrode may be sized so as to, at least in part, satisfy the spatial current density configuration conditions described herein. More specifically, electrode sizing may be configured such that when at a stimulation current, an average current density between 1.8-9.1 $\mu A/cm^2$ is generated (or other targeted current density ranges) in a graft window cavity within one millimeter of a defined endplate surface plane relative to the spinal cage body (e.g., where the top or bottom surfaces of the body would engage with an endplate of a vertebrae). Other conditions met by the electrode sizing may include current density conditions like current density being less than >15-20 $\mu A/cm^2$ and, in a region for no growth, being below a threshold in the range 1.8-9.1 $\mu A/cm^2$.

Sizing of electrodes may be individually configured based on location and placement on the implant body. For example, electrodes near or centrally located to an osteoinduction region may be larger while, an electrode in a region with less desired stimulation may be sized smaller for reduced stimulation of bone growth in the region adjacent to the smaller electrode.

In one example TLIF implementation with a graft window cross sectional area of 62.91 $mm^2$ there are four electrodes positioned on inner surfaces and four electrodes positioned on outer surfaces, each electrode having a surface area of approximately 0.144 $cm^2$ (FIG. 23). In one example stimulation configuration, each of these electrodes may be adjusted to as a current sink with the current source placed far away. For this example, stimulation configuration, a stimulation level of 12.49 $\mu A$ is required to achieve a current density of 1.8 $\mu A/cm^2$ in ROI D3 which corresponds to the region next to the endplate in the center of the cage. For this example, stimulation configuration, a stimulation level of 12.49 $\mu A$ results in a current density of about 5.44 $\mu A/cm^2$ in ROI A1 which is the region just next to one of the active electrodes, this is well below 15-20 $\mu A/cm^2$.

Figure 34:
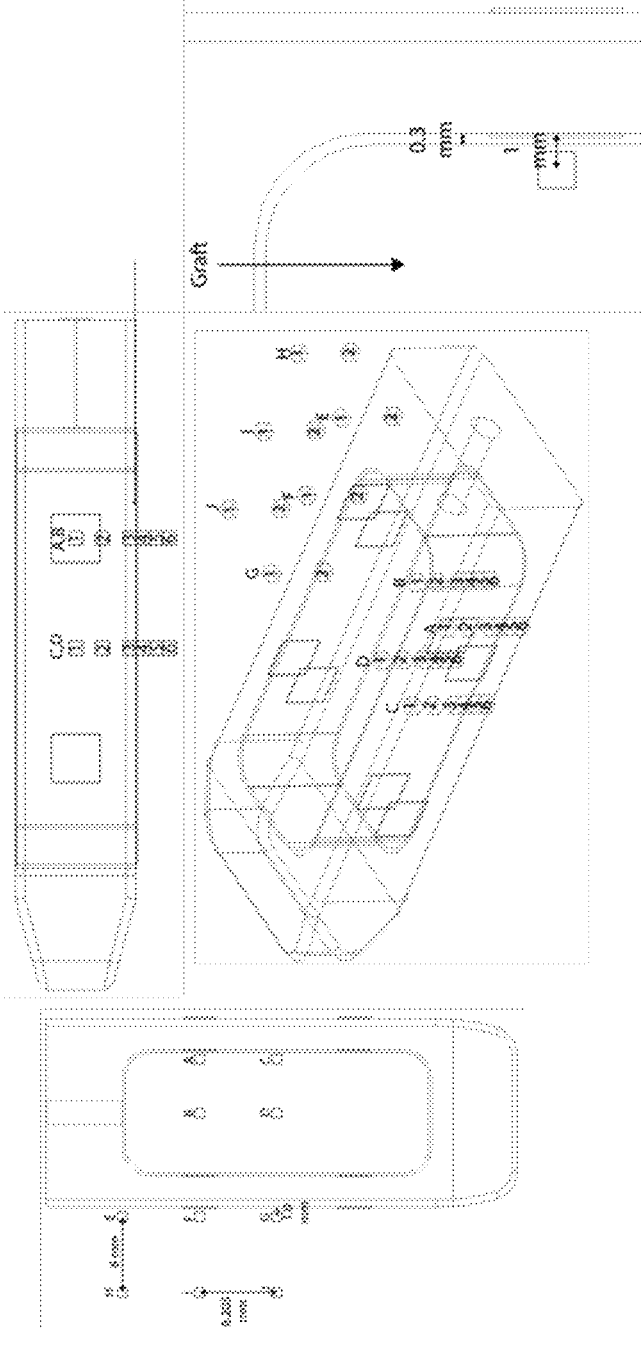
FIG. 34 is a schematic diagram of a model lateral cage.

In one example LLIF (Lateral) cage implementation with a graft window cross sectional area of 432.1 $mm^2$ there are four electrodes positioned on inner surfaces and four electrodes positioned on outer surfaces, each electrode having a surface area of approximately 0.144 $cm^2$ (FIG. 34). In one example stimulation configuration, each of these electrodes may be adjusted to as a current sink with the current source placed far away. For this example, stimulation configuration, a stimulation level of 78 $\mu A$ is required to achieve a current density of 1.8 $\mu A/cm^2$ in ROI D3 which corresponds to the region next to the endplate in the center of the cage. For this example, stimulation configuration, a stimulation level of 80 $\mu A$ results in a current density of about 41.97 $\mu A/cm^2$ in ROI A1 which is the region just next to one of the active electrodes, this is well above 15-20 $\mu A/cm^2$.

Figure 37:
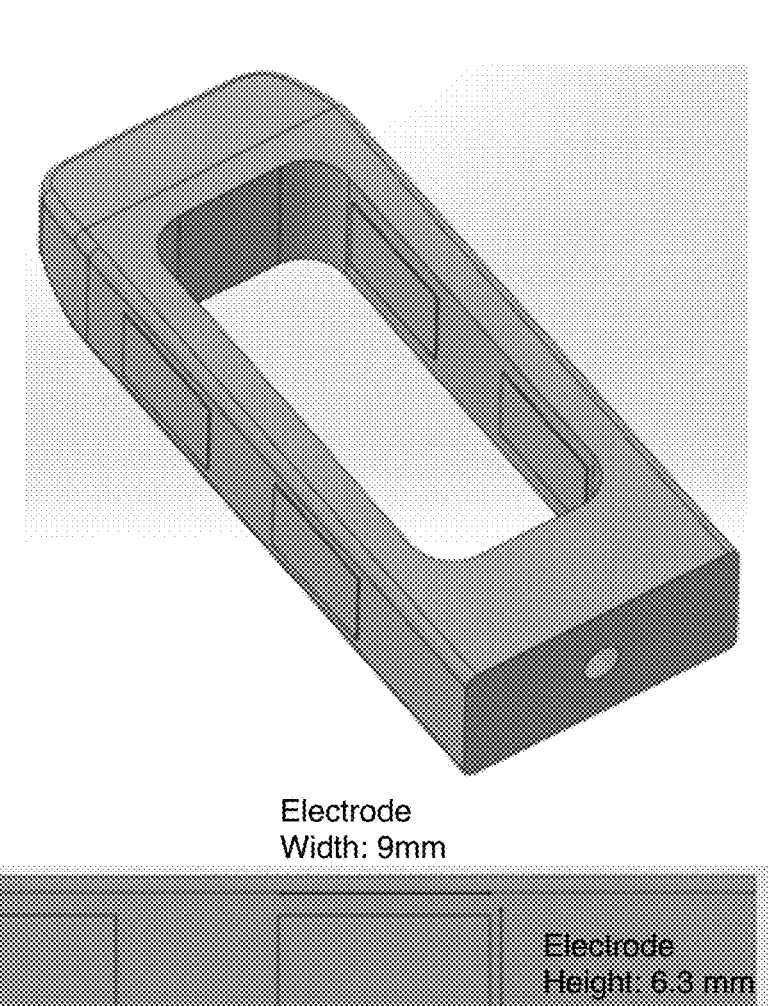
FIG. 37 is a schematic of a model lateral cage.

In some variations, increasing the surface area of the electrodes may be used to accommodate a larger graft window. In yet another example LLIF cage implementation with a graft window cross sectional area of 432.1 $mm^2$ there are four electrodes positioned on inner surfaces and four electrodes positioned on outer surfaces, each electrode having a surface area of approximately 0.598 $cm^2$ (FIG. 37). In one example stimulation configuration, each of these electrodes may be adjusted to as a current sink with the current source placed far away. For this example, stimulation configuration, a stimulation level of 78 μA is required to achieve a current density of 1.8 μA/cm² in ROI D3 which corresponds to the region next to the endplate in the center of the cage. For this example, stimulation configuration, a stimulation level of 78 μA results in a current density of about 13.5 μA/cm² in ROI A1 which is the region just next to one of the active electrodes, this is slightly below 15-20 μA/cm².

In various variations the size the electrodes may be adjusted to accommodate the cross-sectional area and/or volume of the graft window that they are configured to affect the bone growth within. In various variations the size of the electrodes may be adjusted such that it is possible to excite the plurality of electrodes with a configuration to generate an average current density in the region of the graft window within one (1) mm of the endplate surface that is between 2.4-7.0 μA/cm² while at the same time ensuring a current density below 15-20 μA/cm² within the entire graft window.

Likewise, in various variations, the number of electrodes, their positions and shapes may be adjusted such that it is possible to excite the plurality of electrodes with a configuration to generate an average current density in the region of the graft window within one (1) mm of the endplate surface that is between 2.4-70 μA/cm² while at the same time ensuring a current density below 15-20 μA/cm² within the entire graft window.

In some variations, the system may include defined through cavities within the implant body, which function to channel or pass current through the defined cavities. This may "bleed" current from one region to other regions. Such cage design properties may enable the system to adjust design of the device so that electrodes in one region can impact stimulation in "multiple" regions. In particular, this variation may be used by electrodes defined along internal walls of a defined graft window cavity to impart osteoinduction in regions on other sides of the wall (e.g., along external walls of the spinal cage body). Accordingly, when a targeted osteoinduction region is adjacent to a subregion of an external wall, the spinal implant body can include at least one defined side through-hole with one end (e.g., defined opening) within the subregion of the external wall and a second end (e.g., second defined opening) within the internal wall defining the graft window cavity. A cathode electrode can be placed on at least one of these sides. For example, there may be a cathode electrode located along the internal wall. In such variations, when an osteoinduction region spans both sides of a wall of a spinal cage body, a side through-hole can be used so that a cathode electrode on one side can distribute stimulation through the side through-hole to the other side of the wall. Use of side holes may be one potential mechanism such that the configuration of the device can satisfy the current density configuration conditions.

In some variations, stimulation drives or activates all or a subset of the electrodes at specially determined stimulation levels that may have enhanced performance. In particular, there may be select magnitudes of stimulation where bone growth may be greater, where bone growth may be minimally altered, or where bone is broken down. As described herein a general range and/or average value in a key region (e.g., in a bone contact region relative to the implant body) may be set to be 1.8-9.1 μA/cm². In some variations, the range and/or average current density in such a key region may be 2.4-7.0 μA/cm². In one example, the range and/or average current density is configured to be 3.1-5.2 μA/cm². Such targeted current density may be referred herein as targeted current density. Regions targeted for non-osteoinduction can be outside such ranges. In particular, the current density may be configured to be below 1.8-9.1 μA/cm², and in some variations preferably below 1.5 μA/cm², when no or minimal stimulation-induced bone growth activity is desired. The current density may be configured to be greater than the range 15-20 μA/cm² within regions where it's configured for osteolysis or bone breakdown.

In some variations, the control circuitry can include configuration of an impedance mode. In one variation, the control circuitry can include configuration to collect impedance measurements between at least two electrodes of the plurality of electrodes. In another variation, this can be configuration to collect impedance measurements between at least a subset of the plurality of electrodes, forming an impedance dataset. The control circuitry can further include configuration to trigger a response based on comparison of the impedance dataset and targeted levels of bone growth. Sensing of impedance using at least a subset of electrodes may use a high frequency impedance signal, which can function to measure the impedance of the tissue and minimize impact of impedance of the electrodes. In one variation, a 10 KHz or higher frequency pulse may be used. In another variation, an AC signal may be used. Other alternative approaches to measuring impedance may be used.

The comparison of the impedance dataset and targeted levels of bone growth may be based on discovered electrical properties through which impedance may be used as a metric for monitoring bone growth. According, the configuration to trigger the response based on comparison of the impedance dataset and targeted levels of bone growth may more specifically include, in some examples, such as for the TLIF cage shown in FIG. 23: configuration to detect a bone formation state when impedance measurements in the targeted osteoinduction region reaches 1.2-1.5 kΩ and detect non-bone tissue state when the impedance measurement in the targeted non-osteoinduction region is <0.6-0.8 kΩ. As mentioned herein, the example TLIF implementation shown in FIG. 23 has a graft window cross-sectional surface area of about 62.91 mm² and an electrode cross sectional area of approximately 0.144 cm². In various variations measured impedance associated with bone and/or non-bone may increase with the distance between the electrodes used for measuring the bone formation when, for example, the graft window cross sectional area is increased from one implementation to another. For an example LLIF variation with a graft cross sectional area of 432.1 mm² and an electrode cross sectional area of approximately 0.144 cm² this difference may be limited to around <35% for impedances measured for electrodes which are across each other within the inner walls of the graft window (e.g., I-II, FIGS. 25, 36) and limited to around <10% for electrodes that are located back-to-back with one located on the inner wall of the graft window the other on the outer wall of the cage (e.g., I-IV, FIGS. 25, 36). In various cage variations this difference may be limited to <50% for impedances measured for electrodes which are across each other within the inner walls of the graft window and limited to <20% for electrodes that are located back-to-back with one located on the inner wall of the graft window the other on the outer wall of the cage.

Figure 36:
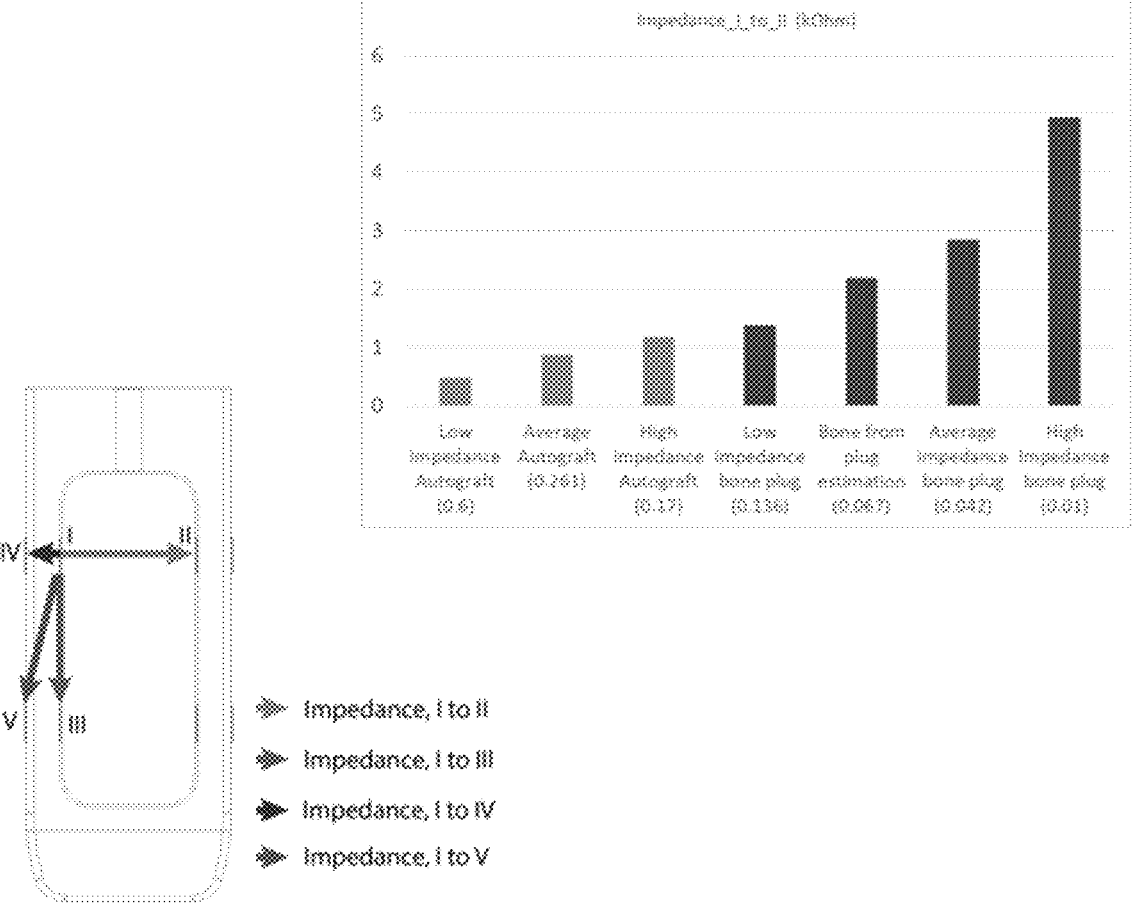
FIG. 36 is a diagram of impedance measurements for sample bone grafts over a model lateral cage.

In various implementations the impedance measured in-between two electrodes may be impacted by the size of the electrodes in-between which the impedance measurement is carried out. In various implementations the size of an electrode (electrode 1) may decrease the impedance measured in-between this electrode (electrode 1) and any other implant electrode(s) (e.g., electrode(s) 2 to (x−1) where x is the number of electrodes on the implant) as the cross-sectional area of electrode 1 is increased. One example LLIF implementation shown in FIG. 37 has a graft cross sectional area of 432.1 mm$^2$ and a surface area of a single electrode of about 0.598 cm$^2$. Impedances measured between different sites for this example variation may range between about 39.5%-46.9% (average 42.3%, FIG. 61) of that found in an example LLIF implementation with a graft cross sectional area of 432.1 mm$^2$ and a surface area of a single electrode of about 0.144 cm$^2$ (FIG. 36). In various implementations measured tissue impedance between two single electrodes may scale roughly such that the measured impedance roughly half as the electrode surface area quadruples (e.g., a quadrupling of the surface area of two electrodes that impedance measurements are measured in-between may result in halving the measured impedance assuming that the tissue impedance around and between the electrodes doesn't change materially in-between the different sized electrodes). Thus, if measuring, for example, in-between electrodes on opposite side of the graft window wall (e.g., I-IV, FIGS. 25, 36, 61), changes in impedances may not change materially with changes in graft window size and but may change with electrode size. This may similarly apply in other electrode-to-electrode pairings such as between electrodes I to III and I to V. For example, the presence of bone for a LLIF implementation with a graft cross sectional area of 432.1 mm$^2$ and a surface area of a single electrode of about 0.144 cm$^2$ may correspond to an measured impedance value >1.2-1.5 kΩ, if electrode sites quadruples in surface area the presence of bone may be signaled by a measured impedance of >0.6-0.75 kΩ whereas if the surface area is decreased to ¼ of the original electrode surface area the presence of bone may be signaled by an impedance of >2.4-3.0 kΩ. The corresponding values may not materially change for an TLIF implementation with a graft window cross sectional area of 62.91 mm$^2$ where these values may decrease <20%. They may also not materially change for various preferred cage variations of the TLIF, ALIF, LLIF, cervical et. variations. Thus, if the electrode size and position is known for various preferred cage variations, the impedance measurements corresponding to bone, and non-bone in-between electrode sites may be roughly estimated by scaling the impedance values included herein with the scaling factors included herein.

If measuring impedance of electrodes on opposite side of the graft window facing each other (I-II, FIGS. 36 and 61) the presence of bone for an LLIF implementation with a graft cross sectional area of 432.1 mm$^2$ and a surface area of a single electrode of about 0.144 cm$^2$ may correspond to an measured impedance value >1.2-1.9 kΩ, if electrode sites quadruples in surface area the presence of bone may be signaled by a measured impedance of >0.6-0.95 kΩ whereas if the surface area is decreased to ¼ of the original electrode surface area the presence of bone may be signaled by an impedance of >2.4-3.8 kΩ. The corresponding values may materially change for an TLIF implementation with a graft window cross sectional area of 62.91 mm$^2$ where these values may decrease by around 35% yielding corresponding values. Similarly, the impedance values may be adjusted for graft window size for any implant variations that contain electrode sites that are located at opposite ends from each other within the graft window assuming that a relatively unobstructed path (unobstructed by implant body) can be drawn between them.

Figure 25:
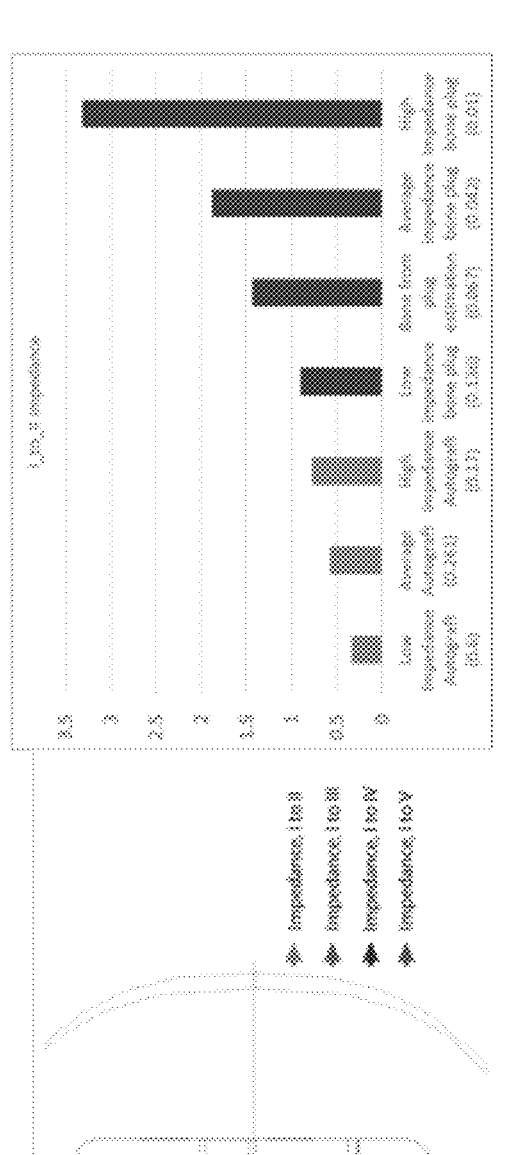
FIG. 25 are impedance measurements for sample bone grafts over a model TLIF cage.

Many of the examples provided above discusses the impedances measured to signal the presence of bone but the impedance of non-bone tissue may be similarly scaled in a similar way as shown in FIGS. 25, 36, 61. Thus, in various preferred implementations, if the adjustments of the measured impedance value(s) signaling the presence of bone in-between two electrodes can be made based on electrode site size and/or position, the measured impedance values signaling the presence of non-bone tissue may can be made using approximately the same scaling factors.

In various implementations, impedance measured in-between a plurality of electrodes (>1) of any cross-sectional area(s) (set 1) and one or a plurality of electrodes (set 2) may be lower than the measured impedance in-between any individual electrodes in set 1 and the electrode(s) of set 2. In various implementations, measuring the impedance between one (1) electrode and a plurality of electrodes located on an implant may increase the influence of the local impedance around the single electrode on the measured impedance signal compared to the local impedances around each electrode belonging to the plurality of electrodes. In preferred variations, measuring the impedance between one (1) electrode and the entire plurality of electrodes may increase the influence of the local impedance of tissue surrounding the single (one) electrode on the measured impedance signal. Likewise, for various variations, the impedance measured over one subset of a plurality of electrodes and second subset of plurality of electrodes may provide a measurement of the impedance of tissue surrounding each electrode belonging to each subset and the impedance of tissue in between the impedance surrounding each electrode. In various implementations. cycling through impedance measurements of different subgroups of a plurality of electrodes, can provide a spatially resolved map of the impedance of the entire region surrounding an implant body.

In various implementations, the formation of bone may be signaled by an increase in impedance between any two electrodes that corresponds to around 1.5-4× the impedance measured over the original graft material in the days directly following surgery irrespective of exact implant implementation. In various implementations, an increase of around 1.5× may indicate low confidence of bone formation, an increase of around 2× an medium confidence, and an increase of around 3× a high confidence, and an increase of >4× a very high confidence. In various implementations, a measured increase in impedance of any one electrode >4× from one day to the next (within 24 hours) may indicate implant failure rather than successful bone growth whereas a gradual increase of 4× may indicate a high confidence in bone formation. In various preferred implementations an increase in the impedance signal in-between two electrodes in the graft window >2-3× the original impedance may be a signal for a successful fusion through the graft window. In various preferred implementations an increase in the impedance signal in-between two electrodes in the graft window >2-3× the original impedance may be a signal for a successful fusion. The bone formation state may indicate if bone is forming (e.g., impedance changes indicate growth), if the region has any bone, if the region indicates bone growth above a determined threshold. The non-bone tissue state can be similar but may be used more to try to avoid bone growth in that region.

In one variation, an impedance triggered response may be or include an initiation of a communication. This can be a communication to an external device. The communication can enable current bone growth state. For example, an alert could be triggered to indicate that bone growth has met a certain threshold within a graft window. In another example an alert may be triggered to indicate that bone growth is occurring above a select threshold in a region where bone growth is not desired. In yet another example, the impedance measurement dataset may be sent up so that an external device that includes a control user interface can update stimulation state.

The response may alternatively be an update to the stimulation state. This may be performed because the targeted osteoinduction region and non-osteoinduction regions may change over time. Updating the stimulation state may involve adjusting distribution of stimulation, which functions to "steer" stimulation and thereby bone growth. This can be performed by adjusting stimulation magnitudes for different electrodes or by activating/deactivating particular electrodes. According, in some variations, configuration to trigger the response is configuration to deactivate at least a subset of electrodes to adjust stimulation distribution relative to the spinal cage body. This may be done when bone growth in osteoinduction regions is satisfied. This may also be done when bone growth is occurring a subregion where bone growth is not desired. Adjusting distribution of stimulation may additionally or alternatively include changing magnitude of electrodes, altering anode/cathode states, and/ or turning electrodes on/off. With a plurality of electrodes turning electrodes on or off may be one preferred approach to adjusting balance of stimulation.

Preferably, configuration to collect impedance measurements collects between a plurality of different pairs of electrodes. This may include cycling through performing impedance measurements between every permutation of electrode pairs within at least a sub-set of the plurality of electrodes. In another variation, impedance measurements may be collected through pre-configured pairs. For example, select pairs of electrodes may be used because of how their relative position would collect impedance information in key regions. The impedance dataset can form a spatial impedance map relative to the implant body 110.

The system may additionally comprise additional attachments to the implant body 110. In some variations, as shown in FIG. 2, the system further comprises a housing attachment. The housing attachment (also referred to as nosing) may be fixed to the implant body 110 and contain some or all of the implant circuitry 130. The system can function as a surgically implanted orthopedic device that can dynamically deliver and/or monitor electrical stimulation (e.g., to promote and/or monitor bone growth as a spinal fusion implant). In particular, the system is applied to a spinal fusion cage, which preferably includes stimulation capabilities enabled through the plurality of integrated electrodes 120. A stimulation-enabled spinal cage is preferably calibrated to generate controlled electrical fields promoting osteoinduction and osteolysis in a way that is enhanced to the geometry and use of the particular type of spinal cage (e.g., lateral cage, TLIF cage, ALIF cage, etc.). The spinal cage variation may additionally or alternatively include an enhanced impedance measurement system that can also be specifically calibrated to monitor tissue according to the design of the spinal cage.

The system may additionally include "non-implantable" components, i.e., components not implanted that function to interact with the implant (e.g., communicate, control, and monitor the implant). Examples of non-implantable components include: a power source, a transmitter circuitry, and optionally transmitter communication circuitry, which functions to wirelessly deliver power to and/or communicate with the implantable component.

Figure 4:
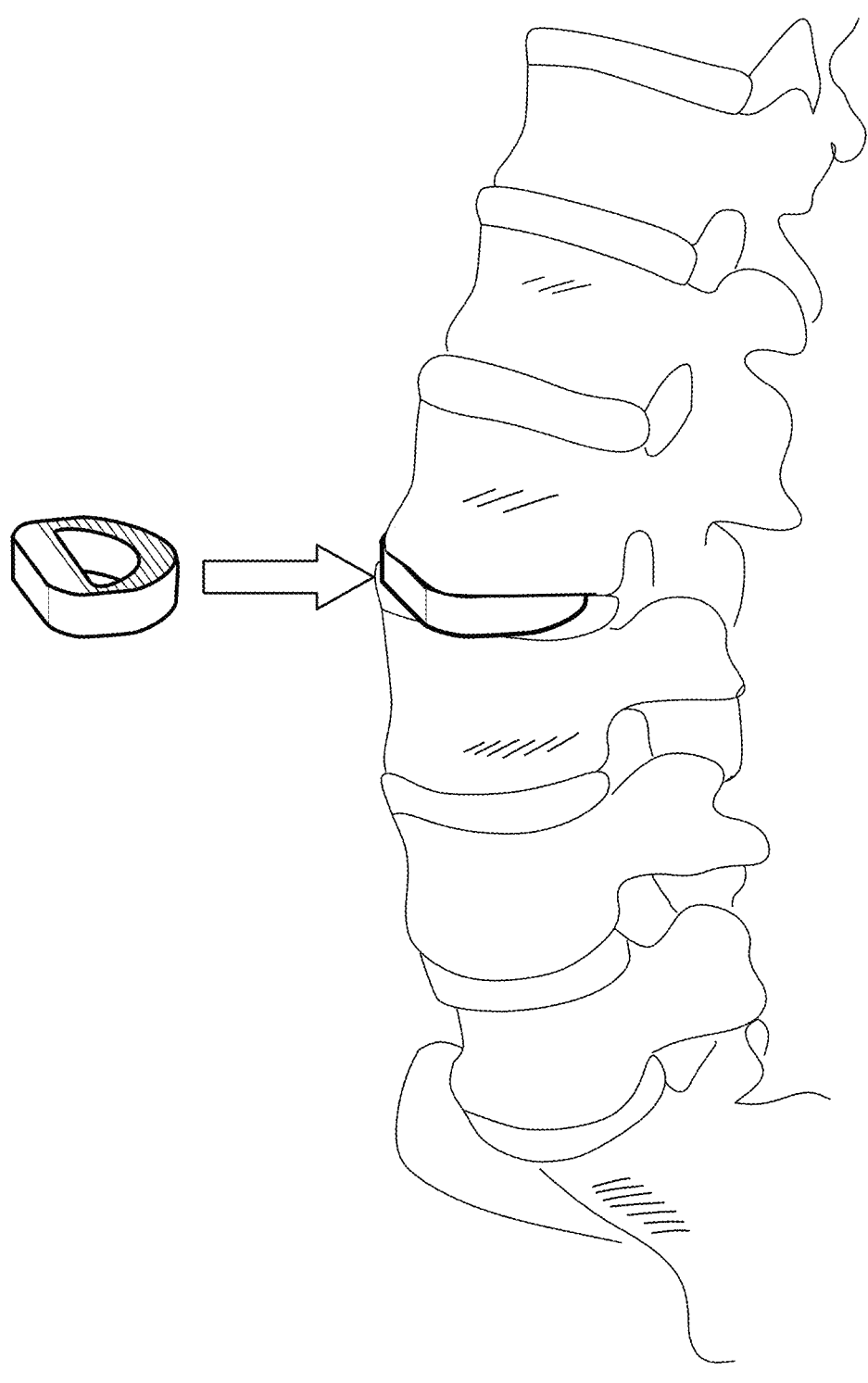
FIG. 4 is an illustration of an implant insertion.

The system can be used in a wide variety of applications that use orthopedic implants such as in a spinal fusion operation. In a spinal fusion implementation, the implant is inserted into the spine such that the implant is situated between two vertebrae as shown in the schematic representation of FIG. 3. Dependent on the type of implementation and/or type of implemented spinal fusion implant, the implant may be inserted into the vertebral column in different ways. For example, as shown in FIG. 4, an ALIF cage may be inserted from the anterior side of the spinal column. Additionally, external portions of the system may be integrated with apparatuses common with the corresponding procedure. For example, cervical collars and lumbar corsets can include a wireless power transmitter for a spinal fusion implementation of the implantable component.

In the spinal fusion implementation, the system may function to provide electrical stimulation to promote bone growth and/or optionally bone decay. Additionally, the system may monitor tissue composition by measuring the impedance of electrical stimulation in tissue proximal to the implant. These processes may be performed distinctly or together as desired.

The system may alternatively be applied to other medical spaces where an implant could provide electrical stimulation or bone growth monitoring (or other applications of impedance monitoring). Herein, the use case of a spinal fusion orthopedic implant is used as a primary example, but one knowledgeable in the art could appreciate how the system may be applied to other implant applications.

In various embodiments, the implantable and non-implantable component(s) may include circuitry to store, process and wirelessly communicate data and control signals between the implantable and non-implantable component(s) and between non-implantable component(s) and user interface components. Examples of data that may be communicated between implantable and non-implantable component(s) and non-implantable component(s) and user interface components include control signals specifying the magnitude of stimulation, control signals specifying the state of electrodes during stimulation (anode, cathode, passive), control signals specifying the frequency, duty cycle and mode of stimulation (AC or DC etc.), control signals specifying the shape of the stimulus waveform, control signals specifying the scheduling or frequency of stimulation, control signals specifying the frequency of impedance measurements, diagnostic data communicating the state of the implantable component including any discrepancies between received and consumed electrical power, diagnostic data communicating the state of the non-implantable component including the state of the power source, and data communicating results from impedance measurements.

The implant body 110 of a preferred embodiment functions as a primary structural element of the implant. The implant body 110 is preferably made of non-conductive material but may be partially conductive. The implant body 110 may structurally serve a medical objective. The shape and form may be the same, or similar, to other passive medical device implant bodies no; such as orthopedic implant devices like cervical plates, spinal cages, meshes, and nails. The implant body 110 is preferably integrated with the plurality of electrodes 120 such that electrical stimulation enhances recovery. The medical implant bodies may house some or all circuit elements (e.g., PCB, leads, antennas etc.) included as part of the implantable components. Preferably, the implant body 110 includes integrated electrode sites, which may be distributed across the geometry of the implant body. These integrated electrode sites may be distributed in such a way as to facilitate bone growth and bone reabsorption in distinct regions. In some embodiments, the implant body 110 can be a spinal implant, which may be a spinal cage. A non-exhaustive list of descriptions of typical spinal cages that may be incorporated with the system will follow. As spinal cages may be highly specialized for each individual implementation, all provided spinal cage specifications are provided as typical descriptions of that spinal cage and not presented as a limitation for each spinal cage per se.

The spinal cage (i.e., a spinal cage body) variation of the implant body 110 may be made of a polymer, such as PEEK, or it may be made of engineered natural or synthetic bone material, or some other material. The spinal cage generally has an extruded prism geometry with many variations dependent on the specific type of spinal cage. As per a prism, the spinal cage geometry has an external surface comprising: a sufficiently flat and opposing position (e.g., parallel), top and bottom surface; and a more complex outer wall geometry that may be distinct to the specific spinal cage implementation. Herein, opposing in position characterizes the general geometry of the top and bottom surfaces of the implant without requiring the surfaces to be parallel or flat and may include surfaces defined along intersecting planes. Preferably, the opposing surfaces are defined along planes with angular offset between 0-10 degrees, although the offset may be more. For example, in many implementations, the top and bottom surfaces are skewed several degrees to achieve lordosis. As discussed here, the exterior perimeter of the spinal cage is defined as the perimeter along the lateral (i.e., side) wall geometry.

The calibration of stimulation for different regions in the space around the implant may be based on expected orientation of the implant body 110 when implanted in the body. Different types of spinal cages (e.g., ALIF, TLIF, PLIF, etc.) may have different orientations when installed. Similarly, there may be different goals for bone growth in space adjacent to these different types of spinal cages. For example, bone growth may be desired to be kept internal within the graft window for large spinal cages, but smaller spinal cages may ideally have bone growth occur in the regions surrounding the spinal cage. At times, references are made to directions using body (or vertebrae) relative terms. For example, posterior may be used to characterize a direction closer to the back of the body, anterior may be used to characterize a direction near the front of the body, and left or right sides may be used indicate the lateral directions of the body. In many situations, osteoinduction is desired within the body region of the vertebra, but a non-osteoinduction region may be targeted at or near the spinal cord (e.g., the posterior side) to avoid complications.

The spinal cage can include one or more graft windows, which can be defined as internal implant cavities, wherein these internal implant cavities are defined by the interior surface of the spinal cage. Implant cavities are typically prism shaped with openings in the top and bottom surfaces of the spinal cage. The spinal cage body 112 will generally include at least two surfaces that are in contact with the two vertebral endplates on the top and bottom of the cage. The interior surface of the spinal cage thus refers to the lateral walls that define the internal cavities forming the graft window. In some variations, internal cavities may have openings in addition to the top and bottom openings. As desired by implementation, these additional surfaces may also be included as part of the interior surface. The graft window is preferably a space in which bone growth is desired and in which stimulation by the plurality of electrodes 120 can promote and/or modulate the degree of bone growth. Preferably, the spinal cage achieves bone fusion within the graft window between the adjacent vertebrae.

In some variations, a spinal cage may include multiple graft windows. These multiple graft windows may be completely distinct such that the multiple graft windows are far from each other on the implant body 110. Alternatively, the graft windows may be divided by a separator, i.e., a relatively thin implant body 110 volume that separates a graft window. Separators may be incorporated with the implant body 110 construction to manage the graft window volume. That is, separators are constructions that may be incorporated with a previously designed implant body 110 to divide a graft window. Separators may function to enable scaling of the functionality of small implant bodies (and implant body models) to larger implant bodies for the purposes of modifying the stimulation fields and/or for adding additional electrodes. For example, a separator may be incorporated to divide the graft window of a lateral cage as part of scaling the functionality of a TLIF cage for the lateral cage. As desired, the implant body 110 may include zero, one, or multiple separators.

In addition to a graft window, in some variations, the spinal cage may include side holes. More specifically, these may be described as defined side through-holes. Side holes can be defined cavities with ends on either end of a wall. In some variations, a side hole is a defined cavity that extends between the external perimeter of the implant body 110 to the interior perimeter of the implant body 110 (e.g., internal wall of a defined graft window cavity). Side holes may function to improve current transfer between the interior and the exterior regions of the implant body 110. Additionally, side holes may better enable transfer of fluids and biological material between the interior and exterior regions of the implant body 110.

In some variations the side holes are relatively cylindrically shaped, but may alternatively have any desired shape (e.g., rectangular solid). Dependent on the implementation, the spinal cage may include zero, one, two, or more side holes. As an alternative perspective, removal of holes may concentrate current, or charge, within the graft window. For impedance measurements, removal of holes may thus have minimal, or negligible effects through material with low conductivity, wherein measured impedance may decrease through material with higher conductivity.

In some variations, the spinal cage may include a single side hole. In some variations a single side hole may be an anterior facing hole (towards the front or belly), a posterior facing hole (towards the back or spinal cord), or an end facing hole (positioned on one of the shorter sides of the implant) Generally, one or more side holes may be on any side of the implant body 110 (or along any curvature of the implant body for implants with curved sides). During stimulation, including the graft window stimulation, the hole may enable growth on the exterior of the implant, towards an exterior cathode electrode, or sharper depletion towards an exterior anode electrode.

The spinal cage may be incorporated with many geometries including, but not limited to, anterior lumbar interbody fusion (ALIF) cages, transforaminal lumbar interbody fusion (TLIF) cages, posterior lumbar interbody fusion (PLIF) cages, anterior cervical fusion (ACF) cages, lateral cages and/or other suitable types of spinal cages. In some implementations the spinal cage geometry is an extruded prism of some defined form, which generally has a continuous outline and at least one defined internal cavity. More common geometries of the spinal cage may have a rectangular prism resemblance and may be considered "sufficiently" rectangular to describe components with respect to the sufficiently rectangular implant body 110. The rectangular body comprises a top surface, bottom surface, two shorter sides, and two longer sides; an exterior surface comprising the lateral sides (i.e., the two shorter sides and the two longer sides); and an exterior perimeter comprising circumnavigating the lateral sides. In some variations the rectangular body may have some curvature and geometric features along some or all sides. As shown in FIG. 8, this curvature may include curved edges of the implant body 110 and/or curvature of the entire rectangular body. The spinal cage may include other design features such as: surface coatings, surgery tool attachment points, teeth, and/or other elements. The spinal cage is preferably composed of a non-conductive polymer, such as PEEK, but may be made of engineered, natural or synthetic bone material, titanium and/or other suitable material or combinations thereof.

In some variations, the implant body 110 is a TLIF cage, such as shown in FIG. 5. The TLIF cage is a more rectangular shaped spinal cage that may be used in small incisions for Transforaminal Lumbar Interbody Fusion, wherein, a single, or multiple implants may be inserted between a pair of vertebrae. Typical dimensions of the TLIF cage may vary from 7×9×23 mm-16×1×34 mm. Additionally, the body of the TLIF cage may have a curvature.

Figure 7:
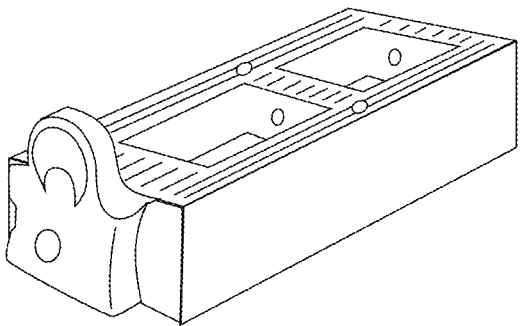
FIG. 7 is an illustration of a lateral cage.

In some variations, the implant body 110 is a lateral cage. FIG. 6 and FIG. 7 show typical lateral cages. The lateral cage is a more rectangularly shaped cage and generally elongated along one dimension with two "end" surfaces being smaller in surface area than the adjacent "elongated" surfaces. Lateral cages may vary between 8×18×30 mm-14× 21×60 mm, with an interior cavity space that may vary from 1.4 mL-11.6 mL.

Figure 9:
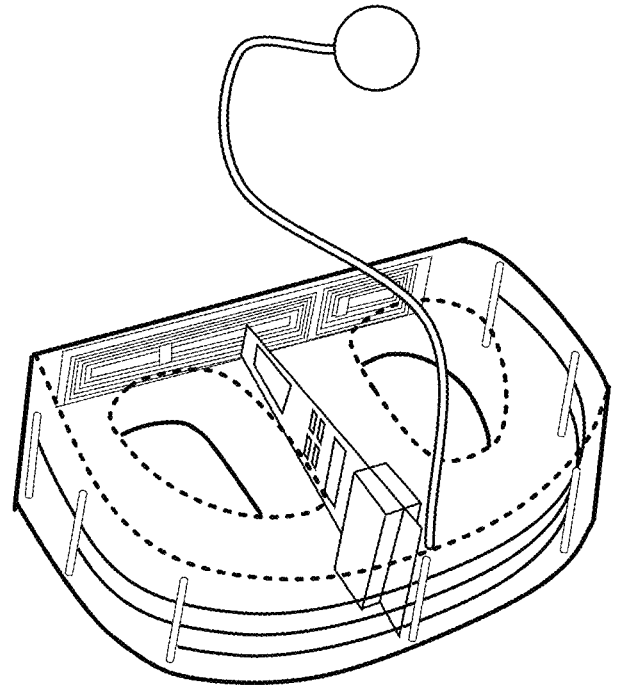
FIG. 9 is an illustration of an ALIF cage.

In some variations, the implant body 110 is an ALIF cage such as shown in FIG. 8 and FIG. 9. The ALIF cage is typically optimized for implantation in the anterior lumbar region of the spinal cord for anterior lumbar interbody fusion, as shown in FIG. 4. The ALIF cage is typically a larger spinal cage implant with a curved body, wherein both the exterior perimeter and/or the interior perimeter (of the graft window) may be curved. Typical ALIF cages may vary between 10×25×35 mm-18×28×39 mm with an interior cavity space that may vary from 2.0 mL-8.0 mL.

In some variations, the implant body 110 is a PLIF cage. The PLIF cage may be a smaller implant body 110 as compared to the ALIF cage, preferably optimized for implantation in the posterior lumbar region of the spinal cord for posterior lumbar interbody fusion, wherein multiple implant bodies may be inserted between a pair of vertebrae. Typical dimensions of the PLIF cage may vary from 6×10× 25 mm-16×12×32 mm.

In some variations, the implant body 100 is an ACF cage. The ACF cage may be a smaller square-like spinal cage implant inserted preferably between cervical vertebrae. Typical dimensions of the ACF cage may vary from 5×14× 11 mm-10×17×13, with an interior cavity space that may vary from 0.20 mL-0.9 mL.

In alternate variations the implant body may be an orthopedic implant that may or may not have an interior cavity. Orthopedic and non-orthopedic implants that may implement localized bone growth preferably include joint and extremity implants and other connective implants Examples of these implants include: hip implants, knee implants, implant plates, implant nails, and implant screws. The system may additionally be implemented with any other system implant wherein localized charge may be implemented to aid a patient.

The plurality of electrodes 120 of a preferred embodiment function to hold or transfer charge from and to the implant, and to and from the surrounding tissue. An electrode is preferably a conductive element that includes an electrode site (e.g., a conductive pad exposed to body tissue) connected (directly or indirectly) to other implant components (e.g., control circuitry system 132 and/or power system). The plurality of electrodes is preferably constructed of electrically conductive material. The plurality of electrodes 120 are preferably conductively isolated from the implant body 110 and exposed at a set of distinct electrode sites. The implant sites are preferably exposed electrode sites on or near the interior surface of the implant body 110 and/or on or near the exterior surface of the implant body. In some preferred variations, exposed electrode sites may include electrode sites distant from the implant body 110 (e.g., distant to desired bone growth regions). The electrode sites are distributed across the geometry of the implant body 100 in such a way as to facilitate the osteoinduction and osteolysis in desired bone growth regions during a controlled stimulation mode. The electrode site geometry can be configured for differing current density profiles.

In preferred variations electrodes are partially embedded in the implant body 110. These electrodes have at least one "embedded" region within the implant body 110 and at least one "exposed" region (i.e., exposed electrode site), such that the implant body does not completely insulate the electric field generated by the exposed electrode site from external tissue. The exposed electrode site may be along an interior surface (e.g., exposed to an interior cavity or through hole) or an exterior surface (e.g., adjacent to external tissue) of the implant body 100. Embedded regions may include: regions where electrodes are molded into the implant body 110; run through slits and/or holes in the implant body; encased in regions of the implant body; and/or incorporated within the implant body in some other way. Embedded regions may vary significantly depending on the size and/or shape of the electrode.

Each electrode may be of any desired shape and/or size. In some preferred variations, some electrodes may be wires exposed at defined electrode sites on and/or around the implant body 100. Other examples of electrodes may include, but are not limited to: thin wires, thick wires, layers of distinct wires, sheets, discs, pads, screws, metallic bodies, rings, covering shapes of the implant body 110, covering shapes of the implant body cavity, and/or any combination of the aforementioned examples. In one preferred variation the plurality of electrodes 120 include wires embedded and integrated within the implant body 110. In another variation, the plurality of electrodes 120 include a metal casing on the external surface of the implant body 110. The exposed electrode sites of electrodes function to enable current transfer to tissue on, or near, the implant body 110. The electrode sites are preferably flush with the surface of the implant body 110 along the interior or exterior cavity of the implant body 110. Alternatively, the exposed electrode sites may protrude from the implant body 110 or be recessed within the implant body.

Electrode surfaces exposed on the spinal cage body may be sized according to calibrated objectives for stimulation and bone growth. Where more bone growth is intended large electrode surfaces may be used compared to where no or little bone growth is desired. In one variation, electrode surfaces exposed on the spinal cage body adjacent to the targeted osteoinduction region, the size of the electrode surfaces may be calibrated to generate current density within an osteoinduction threshold range. Exact sizing may depend on current levels of electrodes, number of electrodes, and/or placement of electrodes on the implant body.

The electrodes of the plurality of electrodes 120 function to hold or transfer charge from and to the implant, to and from the surrounding tissue. Preferably at any given time, charge transfer occurs with a substantially equal charge, being generated at a source and dissipated at a sink; thereby creating an electric field that may induce bone growth, osteoinduction; or bone breakdown, osteolysis. The electrodes are preferably configured for electrical stimulation at, within, and/or around the implant body 110. Electrodes of the system may further be characterized as any material that may function as a cathode or anode of a circuit, allowing current to flow from one to the other. Depending on the implementation and desired electrode function, control of the plurality of electrodes 120 may be implemented to manipulate the charge, charge density, current, current density, and/or electric field between any and/or all electrodes.

Electrodes may function as either cathodes and anodes, i.e., current sinks and current sources respectively; to create regions of bone growth (osteoinduction), and bone breakdown (osteolysis). In some variations, the electrodes may be connected to circuitry such that electrode state is switchable so that one electrode may selectably act as an anode during stimulation in one state or act as an anode during stimulation in another state. As another variation, one or more electrodes may have selectable active/inactive status (e.g., on/off) such that one or more electrodes may be selectably active such that it participates during stimulation or inactive such that it does not participate in stimulation.

The plurality of electrodes 110 are preferably situated such that, at least one electrode has an exposed electrode site in a "bone growth" region, to induce osteoinduction or osteolysis. As desired, the system may have multiple bone growth regions. Dependent on implementation, circumstances regarding the current status of bone growth, and potentially other factors, the desired activity in the bone growth region may change over time. Thus, a specific bone growth region may at times be a region for osteoinduction, osteolysis, or no activity. In preferred variations, wherein the implant body 100 contains an internal cavity, the internal cavity is preferably a bone growth region. In alternate variations, the internal cavity is not a bone growth region.

Each electrode from the plurality of electrodes 120 may be enabled for independent operation. Alternatively, subgroups of electrodes are enabled for independent operation as a set (e.g., a set of electrodes may function independently as a group). Independent operation can include individual (or subgroup) control of anode/cathode state and/or active/inactive state. Independent function enables precise control of current through each electrode such that the direction and magnitude of current through each electrode may be individually determined and set, as desired. Additionally in some preferred variations, the type of current can also be independently controlled (e.g., direct current, or alternating current). As an additional functionality independent function of each electrode, or groups of electrodes, may enable modified, or different, functionality for electrodes at any given time. For example, an electrode in a region that was initially functioning as a cathode to induce bone growth, may have a reduced current flowing through, or may be completely inactivated to reduce bone growth in that region. At another time the same electrode may function as anode to promote bone break down. At some other time, the electrode may be used to make impedance measurements.

In some alternate variations, electrode function has limited and/or fixed operation. For example, the system may have a "fixed" source, wherein one set of electrodes may only function as a current source, while another set of electrodes may function only as a current sink. In some variations, certain types of electrodes (e.g., of a specific size or shape) may have a fixed functionality. For example, electrodes may be grouped in functionality based on size, wherein "smaller" electrodes may be implemented and used just for measuring impedance, while "larger" electrodes may be used for stimulation purposes.

Since power is the product of current and electrical potential (P=V*I), the choice of materials making up the anodes and cathodes may greatly impact the amount of power that needs to be supplied by the power system in order to cause osteoinduction/osteolysis. This is of special concern in implantable systems where power required to drive current between the electrodes is provided wirelessly since it is difficult to transmit large powers over large distances. Power requirements can impact at what depth a system can be implanted where a system that utilizes anode/cathode materials. For example, a system with anode/cathode where small potentials are applied over the cathodes/anodes to drive a desired current may be implanted deeper into a patient compared to a system that utilizes anode/cathode where larger potentials are preferably used to drive the same current since the latter requires more power. A greater power consumption also requires larger power sources, which may affect the bulk of the implant and/or power system.

The circuitry system 130 of a preferred embodiment, functions as the electrical system used in operation of the implant. The circuitry system 130 preferably includes a control circuitry system 132 that controls the activity of each electrode from the plurality of electrodes 120, and circuitry that connects the plurality of electrodes and all circuitry system components. Dependent on the implementation, the circuitry system 130 may additionally include: a power system (e.g., stored power, a wireless power system, or other power source) that provides energy for electrode stimulation; a communication system, comprising antennas and communication circuitry for communication with non-implantable components and non-system components; sensors (e.g. pressure sensors to measure stress on the implant), signal producers, signal converters (e.g. digital to analog converters), and/or any other desired component. In some variations, the circuitry system 130 may include "wireless" components for wireless energy transfer and/or communication.

Figure 10:
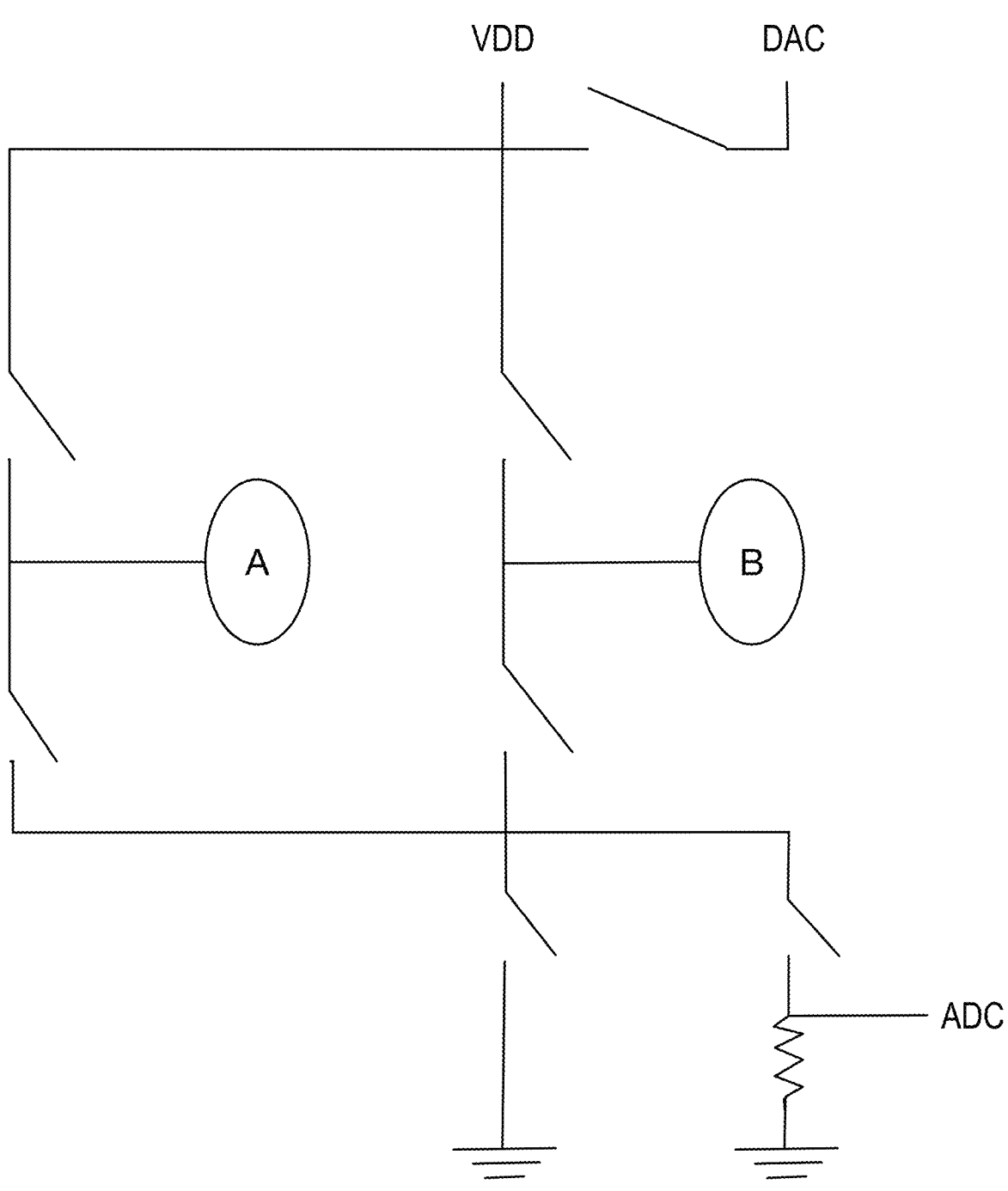
FIG. 10 is a schematic variation of the system circuitry.
Figure 11:
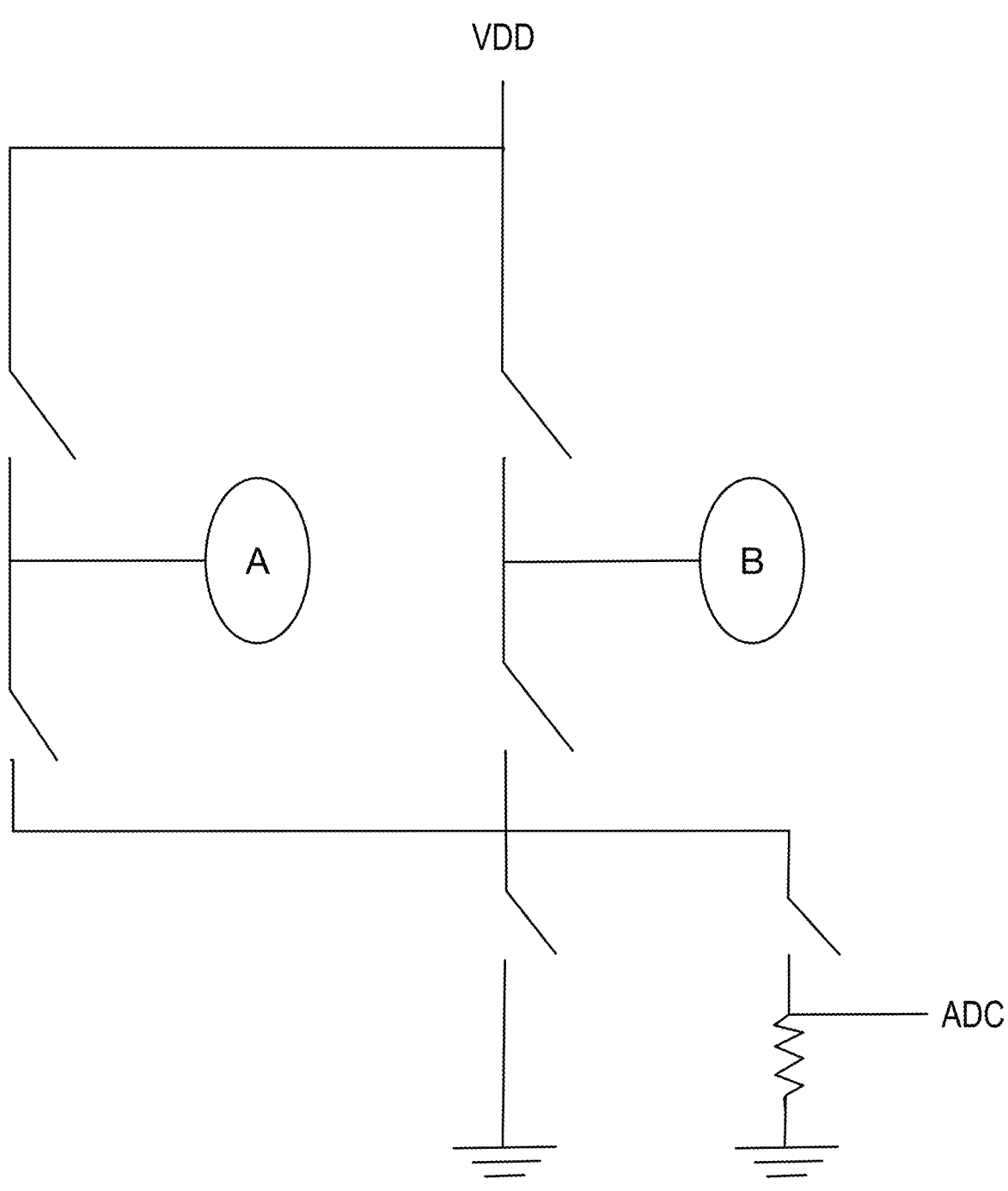
FIG. 11 is a schematic variation of the system circuitry.

The circuitry system 130 preferably includes circuitry connections, which functions to connect circuitry system 130 components to the plurality of electrodes 120. Additionally, circuitry connections may connect other system components. Circuitry connections may be embedded in the implant body 110, housed in implant attachments, or contained in some other region. In one variation, each electrode may have a distinct circuitry connecting the electrode to a power source and the control circuitry system 132. In another variation, as shown in FIG. 10, circuitry connections may connect a single power source to two (or more) electrodes, wherein the control circuitry system 132 may open or close switches to direct the direction of current through electrodes A and B. The circuitry connections may additionally connect to a signal producer/converter (e.g., DAC) that propagates signals for impedance measurements. In an alternative variation, as shown in FIG. 11, the power signal itself may be used for impedance measurements.

The implant circuitry 130 preferably includes a control circuitry system 132. The control circuitry system 132 may function to control the charge amplitude and polarity of the plurality of electrodes 110. The control circuitry 130 may include configuration to manage different operations of the implant system. The control circuitry configuration may include circuit-based design and/or machine-readable medium (e.g., a non-transitory machine-readable medium instructions) and processor configured to perform those operations or processes.

The control circuitry system 132 may additionally control, sync, and/or operate other components as deemed necessary. In some preferred implementations, wherein electrodes have multiple functionalities (e.g., dual activity circuit electrodes), the control circuitry system 132 preferably controls and changes these functionalities. The control circuitry system 132 may control the dynamic and multi-operating modes of the electrodes, either as distinct electrodes or as subsets of electrodes. The control circuitry system 132 may be implanted, as part of the implant body 110, implanted as a distinct entity; may be located on a circuit as part of the circuitry system 130, or may be located outside of the body.

The control circuitry system 132 may function autonomously, but may additionally, or alternatively, be controlled by a user through an external remote-control device or communication system. In one implementation, where the implant body 110 is non-conductive, the control circuitry system 132 may allow current to be only applied at the surface of the electrode sites, thus allowing the distribution of current density to be controlled by the placement of the electrodes as well as their state during stimulation. Additionally, or alternatively, the charge, charge density, and/or electric field may be controlled. Alternatively, the electrodes can be conductively isolated from a subset of the other electrodes and more preferably conductively isolated from each of the set of electrodes such that each electrode could be independently controlled such that current density may be similarly controlled by the control circuitry system 132.

In some variations, the system may further comprise a housing attachment (also referred to as a nose). The nose may function as a housing fixed to the implant. The nose may be fixed to the implant body 110, as shown in FIG. 2. The nose may be constructed of non-toxic high durability material. In one variation, the nose is constructed of titanium. In another variation, the nose is constructed of PEEK. The nose may be alternatively constructed of steel, platinum, other non-toxic metals, non-toxic polymers, or any combination. In many variations, the nose may contain some components of the circuitry system 120. Examples of components that may be contained in the nose include, batteries, PCBs (and all components on the PCBS), processors, additional electrodes, antennas, wiring, and/or any other components. In some variations, the nose is connected to the implant such that the nose is welded to the implant body 110. In one implementation a titanium nose is welded to a titanium connector component of the implant body 110, as shown in the schematic drawing of FIG. 12.

Figure 12:
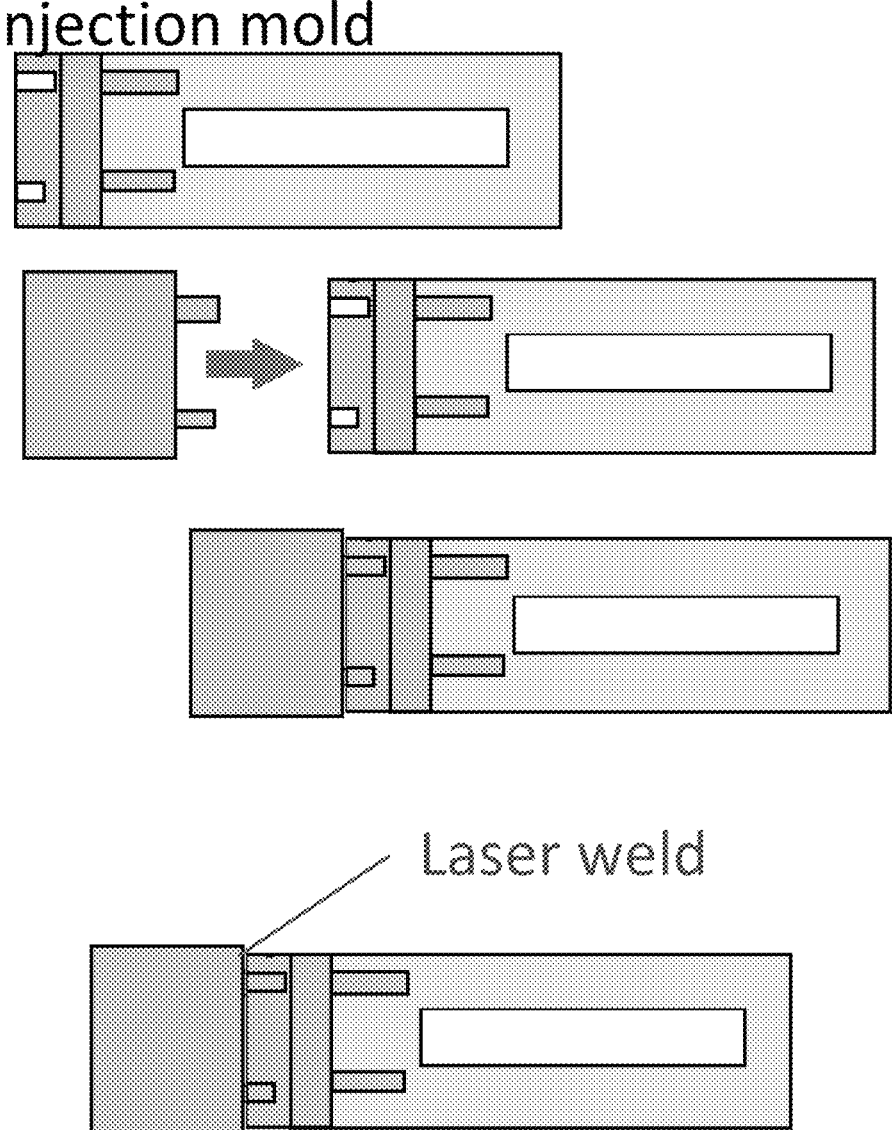
FIG. 12 is a schematic of the construction of a system of a preferred embodiment.
Figure 13:
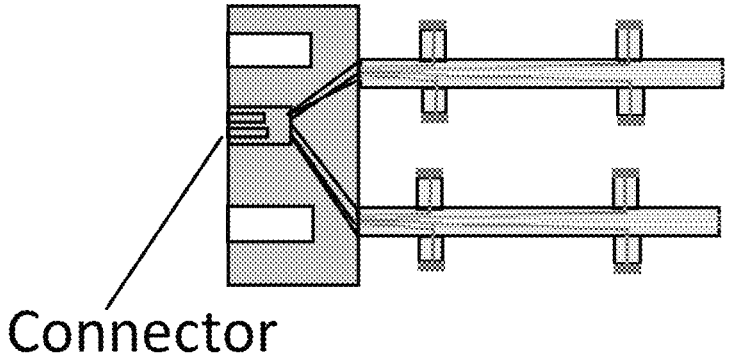
FIG. 13 is a schematic of the implant body flanks and connector.

The spinal cage may be constructed in any general manner. In one implementation, as shown in FIGS. 12 and 13, "flanks" and "connector" of the implant body are constructed, electrodes, antennas, and circuitry components are attached to the flanks and connector; the flank and connector are connected; the flank and connector are then overmolded to create the implant body 110 with embedded circuitry and electrode components; and the nose/housing attachment is then welded to the implant body at the connector. In some variations, the connector is initially constructed, and the flanks are injection molded onto the connector, as shown in FIG. 13. Alternatively, the components are constructed distinctly.

Figure 14:
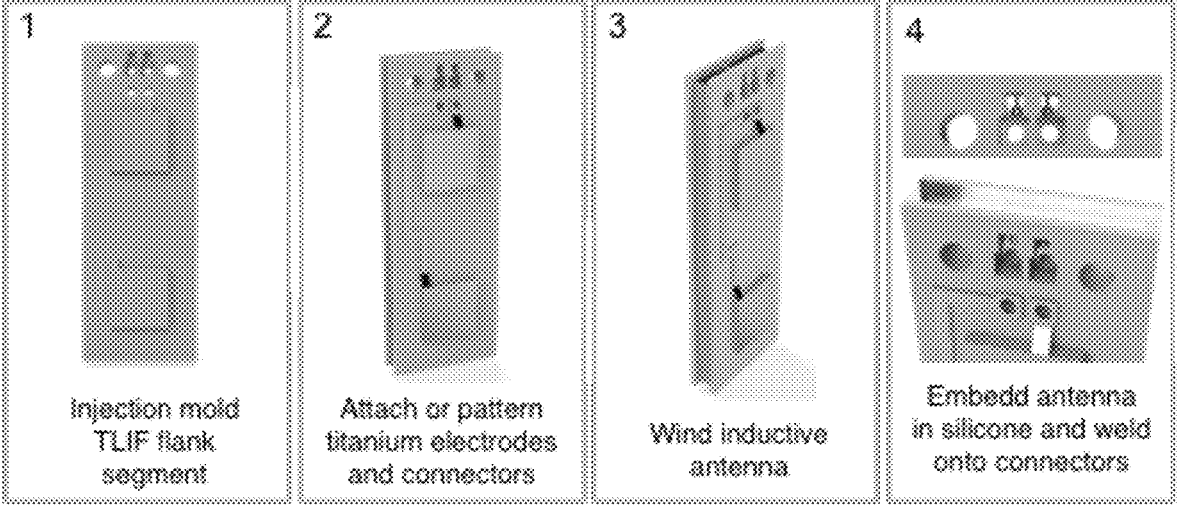
FIG. 14 is an illustration of a production technique for the flank.

In this implementation, as shown in FIG. 14, machine, and/or injection, molding of PEEK is used to create the flanks, wherein the flanks comprise wall-like shape with spacing for circuitry and protrusions for electrode placement. Antennas and other circuitry components in addition to electrodes, may then be wrapped and/or printed onto the flanks. Components may be welded together, and in place as desired. Dependent on implementation, components may be padded, or protected in place using silicone (e.g., filling over the antenna with silicone).

In this implementation, machine, and/or injection, molding is used to construct the connector. The connector comprises a combination of PEEK and titanium material, wherein at least one surface of the connector is titanium. Antennas and other circuitry components in addition to electrodes, may then be wrapped and/or printed onto the flanks. Components may be welded together, and in place as desired.

Figure 15:
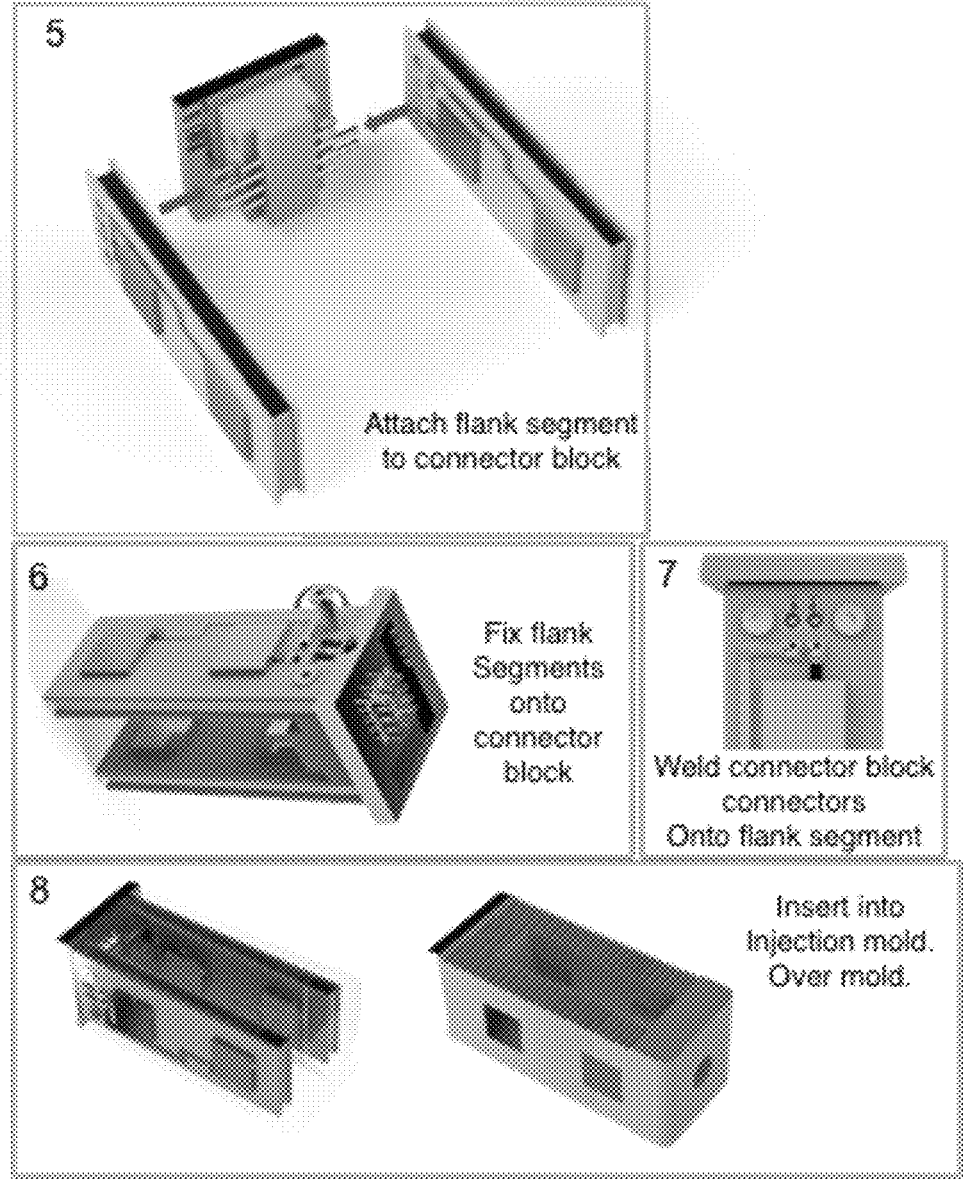
FIG. 15 is an illustration of a production technique for the flank and the connector.
Figure 16:
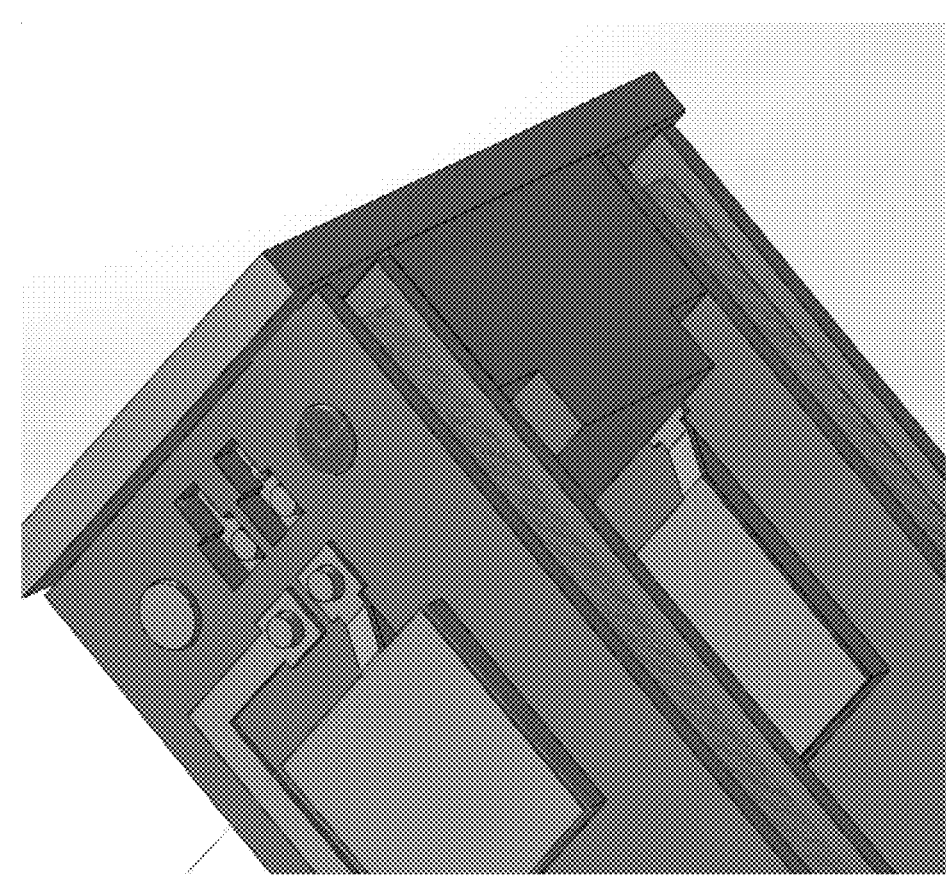
FIG. 16 is an illustration of the flanks and connector components.

In this implementation, the flanks and the connector are combined into a single structure. They may be combined through welding of circuitry components, attachment by screws, as shown in FIGS. 15 and 16. Additionally or alternatively, they may be combined through molding, gluing, or any other desired method.

The flank and the connector structure may then be completed into the implant body 110 through overmolding. Overmolding may give the implant body 110 the desired shape, and desired properties, e.g., side holes, graft window size, implant height.

Figure 17:
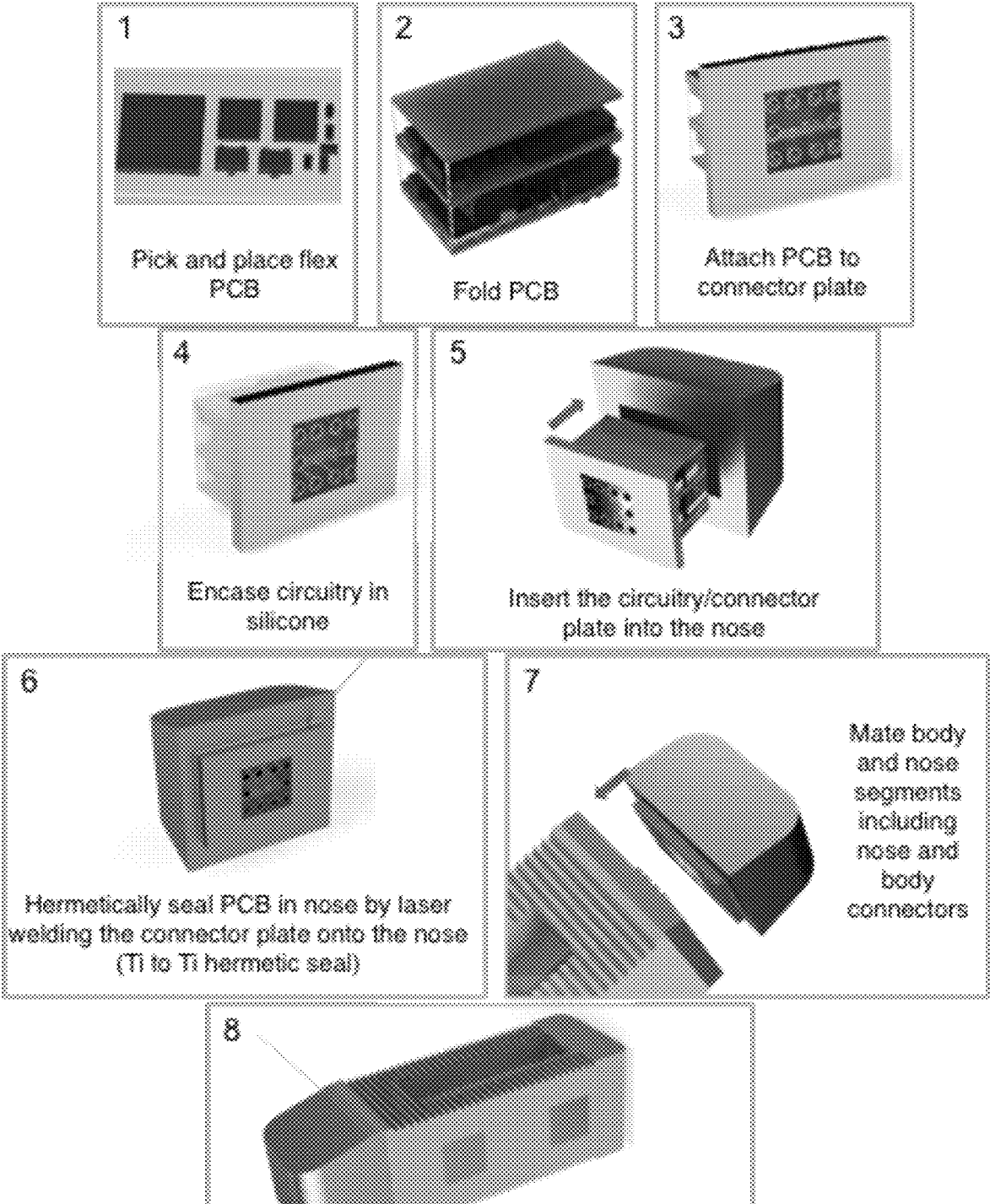
FIG. 17 is an illustration of a production technique for the nosing.
Figure 18:
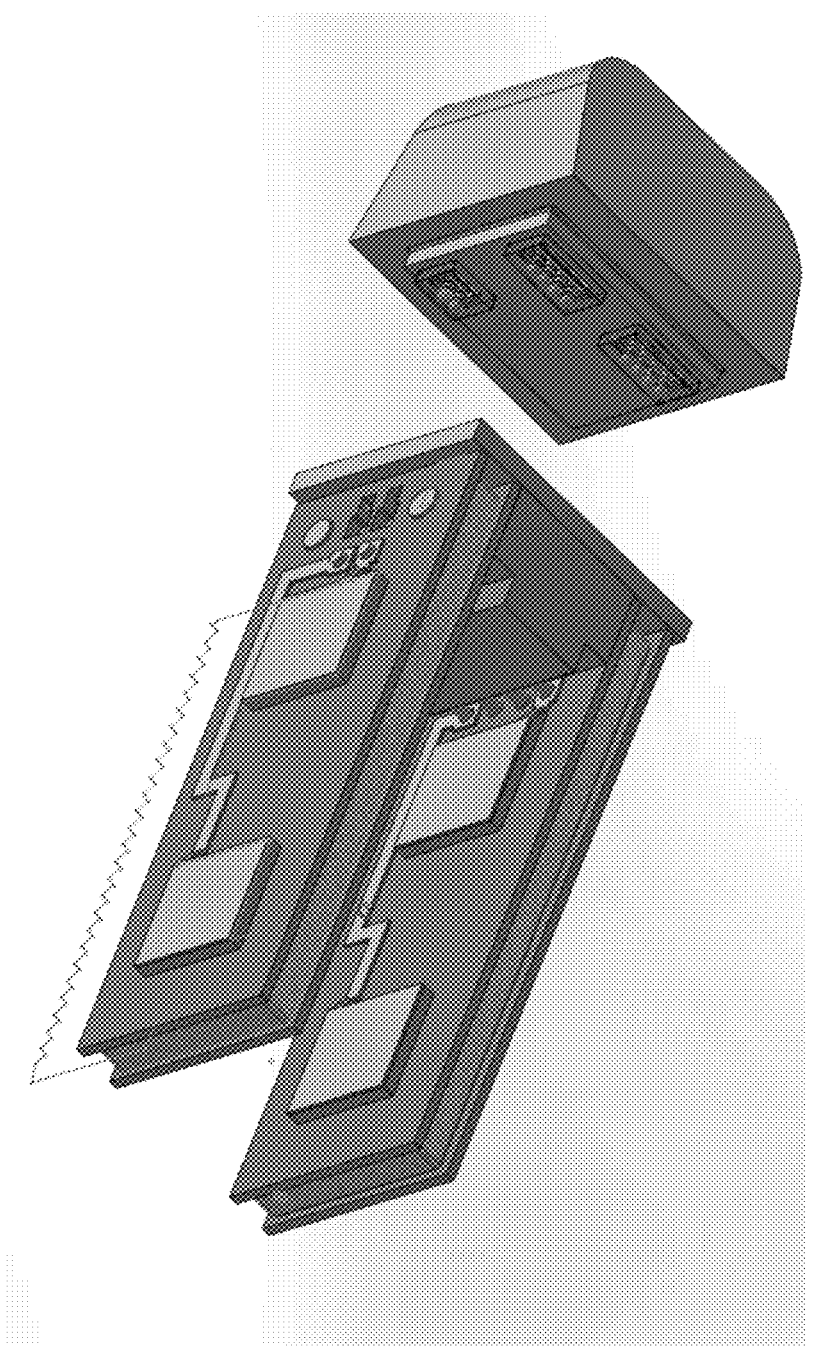
FIG. 18 is an illustration of the implant body and nosing components.

The nosing of the implant may be constructed using a distinct connector component and a nose component as shown in FIG. 17. As shown in this implementation, circuitry components may be directly attached to the connector plate, encased in silicone, and then inserted into the nose component. Once the implant body 110 is constructed, the nosing may then be connected to the implant body, as shown in FIGS. 17, and 18. Connected the nosing may include connecting the appropriate circuitry between the components and welding the nosing on to the implant body 110.

The system preferably has multiple operating modes wherein the control circuitry system 132 is configured to activate the plurality of electrodes 120 to function in specific ways. Preferably, the system includes at least a stimulation operating mode, and a monitoring operating mode. In other preferred variations, the system may include a scaling operating mode. The system may additionally include other operating modes (e.g., a calibration operating mode). Operating modes may function simultaneously, or distinctly, within the entire system and/or within each system subcomponent. For example, in one implementation, the control circuitry system 132 may activate a subset of the plurality of electrodes 120 to operate in a stimulation mode and activate another subset of electrodes to function in a monitoring mode (e.g., an impedance measurement mode).

The system is preferably configured to operate in a stimulation mode. In a stimulation mode, the control circuitry system 132 is configured to activate subsets of the plurality of electrodes 120 to send and receive current through tissue to induce either osteoinduction or osteolysis in the tissue as desired. That is, a subset of the plurality of electrodes are 120 are activated as cathodes and a distinct subset of the plurality of electrodes are activated as anodes. Dependent on the desired amount of stimulation the current may be altered as desired to induce the desired amount of osteoinduction or osteolysis.

The system may also be configured to operate in a monitoring mode. In the monitoring mode, the control circuitry system 132 is configured to utilize electrodes to determine tissue impedance, wherein the tissue impedance may be used to determine the tissue composition. In the monitoring mode, the control circuitry system 132 may activate current through pairs of electrodes thereby measuring the impedance in the tissue between the pair of electrodes. Dependent on implementation, the monitoring mode may work in conjunction, simultaneously, and/or independently of the stimulation operating mode. For simultaneous operation, one pair of subsets of electrodes may operate to provide electric stimulation, while a distinct pair of subsets of electrodes may operate to monitor impedance. Thus, the monitoring mode may be used in conjunction with the stimulation mode to monitor bone growth activity and then alter the bone growth activity as desired, either automatically or after physician approval.

In this manner, the monitoring mode may be used to monitor the bone growth within the bone growth region and regions sufficiently proximal to the implant. Preferably, monitoring bone growth involves the control circuitry system 132 driving AC signals between pairs of electrodes and thus through the intermediary tissue. By measuring the impedance, through the tissue, the relative tissue composition (i.e., amount of bone growth) may be determined. By using this measurement between electrode pairs located on the perimeter of each bone growth region, the control circuitry system 132 may determine the tissue composition of the region. In some variations, multiple distinct pairs of electrodes may be used to measure the impedance region thereby creating an impedance profile of tissue proximal to and within the implant. FIG. 19 shows a sample TLIF cage with eight electrodes (four interior and four exterior) and impedance measurements between the exterior electrodes after implantation of the sample TLIF cage into a sheep. It should be noted that this cage is implanted using a lateral approach, but its shape and dimensions are very similar to a human TLIF cage rather than a lateral cage. In the application of spinal fusion, the impedance profile can be used to monitor the degree of bone growth, and thus determine if spinal fusion has been achieved and determine a fusion rate.

To facilitate high level monitoring through impedance measurements, the implant may include implant bone growth monitoring circuitry which functions to measure bone growth through impedance measurements through the monitoring mode. Bone monitoring in this manner may be beneficial in reducing dependence on more complicated, slow, and expensive monitoring techniques such as MRI, ultrasound or x-rays conducted at a healthcare facility. The optional implant bone growth monitoring circuitry can be used to measure the impedance of the tissue between pairs of one or more electrodes. In this manner impedance measurements may be used to determine the initial bone composition, directly after surgery, and subsequent bone growth over time.

In many spinal fusion implementations, a medical practitioner additionally includes a bone graft in the graft window when installing the implant, wherein the bone graft comprises bone, or bone-like, tissue that functions as a bone growth "seed". Common types of bone grafts include: autografts, bone tissue taken from the patient; allografts (donor/cadaver bone), and synthetics such as ChronOS Strip, bone plugs, synthetic bone filler. As an example of initial bone growth monitoring FIG. 20 shows the impedance measurements after implantation of the sample TLIF cage with autograft, and FIG. 21 shows the impedance measurements after implantation of the sample TLIF cage with ChronOS Strip. In some variations, the system may enable spinal cage preparation validation, wherein impedance measurement may evaluate the preparation of material seeded into the graft window in preparation for a surgery. This may, for example, enable the system to validate that sufficient autograft, CronOS Strips, synthetic bone filler, or other preparation material has been packed within the graft window.

As shown in FIG. 58, a method for operating a spinal cage implant may include providing a spinal cage implant S210 and stimulating the plurality of electrodes during a stimulation mode S230 comprising generating stimulation conditions (in proximity to the spinal cage implant) within a targeted bone growth levels S230. The targeted bone growth levels may be a range of current densities that correspond to enhance bone growth. Accordingly, the method may include providing a spinal cage implant S210 and stimulating the plurality of electrodes during a stimulation mode S230 comprising generating a current density within a targeted range in a select region relative to the spinal cage implant.

In some variations, the stimulation can be spatially calibrated such that at least two different regions can undergo different targeted levels of bone growth. Accordingly, in some variations, the method can include providing a spinal cage implant S210; setting stimulation profile S220 wherein a first region is defined and a second region is defined, wherein the level of bone growth is different between the first and second region; and stimulating the plurality of electrodes during the stimulation mode S230, which can include generating a current density in the first defined region and second defined region according to targeted levels of bone growth. More specifically, a first region could be a targeted osteoinduction region and a second region could be a targeted non-osteoinduction region. For example, the posterior side of a spinal cage implant may be configured as a non-osteoinduction region such that generating the current density in the posterior side of the spinal cage targeted a range outside of targeted current density range (e.g., being outside 1.8-9.1 $\mu$A/cm$^2$ region). On the contrary, a targeted osteoinduction region (inside a graft window for example), may have a current density targeted in the targeted current density range (e.g., being 1.8-9.1 $\mu$A/cm$^2$ in a defined bone contact region).

The method for operating the implant is preferably implemented by the system described herein but may alternatively be implemented by other suitable orthopedic implants. Accordingly, providing the spinal cage implant S210 preferably includes providing or using a spinal cage device such as described herein which may include any of the variations described herein. In some cases, the design features of the device may establish conditions whereby stimulation achieves the targeted levels. In general, the spinal cage implant S210 will be one that includes a spinal cage body that includes at least one defined graft window cavity, a plurality of electrodes exposed on the surface of the spinal cage body, and control circuitry configured to drive the plurality of electrodes in a stimulation mode.

As shown in FIG. 59, in some variations, the spinal cage implant may additionally or alternatively include a monitoring mode. Accordingly, the method may include during a monitoring mode of the spinal cage implant, measuring impedance between at least two electrodes of the plurality of electrodes and thereby collecting an impedance dataset S240.

The impedance dataset may indicate a spatial map of different impedance measurements in the volume around the implant. In some alternative variations, there may be a single impedance measurement. A variation that includes a monitoring mode may additionally include analyzing bone growth based on the impedance dataset S242 and triggering a response based on the analysis S243.

Analyzing bone growth based on the impedance dataset S242 can include detecting a bone formation state when impedance measurements in the targeted osteoinduction reaches 1.2-1.5 kΩ and detecting a non-bone tissue state when the impedance measurement in the targeted non-osteoinduction region is <0.6-0.8 kΩ. Alternative variations, may use other suitable thresholds as described herein.

Triggering the response based on the analysis S243 may include triggering a response based on comparison of the impedance dataset and the targeted levels of bone growth.

In some variations this can include triggering a communication. For example, a data message may be sent to an external device to report on conditions of bone growth under certain situations like when bone growth in a certain region has met threshold, when bone growth is occurring where it should not, and/or other conditions.

In another variation, the response could include updating a stimulation profile or otherwise adjusting changes to stimulation. In some cases, this may include modeling desired changes and updating electrode state during stimulation mode. This may account for the geometry of the implant, implant design features like side-holes, magnitude of predicted bone growth, and other variations described herein. Updating the stimulation in some situations may include deactivating or activating subsets of electrodes to steer the current density towards or away select regions.

3. Examples

The system variations above can be applied in designing and/or operation a specialized stimulation-enabled spinal cage. In this section, different exemplary variations are described along with data on expected level of growth/stimulation. These exemplary variations are used to illustrate application of the features of the system and method to calibrate stimulation for enhanced performance. However, one skilled in the art would appreciate that the system and method are not limited to only these exemplary variations.

Examples herein are presented for TLIF cages, initially based on in-vivo measurements in sheep, which are then used to present model lateral cages, and ALIF cages, with similar desired growth. As an overview of this section: A TLIF cage in-vivo example is presented in FIG. 22; which is then matched to a TLIF cage model example; variations of the TLIF cage model are explored in FIGS. 23-31. In FIGS. 32-41 lateral cage model examples are presented that scale to match the TLIF cage model. In FIGS. 42-44 ALIF cage model examples are presented that scale to match the TLIF cage model. These examples implement system variations in fitting a system design to stimulation models using variations such as electrode sizing, implant height, electrode polarity arrangement, separators, integration of side holes on the implant, and/or other variations.

Figure 56:
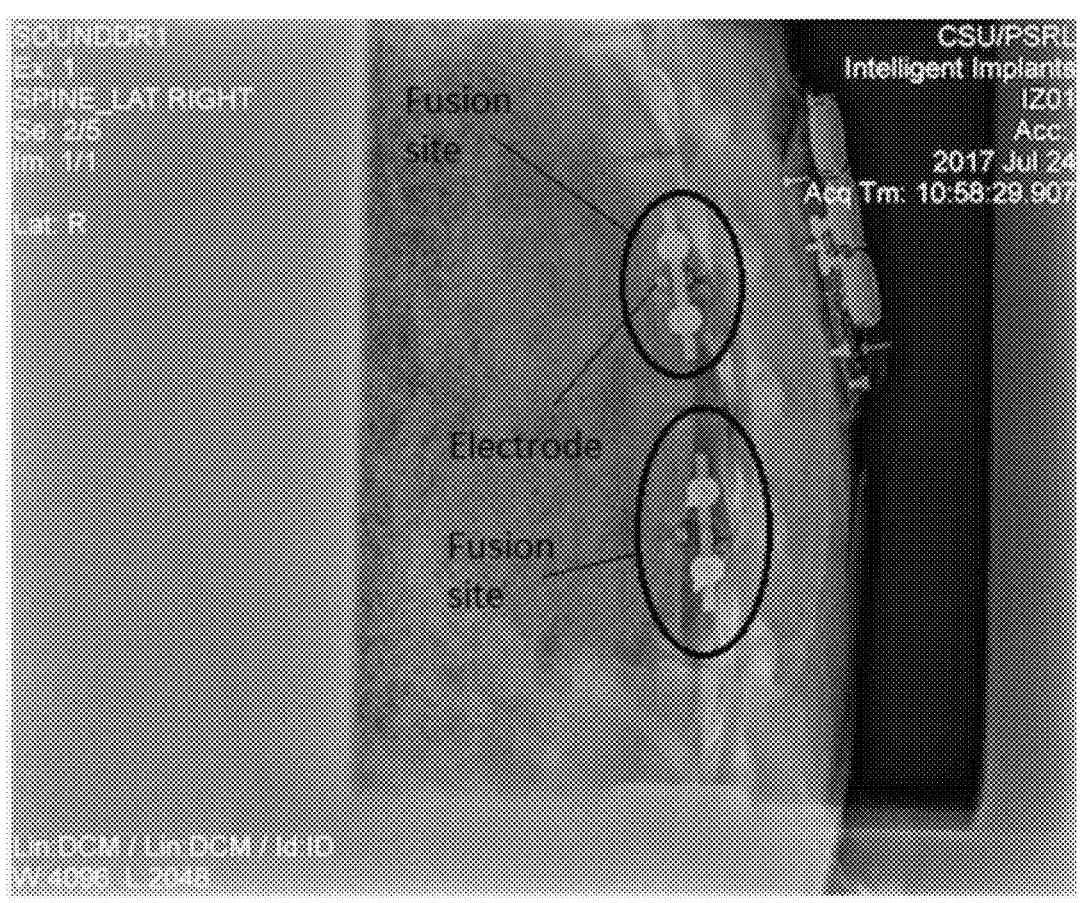
FIG. 56 is an image showing two implant cages in a sheep.

FIG. 56 shows an implementation of two TLIF cages in a sheep. As shown in FIG. 22, an in-vivo implementation of a TLIF cage, showing the current density (top) and potential (bottom), the TLIF cage may promote bone growth in the interior of the cage, and preferably bone growth near the external electrodes, while promoting no bone growth further away from the cage. The TLIF cage is a 10 mm tall TLIF cage with: a single graft window; four electrodes along the interior perimeter functioning of the implant body 110, four electrodes along the exterior perimeter of the implant body, wherein the eight electrodes all function as cathodes; a single electrode distal to the implant functioning as an anode; three side holes, one on the posterior side of the implant body 110 (facing towards the spinal cord), one on the anterior side of the implant body (facing the belly), and one on an end of the implant body opposite the main circuitry components. Such an exemplary variation of the system and its use in in-vivo experimentation, may be used as a model for extrapolating to alternative cage implant configurations with enhanced stimulation and/or monitoring capabilities.

As shown in FIG. 24, a model implementation of a TLIF cage, wherein the stimulation is matched to the in-vivo, with stimulation between 15-25 μA, showing the current density (top) and potential (bottom), the TLIF cage may promote bone growth in the interior of the cage, possible bone growth near the external electrodes, while promoting no bone growth further away from the cage, in agreement with the in-vivo example. The model TLIF cage is a 9 mm tall TLIF cage with: a single graft window; four electrodes along the interior perimeter functioning of the implant body 110, four electrodes along the exterior perimeter of the implant body, wherein the eight electrodes all function as cathodes; a single electrode distal to the implant functioning as an anode; three side holes, one on the posterior side of the implant body 110, one on the anterior side of the implant body, and one on an end of the implant body opposite the main circuitry components. Using the geometry of the model TLIF cage and conductance of material determined from the in-vivo implant, impedance measurements may be made between electrodes, as shown in FIG. 25; wherein the bar graph shows impedance measurements across the graft window (i.e., position I to position II) for different types of implemented graft material, having different densities.

Variations of the model implementation may be used to identify different regions and types of potential stimulation. As shown in FIG. 26, a model implementation of a TLIF cage, wherein the stimulation is matched to the in-vivo implant, with stimulation between 10-20 μA, showing the current density (top) and potential (bottom), the TLIF cage may promote the same bone growth in the interior of the cage, with some bone growth outside the implant. The model TLIF cage is a 9 mm tall TLIF cage with: a single graft window; four electrodes along the interior perimeter of the implant body 110, four electrodes along the exterior perimeter of the implant body, wherein the eight electrodes all function as cathodes; the "nose" of the implant functioning as a single electrode anode; and three side holes, one on the posterior side of the implant body 110, one on the anterior side of the implant body, and one on an end of the implant body opposite the nose of the implant.

Variations of the model implementation may include additional (or removal) of electrodes. As shown in FIG. 28, a model implementation of a TLIF cage, wherein the stimulation is matched to the in-vivo implant, with stimulation between 5-15 μA, showing the current density (top) and potential (bottom), the TLIF cage may promote some bone localized growth in the interior of the cage, with no (or minimal) bone growth outside the implant. The model TLIF cage is a 9 mm tall TLIF cage with: a single graft window; four electrodes along the interior perimeter of the implant body 110 functioning as cathodes; an electrode on a shorter wall of the interior perimeter as a single electrode anode; and three side holes, one on the posterior side of the implant body 110, one on the anterior side of the implant body, and one on an end of the implant body opposite the nose of the implant.

Variations of the model may include fewer side holes to help localize current in the interior of the implant. As shown in FIG. 27, a model implementation of a TLIF cage, wherein the stimulation is matched to the in-vivo showing the current density (top) and potential (bottom), the TLIF cage may promote bone growth in the interior of the cage, preferably bone growth near the external electrodes with less growth towards the posterior, while promoting no bone growth further away from the cage. The model TLIF cage is a 9 mm tall TLIF cage with: a single graft window; four electrodes along the interior perimeter of the implant body 110, four electrodes along the exterior perimeter of the implant body, wherein the eight electrodes all function as cathodes; a single electrode distal to the implant functioning as an anode; and one side hole on the anterior side of the implant body 110.

Additionally, cathode and anode positioning may be optimized in conjunction with a single side hole. As a second example, as shown in FIG. 29, of a model implementation of a TLIF cage, wherein the stimulation is matched to the in-vivo implant, wherein the stimulation current is set between 7.00-11.00 μA, showing the current density (top) and potential (bottom), the TLIF cage may promote bone growth in the interior of the cage, and a reduced possibility of bone growth on the posterior exterior of the implant as compared to the previous model. This model TLIF cage is a 9 mm tall TLIF cage with: a single graft window; four electrodes along the interior perimeter functioning as cathodes, two electrodes along the exterior anterior of the implant body functioning as anodes; and one side hole on the posterior side of the implant body 110. Positioning of the two exterior anode electrodes on the anterior side may mitigate bone growth on the posterior side, external to the implant.

Removing all side holes may function to further localize bone growth. As shown in FIG. 30 of a model implementation of a TLIF cage, wherein the stimulation is matched to the in-vivo implant, wherein the stimulation current is set between 5-9 μA, showing the current density (top) and potential (bottom), the TLIF cage may promote concentrated bone growth in the interior of the cage and a reduced possibility of bone growth exterior of the implant. This model TLIF cage is a 9 mm tall TLIF cage with: a single graft window; four electrodes along the interior perimeter functioning as cathodes, two electrodes along the exterior anterior of the implant body functioning as anodes; and no side hole.

In some variations, different heights of the implant may be implemented. As a similar example to the prior example, as shown in FIG. 31, of a model implementation of a TLIF cage, wherein the stimulation is matched to the in-vivo implant, wherein the stimulation current is set between 4-8.52 μA, showing the current density (top) and potential (bottom), the TLIF cage may show bone growth activity similar to the prior example. This model TLIF cage is a 13 mm tall TLIF cage with: a single graft window; four electrodes along the interior perimeter functioning as cathodes, two electrodes along the exterior anterior of the implant body functioning as anodes; and no side hole.

Figure 33:
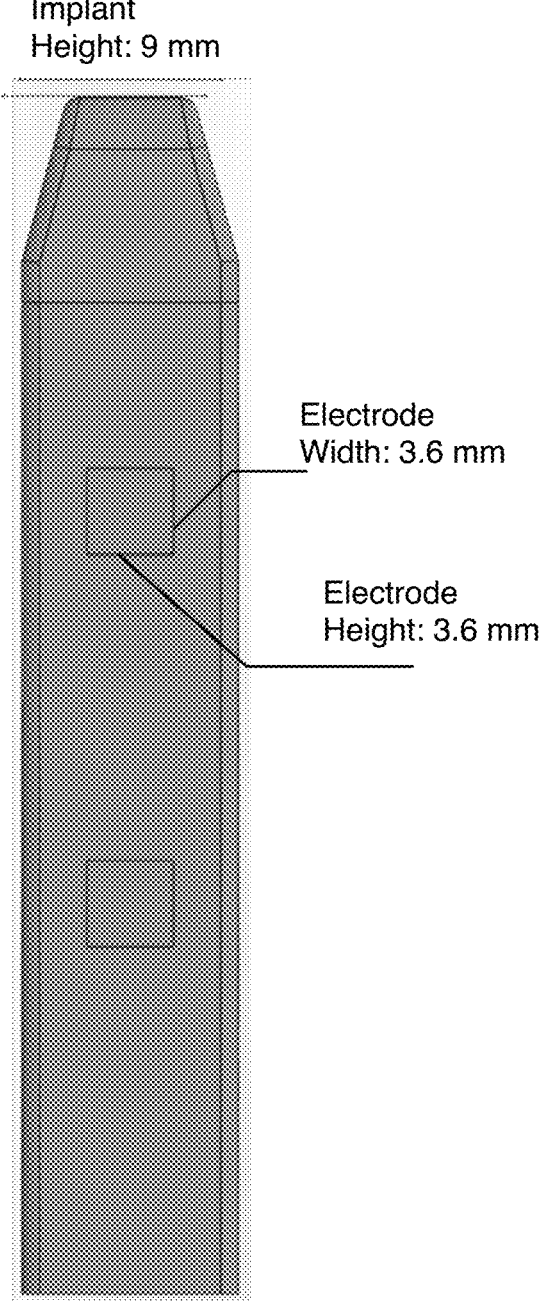
FIG. 33 is a schematic diagram of a model lateral cage.

Variations of the TLIF model implementation may be used to scale the in-vivo implementation for utilization of different size spinal cages. The lateral cage may be modeled as shown in FIGS. 32-34. As shown in FIG. 35, a model implementation of a lateral cage, wherein the stimulation is matched to the in-vivo showing the current density (top) and potential (bottom), the lateral cage may promote bone growth only proximal to each cathode electrode, with minimal growth throughout the interior of the graft window; significantly less than the TLIF model. This model lateral cage includes: a single graft window; four electrodes along the interior perimeter of the implant body 110, four electrodes along the exterior perimeter of the implant body, wherein the eight electrodes all function as cathodes; a single electrode distal to the implant functioning as an anode, and one side hole on an end of the implant body opposite the main circuitry components. Using the geometry of the lateral cage and conductance of material determined from the in-vivo implant, impedance measurements may be made between electrodes, as shown in FIG. 36; wherein the bar graph shows impedance measurements across the graft window (i.e., position I to position II) for different types of implemented graft material, having different densities (conductivity).

With scaling implementation of the lateral cage, bone growth behavior may be brought closer to the TLIF model. Electrode size may be scaled with the size of the implant as shown in FIG. 37. As shown in FIG. 38, a model implementation of a lateral cage, wherein the electrodes are scaled larger and the stimulation density is matched to the in-vivo example, wherein the stimulation ranges from 50-90 μA, showing the current density (top) and potential (bottom), the lateral cage may promote better bone growth in the graft window as compared to the first lateral cage example but less than the TLIF model, with some growth on the exterior. This model lateral cage includes: a single graft window; four large electrodes along the interior perimeter of the implant body 110, four large electrodes along the exterior perimeter of the implant body, wherein the eight electrodes all function as cathodes; a single electrode distal to the implant functioning as an anode, and one side hole on an end of the implant body opposite the main circuitry components. It should be noted that in some implementations, the model implant may also include "small" (i.e., unsealed) electrodes. These smaller electrodes may have a specific use, e.g., for impedance measurements.

Scaling implementation of the lateral cage may be further improved by scaling the graft window. As shown in FIG. 39, a model implementation of a lateral cage, wherein a separator divides the graft window, electrodes are scaled larger, and the stimulation density is matched to the in-vivo example, the lateral cage may promote better bone growth in the graft window as compared to the first lateral cage example but less than the TLIF model, with some growth on the exterior. This model lateral cage includes: two "half-sized" graft windows divided by a separator; four large electrodes along the interior perimeter of the implant body 110, four large electrodes along the exterior perimeter of the implant body, wherein the eight electrodes all function as cathodes; a single electrode distal to the implant functioning as an anode, and one side hole on an end of the implant body opposite the main circuitry components.

Scaling implementation of the lateral cage may be even further improved by scaling the electrode spacing. As shown in FIG. 40, a model implementation of a lateral cage, wherein a separator divides the graft window with two additional electrodes along the separator, electrodes are scaled larger, and the stimulation density is matched to the in-vivo example, the lateral cage may promote better bone growth similar to the TLIF model, with potential bone growth in the interior of the graft windows and some growth on the exterior of the implant body 110. This model lateral cage includes: two "half-sized" graft windows divided by a separator; six large electrodes along the interior perimeter of the implant body 110, four large electrodes along the exterior perimeter of the implant body, wherein the eight electrodes all function as cathodes; a single electrode distal to the implant functioning as an anode, and one side hole on an end of the implant body opposite the main circuitry components.

Once scale has been matched to the TLIF model, improved growth functionality may be incorporated with anode electrodes on the posterior of the implant body 110. As shown in FIG. 41, a model implementation of a lateral cage, wherein a separator divides the graft window with two additional electrodes along the separator, electrodes are scaled larger, and the stimulation density is matched to the in-vivo example, the lateral cage may promote bone growth in the interior of the graft windows and no bone growth on the posterior side of the implant, similar to the TLIF model with posterior anodes. This model lateral cage includes: two "half-sized" graft windows divided by a separator; eight large electrodes along the interior perimeters of the implant body 110, wherein the eight electrodes all function as cathodes; and two large electrodes on exterior anterior perimeter of the implant as anodes.

Variations of the TLIF model implementation may also be used to scale ALIF cages. As shown in FIG. 42, a model implementation of an ALIF cage, wherein the stimulation is matched to the in-vivo example showing the current density (top) and potential (bottom), the ALIF cage may promote minimal growth throughout the interior of the graft window; significantly less than the TLIF model. This model ALIF cage includes: two graft windows; four electrodes along the interior perimeters of the implant body 110, four electrodes along the exterior perimeter of the implant body, wherein the eight electrodes all function as cathodes; a single electrode distal to the implant functioning as an anode, and one side hole on an end of the implant body opposite the main circuitry components.

As shown in FIG. 43, the scaling of the model ALIF cage may be improved by scaling to larger electrodes and including additional electrodes along the interior graft window perimeters. In this model implementation of an ALIF cage, wherein the stimulation current density is matched to the in-vivo example, showing the current density (top) and potential (bottom), the ALIF cage may promote some growth throughout the interior of the graft windows but less than the TLIF model. This model ALIF cage includes: two graft windows; six electrodes along the interior perimeters of the implant body 110, two electrodes along the exterior perimeter of the implant body, wherein the eight electrodes all function as cathodes; and a single electrode distal to the implant functioning as an anode.

As shown in FIG. 44, the scaling of the model ALIF cage may be modified to function to prevent all posterior growth by using posterior side anodes. In this model implementation of an ALIF cage, wherein the stimulation current density is matched to the in-vivo example, showing the current density (top) and potential (bottom), the ALIF cage may promote similar growth to the TLIF model with posterior electrode anodes. This model ALIF cage includes: two graft windows; six electrodes along the interior perimeters of the implant body 110 functioning as cathodes; and a single electrode on the anterior exterior perimeter of the implant functioning as an anode.

To summarize the example section, implants may be scaled to demonstrate similar activity by: scaling electrode sizes with the size of the implant, choosing of an appropriate current density determined from in-vivo measurements; matching graft window sizes through the addition (or removal) of separators, and the addition (or removal) of electrodes along the interior perimeter of the implant. Additionally, incorporation of anode electrodes on the posterior/anterior may alter exterior bone growth by reducing the possibility of bone growth on the posterior exterior of the implant.

4. Method for Implant Design

As shown in FIG. 45, a method for scaling orthopedic implant electric activity for different types of implants comprising: for an in-vivo implant, measuring the electric activity of the in-vivo implant S110; for an in-vivo model, modeling the in-vivo implant S120; for a target model, matching the electric activity of the in-vivo model S130. The method functions to enable desired electric activity in a target model (and thus a target implant) using data from another implant. Desired electric activity may include electric stimulation (e.g., to promote bone growth) and impedance measurements in proximity of the implant. This method is particularly applicable to spinal fusion implants, such as presented in the system above, but may be applied to any orthopedic implant that provides electric stimulation. The method preferably implements a model-based design approach for orthopedic implants using electrical stimulation and specifically, model-based design approach for spinal cages. Design ranges, parameters, and configurations determined through the method may also be applied and implemented in a system such as the one described above.

For a spinal fusion implant, wherein the desired electric activity is to promote bone growth such that the implant fuses vertebrae together, the method may enable the scaling and implementation of a tested dose-response curve such that the implant promotes optimal growth. Additionally, the method enables scaling of impedance measurements to identify tissue composition. That is, impedance measurements made through known tissue (e.g., cadaver bone) using a known geometry may be scaled to other geometries for tissue identification.

Bone growth may be stimulated by current, electric fields, or any other forms of active charge. As discussed in this document, electric activity will be primarily presented in the form of current and current densities for consistency; but all information may be equally presented using charge, charge density, electric fields, electric fluxes, or other equivalent description.

Block S110, which includes: for an in-vivo implant, measuring the electric activity of the in-vivo implant, functions to create a baseline of desired implant activity and to determine desired stimulation for bone growth. Block S110 includes measuring bone growth activity during electric stimulation of the in-vivo implant.

Figure 48:
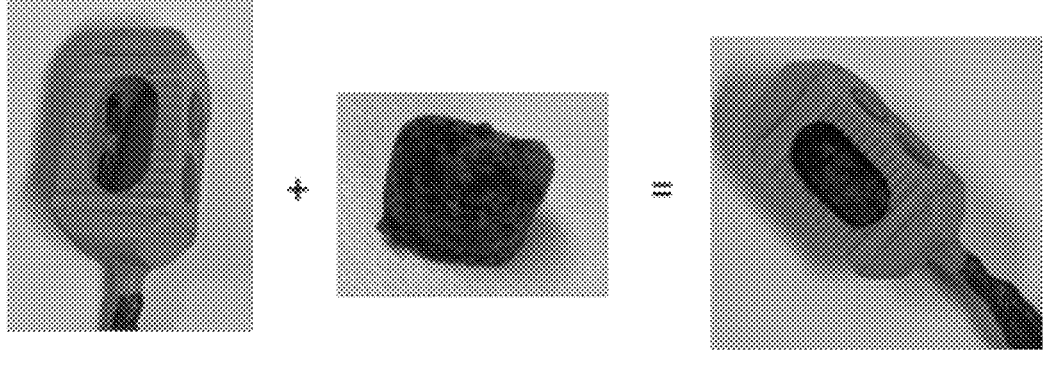
FIG. 48 is a picture of cadaver tissue measurement within a TLIF cage.
Figure 49:
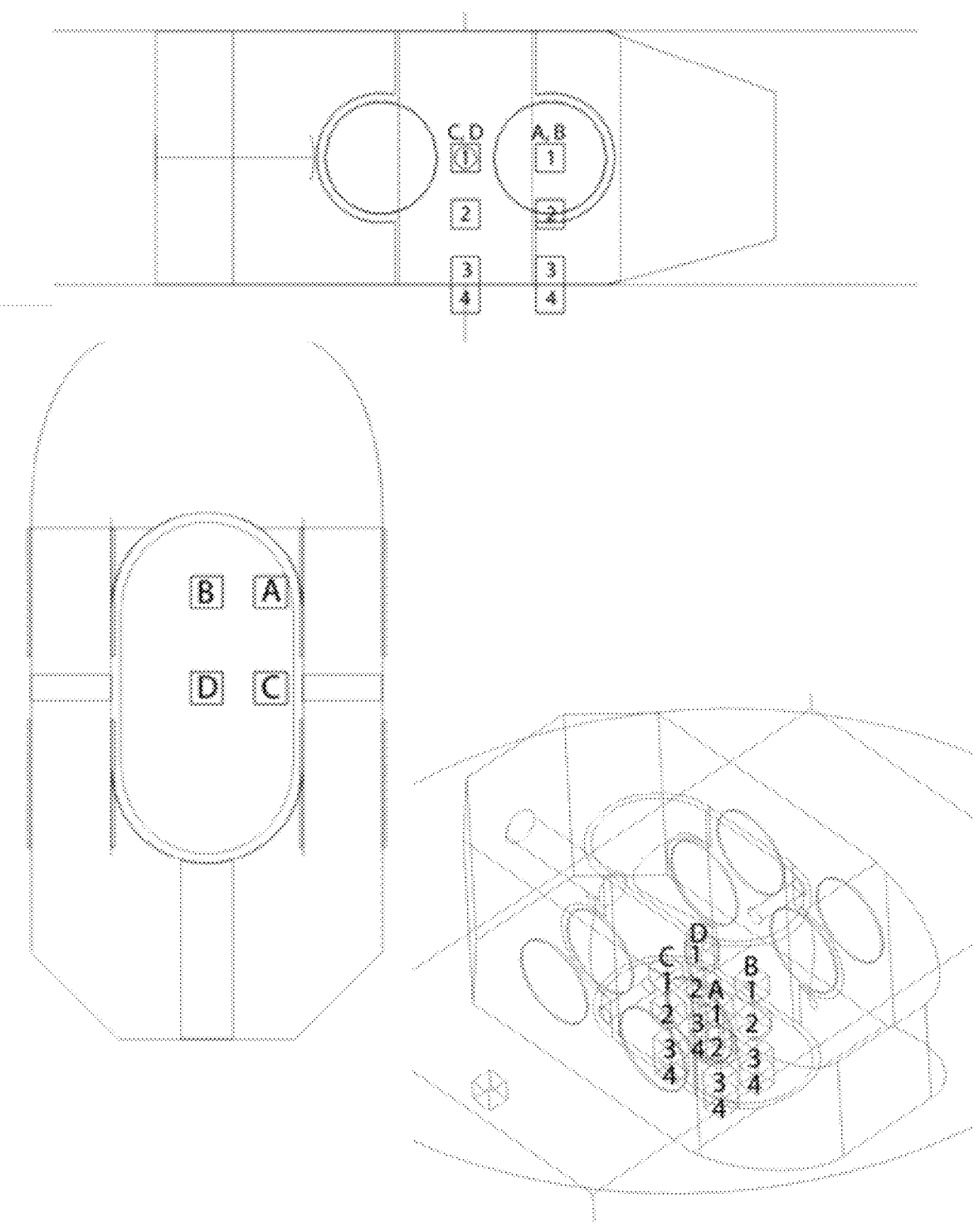
FIG. 49 is a schematic of implant models.

As part of measuring bone growth with respect to electric stimulation a dose-response curve is preferably created. An example dose-response curve, as shown in FIG. 46, may show levels of bone growth as a function of current, wherein this dose-response curve was determined from in-vivo TLIF cages in sheep as shown in FIGS. 48 and 49 (measurements are provided top in FIG. 23). As per this example, the dose-response curve shows the optimal current range for growth is between 8 μA-20 μA. In one implementation, used to generate the curve shown in FIG. 46, the dose response curve was determined by implanting TLIF cages (Shown in FIGS. 48-49, top of FIG. 23) between L2-L3 and between L4-L5 in skeletally mature sheep using a lateral approach, as shown in FIG. 56. One was implanted for stimulation, that stimulated at a fixed stimulation current, and the other was implanted without providing stimulation (same graft, levels were interleaved such that electrostimulating implants were implanted in L2-L3 in one animal and then L4-L5 in the next and so on). Six weeks after implantation spines were extracted and microCTs were performed. Using these microCTs a number of metrics including BV/TV of the volume inside the graft window were calculated. The change in the dose response curve are deltas of BV/TV between the volume inside the graft window of the implant that stimulated vs the implant that did not stimulate, within the same sheep. In other implementations, the dose response curve may show optimal growth in ranges between 3 µA-25 µA and include implantations and stimulations between other vertebrae.

Figure 50:
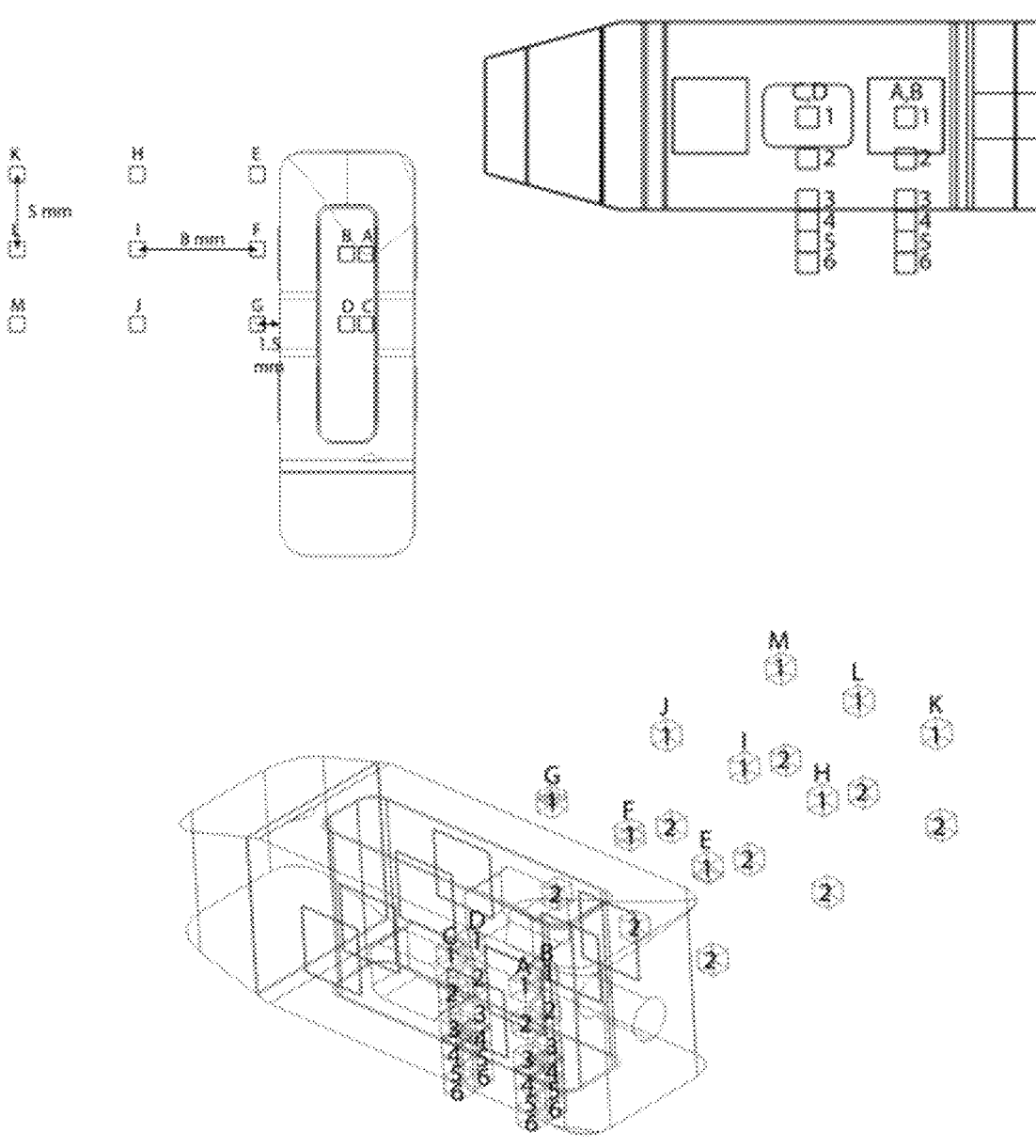
FIG. 50 is a schematic of implant models.
Figure 51:
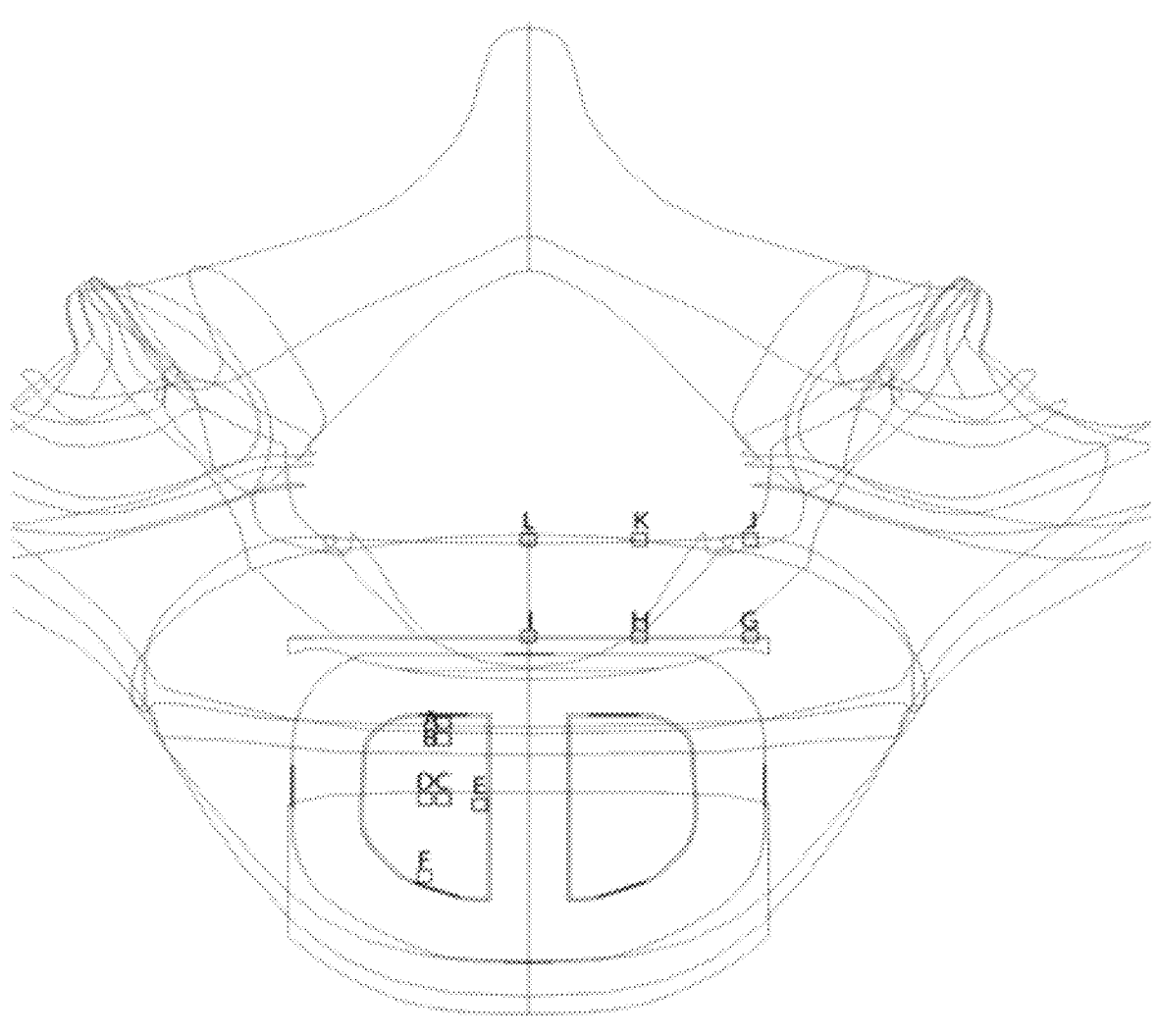
FIG. 51 is a schematic of an ALIF cage implant model.
Figure 52:
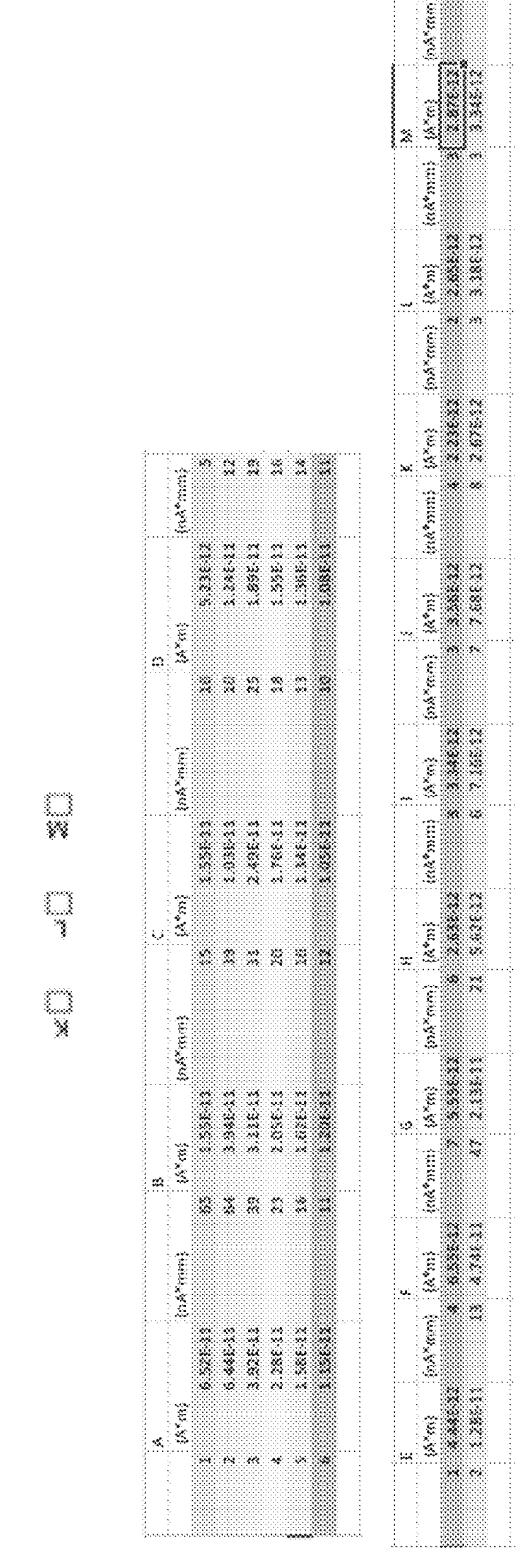
FIG. 52 is stimulation data for a TLIF cage implant model.
Figure 53:
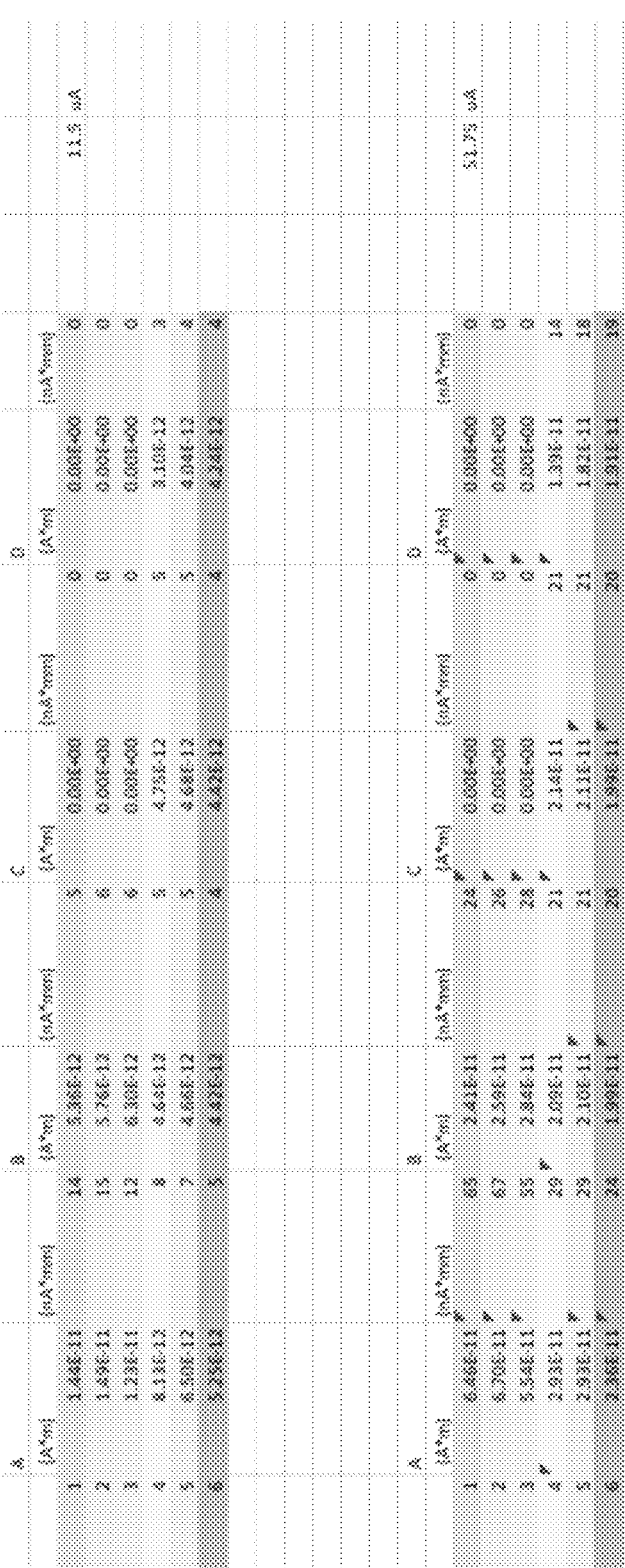
FIG. 53 is stimulation data for a lateral cage implant model.

Block S120, which includes: for an in-vivo model, modeling the in-vivo implant, functions to create a representative model of the in-vivo implant, wherein the in-vivo model accurately replicates the electrical activity of the implant. Modeling the in-vivo implant S120 preferably includes creating sufficiently identical geometrical representation of the in-vivo implant and for a given electric activity at electrode sites on the implant, matching electrical activity (e.g., current density) at spatial points within and around the implant and model. FIG. 49 shows different types of model implants, wherein the cubes represent spatial points to match the models, wherein the '3' and '4' (e.g., A3, B4) represent points on and below the endplate. FIGS. 50 and 51 show different types of model implants with the spatial points extending out of the model implant towards what would be the posterior region of the implant (e.g., towards the spinal cord for a spinal fusion implant). FIG. 52 shows an example TLIF in-vivo model with stimulation matched to an in-vivo implant.

In addition to matching the stimulation activity of the in-vivo implant, block S120 may include matching the impedance activity. That is, in-vitro and in-vivo measurements of tissue resistance, as shown in FIG. 47 may be incorporated into the in-vivo model.

Block S130, which includes: for a target model, matching the electrical activity of the in-vivo model, functions to scale the desired activity determined from the in-vivo implant to a target model, and thus to a target implant. For a spinal fusion implant, block S130 enables utilizing the dose-response curve to promote optimal growth and fusion in a target implant of different size and/or shape.

Matching the electric activity of the in-vivo model S130, may include scaling the target model. Scaling the target model functions to impose additional restrictions on the target implant geometry and stimulation to better match the in-vivo model. For a spinal fusion implant, scaling the target model may include scaling electrodes, scaling graft windows, and scaling current stimulation.

Scaling the target implant may include scaling electrodes. Scaling electrodes functions to adjust the electrode size with the respect target model size. For example, for a TLIF cage in-vivo model and a lateral cage target model, which is roughly twice as large as the TLIF cage; scaling the electrode size may comprise, roughly, doubling the size of each electrode. Additionally or alternatively, more electrodes may be added. In addition to larger electrodes scaling the electrodes may include matching the current density of the in-vivo model. In this manner, doubling the electrode size may increase the current through an electrode, while still maintaining the same current density as the in-vivo model. A dose-response stimulation of the target model would thus match the current density of the in-vivo model and not the current measured through the in-vivo implant.

For a spinal fusion implant, scaling the target implant may additionally include scaling the graft window. Scaling the graft window size and scaling the graft window stimulation. Scaling the graft window size may comprise scaling the area and/or volume of the graft window to roughly match the graft window area and/or volume of the in-vivo model graft window. Graft window size may be modified by designing/modeling novel graft windows for distinct implant models, adding separators to split graft windows, or filling in the volume of a graft window. In some variations more (or fewer) graft windows are created by scaling the graft window size (e.g., one graft window may be divided into three graft windows by the addition of two separators). Scaling the graft window stimulation may comprise adding/removing electrodes, and/or increasing/decreasing electrode area within the graft window. As part of the example, TLIF in-vivo model to lateral cage target model, scaling the graft window may comprise adding a separator to the lateral cage graft window, thereby dividing the graft window into two distinct new graft windows; and adding an extra electrode to each new graft window.

Scaling currents may include adjusting the total current sourced and sinked through electrodes to match the optimal electrical activity derived from the TLIF in-vivo model. Examples of currents (not stimulus currents) within different regions of interest (spatial sampling points) around an implant are provided in FIGS. 52-55. These can be calculated for each implant geometry and implant stimulus current can be adjusted until the electrical activity in the regions of interest align with those found optimal in the in-vivo TLIF model, effectively creating a bone growth dose response curve for an arbitrarily shaped cage or geometry.

Matching the in-vivo model may include scaling the impedance measurements of the in-vivo model. To utilize impedance measurements of known tissue for a target model, the geometry of the target model must be taken into account (i.e., distance between electrodes). Scaling the impedance measurements thus comprises calculating a conductivity from the in-vivo implant and implementing the conductivity into the target model. FIGS. 25 and 36 show impedance values derived from identical conductivity values but different implant geometry. Scaling of the impedance measurements may then be used in classifying and characterizing impedance measurements such as for the purposes of reporting bone growth and/or decay. Modeling of conductivity, the impedance measurements corresponding to bone growth and/or decay of one device design can be translated to a second device design.

As used herein, first, second, third, etc. are used to characterize and distinguish various elements, components, regions, layers and/or sections. These elements, components, regions, layers and/or sections should not be limited by these terms. Use of numerical terms may be used to distinguish one element, component, region, layer and/or section from another element, component, region, layer and/or section. Use of such numerical terms does not imply a sequence or order unless clearly indicated by the context. Such numerical references may be used interchangeable without departing from the teaching of the embodiments and variations herein.

As a person skilled in the art will recognize from the previous detailed description and from the figures and claims, modifications and changes can be made to the embodiments of the invention without departing from the scope of this invention as defined in the following claims.

We claim:

1. A system for spinal fusion comprising:

a spinal cage body that includes at least one defined graft window cavity;

a plurality of electrodes exposed on the surface of the spinal cage body;

control circuitry configured to drive the plurality of electrodes in a stimulation mode;

wherein there is at least a targeted osteoinduction region and a targeted non-osteoinduction region that are immediately adjacent to the spinal cage body;

wherein the control circuitry includes configuration to excite the plurality of electrodes during the stimulation mode for generation of a current density in the targeted osteoinduction region and targeted non-osteoinduction region according to targeted levels of bone growth; and wherein the control circuitry includes further configuration of an impedance mode, wherein impedance measurements can be made between at least two electrodes of the plurality of electrodes to form an impedance dataset, and wherein control circuitry is further configured to trigger a response based on comparison of the impedance dataset and the targeted levels of bone growth, wherein configuration to trigger the response based on comparison of the impedance dataset and targeted levels of bone growth comprises configuration to detect a bone formation state when impedance measurements in the targeted osteoinduction region reaches 1.2-1.5 kΩ and detect a non-bone tissue state when the impedance measurement in the targeted non-osteoinduction region is less than 0.6-0.8 kΩ.

2. The system of claim 1, wherein the targeted osteoinduction region includes the defined graft window cavity, wherein the configuration to excite the plurality of electrodes further includes configuration to generate, in the graft window cavity within one millimeter of a defined endplate surface of the spinal cage body, an average current density between 1.8-9.1 $\mu A/cm^2$ and a current density in the targeted non-osteoinduction region below 1.8 $\mu A/cm^2$ when in the stimulation mode.

3. The system of claim 1, wherein a subset of electrodes includes electrode surfaces exposed on the spinal cage body adjacent to the targeted osteoinduction region, where the size of the electrode surfaces is calibrated to generate current density within an osteoinduction threshold range.

4. The system of claim 1, wherein the plurality of electrodes comprises at least one anode electrode configured in connection with the control circuitry for excitation as an anode, wherein the at least one anode electrode is positioned on the spinal cage body based on position of the targeted non-osteoinduction region.

5. The system of claim 1, wherein the plurality of electrodes comprises a set of cathode electrodes configured in connection with the control circuitry for excitation as cathodes, wherein the set of cathode electrodes are positioned on the implant body based on position of the targeted osteoinduction region relative to the spinal cage body.

6. The system of claim 5, wherein at least two cathode electrodes are exposed along internal walls adjacent to the defined graft window cavity.

7. The system of claim 5, wherein the targeted osteoinduction region is adjacent to a subregion of an external wall of the spinal cage body; and wherein one cathode electrode is exposed in the subregion of the external wall.

8. A system for spinal fusion comprising:

a spinal cage body that includes at least one defined graft window cavity;

a plurality of electrodes exposed on the surface of the spinal cage body;

control circuitry configured to drive the plurality of electrodes in a stimulation mode;

wherein there is at least a targeted osteoinduction region and a targeted non-osteoinduction region that are immediately adjacent to the spinal cage body;

wherein the control circuitry includes configuration to excite the plurality of electrodes during the stimulation mode for generation of a current density in the targeted osteoinduction region and targeted non-osteoinduction region according to targeted levels of bone growth;

wherein the plurality of electrodes comprises a set of cathode electrodes configured in connection with the control circuitry for excitation as cathodes, wherein the set of cathode electrodes are positioned on the spinal cage body based on position of the targeted osteoinduction region relative to the spinal cage body;

wherein the targeted osteoinduction region is adjacent to a subregion of an external wall; and wherein the spinal cage body comprises a defined side through-hole with one end within the subregion of the external wall and a second end within an internal wall defining the graft window cavity.

9. The system of claim 1, wherein the spinal cage body is an ALIF cage type and further comprises at least a second defined graft window cavity; wherein the plurality of electrodes includes: three electrodes set as cathodes during stimulation mode that are positioned on an interior wall of the defined graft window cavity and a second three electrodes set as cathodes during stimulation mode that are positioned on an interior wall of the second defined graft window cavity, and one electrode set as an anode during stimulation mode and positioned on an outer wall on the posterior side of the spinal cage implant.

10. The system of claim 1, wherein the spinal cage body is a TLIF cage type; wherein the plurality of electrodes includes four electrodes set as cathodes during stimulation mode and positioned along internal walls of the defined graft window cavity, and two electrodes set as anodes during stimulation mode and positioned on outer walls on the posterior side of the spinal cage implant.

11. The system of claim 1, wherein the spinal cage body is a Lateral cage type and further comprises at least a second defined graft window cavity; wherein the plurality of electrodes includes: four electrodes set as cathodes during stimulation mode that are positioned on an interior wall of the defined graft window cavity and a second four electrodes set as cathodes during stimulation mode that are positioned on an interior wall of the second defined graft window cavity, and two electrodes set as anodes during stimulation mode and positioned on an outer wall on the posterior side of the spinal cage implant.

12. The system of claim 1, wherein configuration to trigger the response includes configuration to deactivate at least a subset of electrodes to adjust stimulation distribution relative to the spinal cage body.

13. The system of claim 12, wherein the targeted osteoinduction region includes the defined graft window cavity, wherein the configuration to excite the plurality of electrodes further includes configuration to generate, in the graft window cavity within one millimeter of a defined endplate surface of the spinal cage body, an average current density between 1.8-9.1 $\mu A/cm^2$ and a current density in the targeted non-osteoinduction region below 1.8 $\mu A/cm^2$ when in the stimulation mode.

14. A method comprising:

providing a spinal cage implant that includes a spinal cage body with a defined graft window, a plurality of electrodes;

setting a stimulation profile, wherein an osteoinduction region is defined relative to the spinal cage body and a non-osteoinduction region is defined relative to the spinal cage body, wherein the osteoinduction region includes the defined graft window cavity;

stimulating the plurality of electrodes during a stimulation mode, comprising generating a current density in the osteoinduction region, within one millimeter of a defined endplate surface of the spinal cage body, an average current density between 1.8-9.1 $\mu$A/cm$^2$ and a current density in the non-osteoinduction region below 1.8 $\mu$A/cm$^2$; and monitoring impedance measurements between at least two electrodes to form an impedance dataset and triggering a response based on comparison of the impedance dataset and targeted levels of bone growth, comprising detecting a bone formation state when impedance measurements in the osteoinduction region reaches 1.2-1.5 k$\Omega$ and detecting a non-bone tissue state when impedance measurements in the non-osteoinduction region is less than 0.6-0.8 k$\Omega$.

* * * * *